(12) United States Patent
Garvey et al.

(10) Patent No.: US 9,499,464 B2
(45) Date of Patent: Nov. 22, 2016

(54) OPSIN-BINDING LIGANDS, COMPOSITIONS AND METHODS OF USE

(71) Applicant: Bikam Pharmaceuticals, Inc., Lexington, MA (US)

(72) Inventors: David S. Garvey, Dover, MA (US); Gregory J. Larosa, Newton, MA (US); Jeremy R. Greenwood, Brooklyn, NY (US); Leah L. Frye, Portland, OR (US); Tan Quach, Scarborough (CA); Jamie B. Cote, Newmarket (CA); Judd Berman, Toronto (CA)

(73) Assignee: BIKAM PHARMACEUTICALS, INC., Lexington, MA (US)

( * ) Notice: Subject to any disclaimer, the term of this patent is extended or adjusted under 35 U.S.C. 154(b) by 0 days.

(21) Appl. No.: 14/352,178

(22) PCT Filed: Oct. 19, 2012

(86) PCT No.: PCT/US2012/000522
§ 371 (c)(1),
(2) Date: Apr. 16, 2014

(87) PCT Pub. No.: WO2013/058809
PCT Pub. Date: Apr. 25, 2013

(65) Prior Publication Data
US 2014/0256782 A1 Sep. 11, 2014

Related U.S. Application Data

(60) Provisional application No. 61/627,855, filed on Oct. 19, 2011, provisional application No. 61/561,434, filed on Nov. 18, 2011, provisional application No. 61/564,401, filed on Nov. 29, 2011.

(51) Int. Cl.
| | |
|---|---|
| *C07D 209/34* | (2006.01) |
| *C07D 307/83* | (2006.01) |
| *C07C 49/443* | (2006.01) |
| *C07C 49/553* | (2006.01) |
| *C07C 35/32* | (2006.01) |
| *C07C 69/75* | (2006.01) |
| *C07C 233/58* | (2006.01) |

(52) U.S. Cl.
CPC ............. *C07C 49/443* (2013.01); *C07C 35/32* (2013.01); *C07C 49/553* (2013.01); *C07C 69/75* (2013.01); *C07C 233/58* (2013.01); *C07D 209/34* (2013.01); *C07D 307/83* (2013.01)

(58) Field of Classification Search
CPC .......................... C07D 209/34; C07D 307/83
See application file for complete search history.

(56) References Cited

U.S. PATENT DOCUMENTS

| | | | |
|---|---|---|---|
| 2001/0012902 A1 | 8/2001 | Yokoyama | |
| 2007/0043224 A1 | 2/2007 | Levorse | |
| 2009/0281149 A1 | 11/2009 | Scott et al. | |

FOREIGN PATENT DOCUMENTS

| | | |
|---|---|---|
| WO | 0109076 A2 | 2/2001 |
| WO | WO2008/013983 | 1/2008 |
| WO | WO 2008/013984 | 1/2008 |
| WO | WO2008/013986 | 1/2008 |
| WO | WO 2010/147653 | 12/2010 |
| WO | WO 2011/155983 | 12/2011 |

OTHER PUBLICATIONS

Antczak, et al. Document No. 101:2305025, retrieved from CAPLUS; (1984).*
Juvenile Macular Degeneration: Stargardt's and Best Disease [online], retrieved from the internet on Mar. 7, 2016. URL; http://www.webmd.com/eye-health/juvenile-macular-degeneration-stargardts.*
International Search Report for PCT/US2012/00522.

* cited by examiner

*Primary Examiner* — Shawquia Jackson
(74) *Attorney, Agent, or Firm* — Troutman Sanders LLP

(57) ABSTRACT

Compounds are disclosed that are useful for treating ophthalmic conditions caused by or related to production of toxic is visual cycle products that accumulate in the eye, such as dry adult macular degeneration, as well as conditions caused by or related to the misfolding of mutant opsin proteins and/or the mis-localization of opsin proteins. Compositions of these compounds alone or in combination with other therapeutic agents are also described, along with therapeutic methods of using such compounds and/or compositions. Methods of synthesizing such agents are also disclosed.

16 Claims, 1 Drawing Sheet

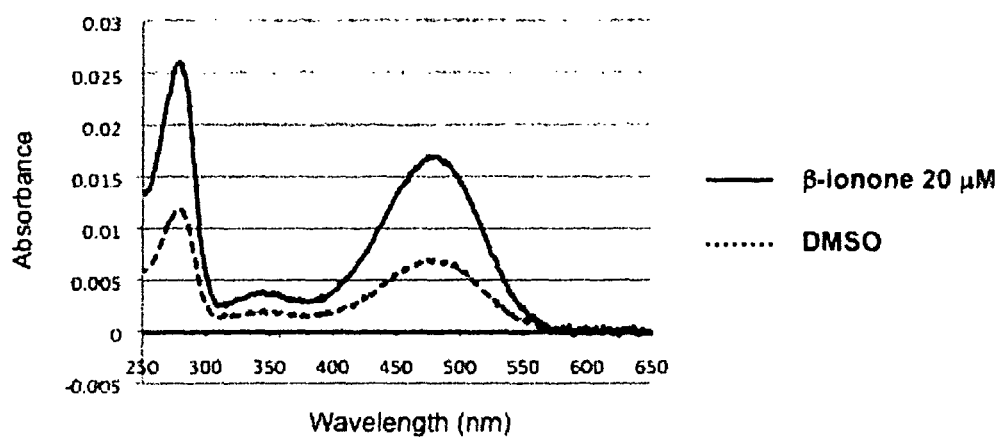

OPSIN-BINDING LIGANDS, COMPOSITIONS AND METHODS OF USE

This application is a national phase filing under 35 U.S.C. 1.371 of PCT/US2012/000522, filed 19 Oct. 2012, which claims priority of U.S. Provisional Application Ser. No. 61/564,401, filed 29 Nov. 2011, Ser. No. 61/561,434, filed 18 Nov. 2011, and Ser. No. 61/627,855, filed 19 Oct. 2011, the disclosures of all of which are incorporated herein by reference in their entirety.

FIELD OF THE INVENTION

The present invention relates to compounds and compositions thereof for use in the treatment and/or prevention of ophthalmic diseases as well as methods of using such compounds and/or compositions.

BACKGROUND OF THE INVENTION

A diminished visual acuity or total loss of vision may result from a number of eye diseases or disorders caused by dysfunction of tissues or structures in the anterior segment of the eye and/or posterior segment of the eye. Of those that occur as a consequence of a dysfunction in the anterior segment, aberrations in the visual cycle are often involved. The visual cycle (also frequently referred to as the retinoid cycle) comprises a series of light-driven and/or enzyme catalyzed reactions whereby a light-sensitive chromophore (called rhodopsin) is formed by covalent bonding between the protein opsin and the retinoid agent 11-cis-retinal and subsequently, upon exposure to light, the 11-cis-retinal is converted to all-trans-retinal, which can then be regenerated into 11-cis-retinal to again interact with opsin. A number of visual, ophthalmic, problems can arise due to interference with this cycle. It is now understood that at least some of these problems are due to improper protein folding, such as that of the protein opsin.

The main light and dark photoreceptor in the mammalian eye is the rod cell, which contains a folded membrane containing protein molecules that can be sensitive to light, the main one being opsin. Like other proteins present in mammalian cells, opsin is synthesized in the endoplasmic reticulum (i.e., on ribosomes) of the cytoplasm and then conducted to the cell membrane of rod cells. In some cases, such as due to genetic defects and mutation of the opsin protein, opsin can exhibit improper folding to form a conformation that either fails to properly insert into the membrane of the rod cell or else inserts but then fails to properly react with 11-cis-retinal to form native rhodopsin. In either case, the result is moderate to severe interference with visual perception in the animal so afflicted.

Among the diseases and conditions linked to improper opsin folding' is retinitis pigmentosa (RP), a progressive ocular-neurodegenerative disease (or group of diseases) that affects an estimated 1 to 2 million people worldwide. In RP, photoreceptor cells in the retina are damaged or destroyed, leading to loss of peripheral vision (i.e., tunnel vision) and subsequent partial or near-total blindness.

In the American population the most common defect occurs as a result of replacement of a proline residue by a histidine residue at amino acid number 23 in the opsin polypeptide chain (dubbed "P23H"), caused by a mutation in the gene for opsin. The result is production of a destabilized form of the protein, which is misfolded and aggregates in the cytoplasm rather than being transported to the cell surface. Like many other protein conformational diseases (PCDs), the clinically common P23H opsin mutant associated with autosomal dominant RP is misfolded and retained intracellularly. The aggregation of the misfolded protein is believed to result in photoreceptor damage and cell death.

Recent studies have identified small molecules that stabilize misfolded mutant proteins associated with disease. Some of these, dubbed "chemical chaperones," stabilize proteins non-specifically. Examples of these include glycerol and trimethylamine oxide. These are not very desirable for treating ophthalmic disease because such treatment usually requires high dosages that may cause toxic side effects. Other agents, dubbed "pharmacological chaperones," (which include native ligands and substrate analogs) act to stabilize the protein by binding to specific sites and have been identified for many misfolded proteins, e.g., G-protein coupled receptors. Opsin is an example of a G-protein coupled receptor and its canonical pharmacological chaperones include the class of compounds referred to as retinoids. Thus, certain retinoid compounds have been shown to stabilize mutant opsin proteins (see, for example, U.S. Patent Pub. 2004-0242704, as well as Noorwez et al., J. Biol. Chem., 279(16): 16278-16284 (2004)).

The visual cycle comprises a series of enzyme catalyzed reactions, usually initiated by a light impulse, whereby the visual chromophore of rhodopsin, consisting of opsin protein bound covalently to 11-cis-retinal, is converted to an all-trans-isomer that is subsequently released from the activated rhodopsin to form opsin and the all-trans-retinal product. This part of the visual cycle occurs in the outer portion of the rod cells of the retina of the eye. Subsequent parts of the cycle occur in the retinal pigmented epithelium (RPE). Components of this cycle include various enzymes, such as dehydrogenases and isomerases, as well as transport proteins for conveying materials between the RPE and the rod cells.

As a result of the visual cycle, various products are produced, called visual cycle products. One of these is all-trans-retinal produced in the rod cells as a direct result of light impulses contacting the 11-cis-retinal moiety of rhodopsin. All-trans-retinal, after release from the activated rhodopsin, can be regenerated back into 11-cis-retinal or can react with an additional molecule of all-trans-retinal and a molecule of phosphatidylethanolamine to produce N-retinylidene-N-retinylethanolamine (dubbed "A2E"), an orange-emitting fluorophore that can subsequently collect in the rod cells and in the retina pigmented epithelium (RPE). As A2E builds up (as a normal consequence of the visual cycle) it can also be converted into lipofuscin, a toxic substance that has been implicated in several abnormalities, including ophthalmic conditions such as wet and dry age related macular degeneration (ARMD). A2E can also prove toxic to the RPE and has been associated with dry ARMD.

Because the build-up of toxic visual cycle products is a normal part of the physiological process, it is likely that all mammals, especially all humans, possess such an accumulation to some extent throughout life. However, during surgical procedures on the eye, especially on the retina, where strong light is required over an extended period, for example, near the end of cataract surgery and while implanting the new lens, these otherwise natural processes can cause toxicity because of the build-up of natural products of the visual cycle. Additionally, excessive rhodopsin activation as a result of bright light stimulation can cause photoreceptor cell apoptosis via an AP-1 transcription factor dependent mechanism. Because of this, there is a need for agents that can be administered prior to, during or after (or any combination of these) the surgical process and that has the effect of inhibiting rhodopsin activation as well as reducing the production of visual cycle products that would otherwise accumulate and result in toxicity to the eye, especially to the retina.

The present invention answers this need by providing small molecules which noncovalently bind to opsin or mutated forms of opsin for treating and/or amelioration such conditions, if not preventing them completely. Importantly, such agents are not natural retinoids and thus are not tightly controlled for entrance into the rod cells, where mutated forms of opsin are synthesized and/or visual cycle products otherwise accumulate. Therefore, such agents can essentially be titrated in as needed for facilitating the proper folding trafficking of mutated opsins to the cell membrane or prevention of rhodopsin activation that can lead to the excessive build-up of visual cycle products like all-trans-retinal that in turn can lead to toxic metabolic products. Such compounds may compete with 11-cis-retinal to reduce all-trans-retinal by tying up the retinal binding pocket of opsin to prevent excessive all-trans-retinal build up. Thus, the compounds provided by the present invention have the advantage that they do not directly inhibit the enzymatic processes by which 11-cis-retinal is produced in the eye (thus not contributing to retinal degeneration). Instead, the formation of all-trans-retinal is limited and thereby the formation of A2E is reduced. Finally, by limiting the ability of 11-cis-retinal to combine with opsin to form rhodopsin, rhodopsin activation caused by bright light stimulation especially during ophthalmic surgery is also diminished thus preventing the photocell death that results.

Mislocalization of photoreceptor cell visual pigment proteins (opsins) can occur in various ocular diseases, and also with normal aging. In both cases the accumulation of mislocalized opsin leads to the decline in viability of photoreceptor cells. With time this mislocalized opsin accumulation leads to rod and cone cell death, retinal degeneration, and loss of vision. The present invention solves this problem by providing a method of correcting mislocalized opsin within a photoreceptor cell by contacting a mislocalized opsin protein with an opsin-binding agent that binds reversibly and/or non-covalently to said mislocalized opsin protein, and promotes the appropriate intracellular processing and transport of said opsin protein. This correction of mislocalization relieves photoreceptor cell stress, preventing decline in viability and death of photoreceptor cells in various diseases of vision loss, and in normal age-related decline in dim-light and peripheral rod-mediated vision, central cone-mediated vision, and loss of night vision.

BRIEF SUMMARY OF THE INVENTION

In one aspect, the present invention provides compounds having the structure of Formula I, including pharmaceutically acceptable salts, solvates and hydrates thereof, and compositions of said compounds:

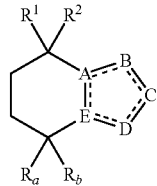

Formula I wherein $R^1$, $R^2$, $R_a$, $R_b$ and A=B=C=D=E are as described elsewhere herein.

In a related aspect, the present invention relates to a method of inhibiting the formation or accumulation of a visual cycle product, comprising contacting an opsin protein with a compound recited herein to inhibit formation of said visual cycle product relative to when said contacting does not occur.

In a further aspect, the present invention relates to a method to reduce the light toxicity associated with ophthalmic surgery by preventing rhodopsin regeneration during surgery to a mammalian eye and/or prevent or slow the formation of toxic visual cycle products by fractionally preventing rhodopsin formation during periods of light activation thereby providing a treatment of ocular conditions associated with the build up of visual products such as wet or dry ARMD.

In yet a further aspect, the present invention relates to a method of correcting the proper folding and trafficking of mutated opsin proteins, comprising contacting a mutated opsin protein with a compound that stabilizes the proper three dimensional conformation of the protein relative to when said contacting does not occur wherein the compound has the structure of Formula I including pharmaceutically acceptable salts, solvates and hydrates thereof.

In one embodiment, the ligand selectively binds reversibly or non-covalently to opsin. In another embodiment, the ligand binds at or near the 11-cis-retinal binding pocket of the opsin protein. In yet another embodiment, the ligand binds to the opsin protein so as to inhibit or slow the covalent binding of 11-cis-retinal to the opsin protein when the 11-cis-retinal is contacted with the opsin protein in the presence of the ligand. In yet another embodiment, the ligand binds to the opsin in the retinal binding pocket of opsin protein or disrupts 11-cis-retinal binding to the retinal binding pocket of opsin. In yet another embodiment, the ligand binds to the opsin protein so as to inhibit covalent binding of 11-cis-retinal to the opsin protein. In yet another embodiment, the mammal is a human being.

In yet another embodiment, slowing or halting the progression of wet or dry ARMD is associated with reducing the level of a visual cycle product, for example, a visual cycle product formed from all-trans-retinal, such as lipofuscin or N-retinylidine-N-retinylethanolamine (A2E). In yet another embodiment slowing or halting the progression of RP is associated with correcting the folding of mutated opsins. In another embodiment, the administering is topical administration, local administration (e.g., intraocular or periocular injection or implant) or systemic administration (e.g., oral, injection). In yet another embodiment, the light toxicity is related to an ophthalmic procedure (e.g., ophthalmic surgery). In still another embodiment, the administering occurs prior to, during, or after the ophthalmic surgery.

Mislocalization of photoreceptor cell visual pigment proteins (opsins) can occur in various ocular diseases, and also with normal aging. In such cases the accumulation of mislocalized opsin leads to the decline in viability of photoreceptor cells. With time this mislocalized opsin accumulation leads to rod and cone cell death, retinal degeneration, and loss of vision. In one aspect, the invention provides a method of correcting mislocalized opsin within a photoreceptor cell, comprising contacting a mislocalized opsin protein with an opsin-binding agent that binds reversibly and/or non-covalently to said mislocalized opsin protein to promote the appropriate intracellular processing and transport of said opsin protein. This correction of mislocalization reduces photoreceptor cell stress, preventing photoreceptor cell decline in viability and death in various diseases of vision loss, and in normal age-related decline in dim-light and peripheral rod-mediated vision, central cone-mediated vision, and loss of night vision.

In various embodiments, the ocular protein mislocalization disorder is any one or more of wet or dry form of macular degeneration, retinitis pigmentosa, a retinal or macular dystrophy, Stargardt's disease, Sorsby's dystrophy, autosomal dominant drusen, Best's dystrophy, peripherin mutation associate with macular dystrophy, dominant form of Stargardt's disease, North Carolina macular dystrophy, light toxicity, retinitis pigmentosa, normal vision loss related aging and normal loss of night vision related to aging.

In still another embodiment, the method further involves administering to a mammal, preferably a human being, an effective amount of at least one additional agent selected from the group consisting of a proteasomal inhibitor, an autophagy inhibitor, a lysosomal inhibitor, an inhibitor of protein transport from the ER to the Golgi, an Hsp90 chaperone inhibitor, a heat shock response activator, a glycosidase inhibitor, and a histone deacetylase inhibitor. In yet another embodiment, the opsin binding ligand and the additional agent are administered simultaneously.

In still another embodiment, the opsin binding ligand and the additional agent are each incorporated into a composition that provides for their long-term release. In another embodiment, the composition is part of a microsphere, nanosphere, nano emulsion or implant. In another embodiment, the composition further involves administering a mineral supplement, at least one anti-inflammatory agent, such as a steroid (e.g., any one or more of cortisone, hydrocortisone, prednisone, prednisolone, methylprednisolone, triamcinolone, betamethasone, beclamethasone and dexamethasone), or at least one anti-oxidant, such as vitamin A, vitamin C and vitamin E. In various embodiments, the opsin binding ligand, the anti-inflammatory agent, and/or the anti-oxidant are administered simultaneously.

BRIEF DESCRIPTION OF THE DRAWING

FIG. 1 shows the increase in regeneration of 500 nm absorbing pigment upon treatment with retinal from P23H opsin that was treated with 20 $\square$M of $\square$-ionone during mutant protein production relative to pigment formation in the presence of vehicle (DMSO) alone.

DEFINITIONS

As used throughout the disclosure, the following terms, unless otherwise indicated, shall be understood to have the following meanings.

By "mislocalization" of a photoreceptor cell visual pigment protein (for example, opsin, especially human opsin) is meant that the synthesized protein is not found at the normal or appropriate cellular location.

"Pharmacologic chaperones" refer to small molecular weight chemical compounds that interact with a protein (usually with a misfolded, or unfolded protein) in such a way as to alter the folding or confirmation of said protein. Such an interaction can have diverse consequences on the cellular fate of the protein, including but not limited to leading to increased stability and increased levels of functional protein, increased stability and increased levels of non-functional protein, or decreased stability and decreased levels of functional or non-functional protein.

"Productive chaperone" refers to a pharmacologic chaperone that when interacting with a protein leads to an increased level of functional protein.

"Counterproductive; shipwreck or destructive chaperone" refers to a pharmacologic chaperone that interacts with a protein (usually with a mis-folded, or un-folded protein) and this interaction leads to a decreased stability and/or decreased levels of functional or non-functional protein.

By "proteasomal inhibitor" is meant a compound that reduces a proteasomal activity, such as the degradation of a ubiquinated protein.

By "autophagy inhibitor" is meant a compound that reduces the degradation of a cellular component by a cell in which the component is located.

By "lysosomal inhibitor" is meant a compound that reduces the intracellular digestion of macromolecules by a lysosome. In one embodiment, a lysosomal inhibitor decreases the proteolytic activity of a lysosome.

By "Inhibitor of ER-Golgi protein transport" is meant a compound that reduces the transport of a protein from the ER (endoplasmic reticulum) to the Golgi, or from the Golgi to the ER.

By "HSP90 chaperone inhibitor" is meant a compound that reduces the chaperone activity of heat shock protein 90 (HSP90). In one embodiment, the inhibitor alters protein binding to an HSP90 ATP/ADP pocket.

By "heat shock response activator" is meant a compound that increases the chaperone activity or expression of a heat shock pathway component. Heat shock pathway components include, but are not limited to, HSP100, HSP90, HSP70, HASP60, HSP40 and small HSP family members.

By "glycosidase inhibitor" is meant a compound that reduces the activity of an enzyme that cleaves a glycosidic bond.

By "histone deacetylase inhibitor" is meant a compound that reduces the activity of an enzyme that deacetylates a histone.

By "reduces" or "increases" is meant a negative or positive alteration, respectively. In particular embodiments, the alteration is by at least about 10%, 25%, 50%, 75%, or 100% of the initial level of the protein produced in the absence of the opsin binding ligand.

As used herein, the term "wild-type conformation" refers to the three dimensional conformation or shape of a protein that is free of mutations to its amino acid sequence. For opsin, this means a protein free from mutations that cause misfiling, such as the mutation designated P23H (meaning that a proline is replaced by a histidine at residue 23 starting from the N-terminus). Opsin in a "wild-type conformation" is capable of opsin biological function, including but not limited to, retinoid binding, visual cycle function, and insertion into a photoreceptor membrane.

By "agent" is meant a small compound (also called a "compound"), polypeptide, polynucleotide, or fragment thereof. The terms compound and agent are used interchangeably unless specifically stated otherwise herein for a particular agent or compound.

By "correcting the conformation" of a protein is meant inducing the protein to assume a conformation having at least one biological activity associated with a wild-type protein.

By "misfolded opsin protein" is meant a protein whose tertiary structure differs from the conformation of a wild-type protein, such that the misfolded protein lacks one or more biological activities associated with the wild-type protein.

By "selectively binds" is meant a compound that recognizes and binds a polypeptide of the invention, such as opsin, but which does not substantially recognize and bind other molecules, especially non-opsin polypeptides, in a sample, for example, a biological sample.

By "effective amount" or "therapeutically effective amount" is meant a level of an agent sufficient to exert a physiological effect on a cell, tissue, or organ or a patient. As used herein, it is the amount sufficient to effect the methods of the invention to achieve the desired result.

By "pharmacological chaperone" is meant a molecule that upon contacting a mutant protein is able to facilitate/stabilize the proper folding of the protein such that it acts and functions much more like wild type protein than would be the case in the absence of the molecule.

By "control" is meant a reference condition. For example, where a cell contacted with an agent of the invention is compared to a corresponding cell not contacted with the agent, the latter is the "control" or "control" cell.

By "treat" is meant decrease, suppress, attenuate, diminish, arrest, or stabilize the development or progression of a disease, preferably an ocular disease, such as RP, AMD and/or light toxicity.

By "prevent" is meant reduce the risk that a subject will develop a condition, disease, or disorder, preferably an ocular disease, such as RP, AMD and/or light toxicity.

By "competes for binding" is meant that a compound of the invention and an endogenous ligand are incapable of binding to a target at the same time. Assays to measure competitive binding are known in the art, and include, measuring a dose dependent inhibition in binding of a compound of the invention and an endogenous ligand by measuring $t_{1/2}$, for example.

A "pharmaceutically acceptable salt" is a salt formed from an acid or a basic group of one of the compounds of the invention. Illustrative salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesuifonate, and pamoate (i.e., 1,1'-methytene-bis-(2-hydroxy-3-naphthoate)) salts.

The term "pharmaceutically acceptable salt" also refers to a salt prepared from a compound of the invention having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl-N-ethylamine; diethylamine; triethylamine; mono-, bis-, or tris-(2-hydroxy-lower alkylamines), such as mono-, bis-, or tris-(2-hydroxyethyl)-amine, 2-hydroxy-tert-butylamine, or tris-(hydroxymethyl)methylamine, N,N-di-lower alkyl-N-(hydroxy lower alkyl)-amines, such as N,N-dimethyl-N-(2-hydroxyethyl)-amine, or tri-(2-hydroxyethyl)amine; N-methyl-D-glucamine; and amino acids such as arginine, lysine, and the like.

The term "pharmaceutically acceptable salt" also refers to a salt prepared from a compound disclosed herein, e.g., a salt of a compound of Example 1, having a basic functional group, such as an amino functional group, and a pharmaceutically acceptable inorganic or organic acid. Suitable acids include, but are not limited to, hydrogen sulfate, citric acid, acetic acid, oxalic acid, hydrochloric acid, hydrogen bromide, hydrogen iodide, nitric acid, phosphoric acid, isonicotinic acid, lactic acid, salicylic acid, tartaric acid, ascorbic acid, succinic acid, maleic acid, besylic acid, fumaric acid, gluconic acid, glucaronic acid, saccharic acid, formic acid, benzoic acid, glutamic acid, methanesulfonic acid, ethanesulfonic acid, benzenesulfonic acid, and p-toluenesulfonic acid.

The term "pharmaceutically-acceptable excipient" as used herein means one or more compatible solid or liquid tiller, diluents or encapsulating substances that are suitable for administration into a human. The term "excipient" includes an inert substance added to a pharmacological composition to further facilitate administration of a compound. Examples of excipients include but are not limited to calcium carbonate, calcium phosphate, various sugars and types of starch, cellulose derivatives, gelatin, vegetable oils and polyethylene glycols.

The term "carrier" denotes an organic or inorganic ingredient, natural or synthetic, with which the active ingredient is combined to facilitate administration.

The term "parenteral" includes subcutaneous, intrathecal, intravenous, intramuscular, intraperitoneal, or infusion.

The term "visual cycle product" refers to a chemical entity produced as a natural product of one or more reactions of the visual cycle (the reactive cycle whereby opsin protein binds 11-cis-retinal to form rhodopsin, which accepts a light impulse to convert 11-cis-retinal to all trans-retinal, which is then released from the molecule to regenerate opsin protein with subsequent binding of a new 11-cis-retinal to regenerate rhodopsin). Such visual cycle products include, but are not limited to, all-trans-retinal, lipofuscin and A2E.

The term "light toxicity" refers to any condition affecting vision that is associated with, related to, or caused by the production and/or accumulation of visual cycle products. Visual cycle products include, but are not limited to, all-trans-retinal, lipofuscin or A2E. In one particular embodiment, light toxicity is related to exposure of the eye to large amounts of light or to very high light intensity, occurring, for example, during a surgical procedure on the retina.

The term "opsin" refers to an opsin protein, preferably a mammalian opsin protein, most preferably a human opsin protein. In one embodiment, the opsin protein is in the wild-type (i.e., physiologically active) conformation. One method of assaying for physiological activity is assaying the ability of opsin to bind 11-cis-retinal and form active rhodopsin. A mutant opsin, such as the P23H mutant, that is ordinarily misfolded has a reduced ability to bind 11-cis-retinal, and therefore forms little or no rhodopsin. Where the conformation of the mutant opsin has been corrected (for example, by binding to a pharmacological chaperone), the opsin is correctly inserted into the rod cell membrane so that its conformation is the same, or substantially the same, as that of a non-mutant opsin. This allows the mutant opsin to bind 11-cis-retinal to form active rhodopsin. Therefore, the methods of the invention operate to reduce the formation of visual cycle products.

"Alkyl" refers to an unbroken non-cyclic chain of carbon atoms that may be substituted with other chemical groups. It may also be branched or unbranched, substituted or unsubstituted.

"Lower alkyl" refers to a branched or straight chain acyclic alkyl group comprising one to ten carbon atoms, preferably one to eight carbon atoms, more preferably one to six carbon atoms. Exemplary lower alkyl groups include methyl, ethyl, n-propyl, isopropyl, n-butyl, isobutyl, sec-butyl, t-butyl, pentyl, neopentyl, iso-amyl, hexyl, and octyl.

All alkyl, alkenyl or alkynyl groups disclosed herein may be substituted with one or more of the following: lower alkyl, hydroxy, ester, amidyl, oxo, carboxyl, carboxamido, halo, cyano, nitrate, nitrite, thionitrate, thionitrite sulfhydryl and amino groups (as elsewhere defined herein).

"Haloalkyl" refers to a lower alkyl group, an alkenyl group, an alkynyl group, a bridged cycloalkyl group, a cycloalkyl group or a heterocyclic ring, as defined herein, to which is appended one or more halogens, as defined herein. Exemplary haloalkyl groups include trifluoromethyl, chloromethyl, 2-bromobutyl and 1-bromo-2-chloro-pentyl.

"Alkenyl" refers to a branched or straight chain $C_2$-$C_{10}$ hydrocarbon (preferably a $C_2$-$C_8$ hydrocarbon, more preferably a $C_2$-$C_6$ hydrocarbon) that can comprise one or more carbon-carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl and octen-1-yl.

"Lower alkenyl" refers to a branched or straight chain $C_2$-$C_4$ hydrocarbon that can comprise one or two carbon-carbon double bonds.

"Substituted alkenyl" refers to a branched or straight chain $C_2$-$C_{10}$ hydrocarbon (preferably a $C_2$-$C_8$ hydrocarbon, more preferably a $C_2$-$C_6$ hydrocarbon) which can comprise one or more carbon-carbon double bonds, wherein one or more of the hydrogen atoms have been replaced with one or more $R^{100}$ groups, wherein each $R^{100}$ is independently a hydroxy, an oxo, a carboxyl, a carboxamido, a halo, a cyano or an amino group, as defined herein.

"Alkynyl" refers to an unsaturated acyclic $C_2$-$C_{10}$ hydrocarbon (preferably a $C_2$-$C_8$ hydrocarbon, more preferably a $C_2$-$C_6$ hydrocarbon) that can comprise one or more carbon-carbon triple bonds. Exemplary alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl and 3,3-dimethyl-butyn-1-yl.

"Lower alkynyl" refers to a branched or straight chain $C_2$-$C_4$ hydrocarbon that can comprise one or two carbon-carbon triple bonds "Bridged cycloalkyl" refers to two or more cycloalkyl groups, heterocyclic groups, or a combination thereof fused via adjacent or non-adjacent atoms. Bridged cycloalkyl groups can be unsubstituted or substituted with one, two or three substituents independently selected from alkyl, alkoxy, amino, alkylamino, dialkylamino, hydroxy, halo, carboxyl, alkylcarboxylic acid, aryl, amidyl, ester, alkylcarboxylic ester, carboxamido, alkylcarboxamido, oxo and nitro. Exemplary bridged cycloalkyl groups include adamantyl, decahydronapthyl, quinuclidyl, 2,6-dioxabicyclo(3.3.0)octane, oxabicyclo(2.2.1)heptyl and 8-azabicyclo(3,2,1)oct-2-enyl.

"Cycloalkyl" refers to a saturated or unsaturated cyclic hydrocarbon comprising from about 3 to about 10 carbon atoms. Cycloalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo, alkylsulfinyl, and nitro. Exemplary cycloalkyl groups include cyclopropyl, cyclobutyl, cyclopentyl, cyclohexyl, cyclohexenyl and cyclohepta-1,3-dienyl.

"Heterocyclic ring or group" refers to a saturated or unsaturated cyclic or polycyclic hydrocarbon group having about 2 to about 12 carbon atoms where 1 to about 4 carbon atoms are replaced by one or more nitrogen, oxygen and/or sulfur atoms. Sulfur may be in the thio, sulfinyl or sulfonyl oxidation state. The heterocyclic ring or group can be fused to an aromatic hydrocarbon group. Heterocyclic groups can be unsubstituted or substituted with one, two or three substituents independently selected from alkyl, alkoxy, amino, alkylthio, aryloxy, arylthio, arylalkyl, hydroxy, oxo, thial, halo, carboxyl, carboxylic ester, alkylcarboxylic acid, alkylcarboxylic ester, aryl, arylcarboxylic acid, arylcarboxylic ester, amidyl, ester, alkylcarbonyl, arylcarbonyl, alkylsulfinyl, carboxamido, alkylcarboxamido, arylcarboxamido, sulfonic acid, sulfonic ester, sulfonamide nitrate and nitro. Exemplary heterocyclic groups include pyrrolyl, furyl, thienyl, 3-pyrrolinyl, 4,5,6-trihydro-2H-pyranyl, pyridinyl, 1,4-dihydropyridinyl, pyrazolyl, triazolyl, pyrimidinyl, pyridazinyl, oxazolyl, thiazolyl, thieno[2,3-d]pyrimidine, 4,5,6,7-tetrahydrobenzo[b]thiophene, imidazolyl, indolyl, thiophenyl, furanyl, tetrahydrofuranyl, tetrazolyl, pyrrolinyl, pyrrolindinyl, oxazolindinyl 1,3-dioxolanyl; imidazolinyl, imidazolindinyl, pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyl, benzothiazolinyl, quinolinyl and 2,6-dioxabicyclo(3.3.0)octane.

"Heterocyclic compounds" refer to mono- and polycyclic compounds comprising at least one aryl or heterocyclic ring.

"Aryl" refers to a monocyclic, bicyclic, carbocyclic or heterocyclic ring system comprising one or two aromatic rings. Exemplary aryl groups include phenyl, pyridyl, napthyl, quinoyl, tetrahydronaphthyl, furanyl, indanyl, indenyl, indoyl. Aryl groups (including bicyclic aryl groups) can be unsubstituted or substituted with one, two or three substituents independently selected from alkyl, alkoxy, alkylthio, amino, alkylamino, dialkylamino, arylamino, diarylamino, alkylarylamino, halo, cyano, alkylsulfinyl, hydroxy, carboxyl, carboxylic ester, alkylcarboxylic acid, alkylcarboxylic ester, aryl, arylcarboxylic acid, arylcarboxylic ester, alkylcarbonyl, arylcarbonyl, amidyl, ester, carboxamido, alkylcarboxamido, carbomyl, sulfonic acid, sulfonic ester, sulfonamido and nitro. Exemplary substituted aryl groups include tetrafluorophenyl, pentafluorophenyl, sulfonamide, alkylsulfonyl and arylsulfonyl.

"Cycloalkenyl" refers to an unsaturated cyclic $C_3$-$C_{10}$ hydrocarbon (preferably a $C_3$-$C_8$ hydrocarbon, more preferably a $C_3$-$C_6$ hydrocarbon), which can comprise one or more carbon-carbon double bonds.

"Alkylaryl" refers to an alkyl group, as defined herein, to which is appended an aryl group, as defined herein. Exemplary alkylaryl groups include benzyl, phenylethyl, hydroxybenzyl, fluorobenzyl and fluorophenylethyl.

"Arylalkyl" refers to an aryl radical, as defined herein, attached to an alkyl radical, as defined herein. Exemplary arylalkyl groups include benzyl, phenylethyl, 4-hydroxybenzyl, 3-fluorobenzyl and 2-fluorophenylethyl.

"Arylalkenyl" refers to an aryl radical, as defined herein, attached to an alkenyl radical, as defined herein. Exemplary arylalkenyl groups include styryl and propenylphenyl.

"Cycloalkylalkyl" refers to a cycloalkyl radical, as defined herein, attached to an alkyl radical, as defined herein.

"Cycloalkylalkoxy" refers to a cycloalkyl radical, as defined herein, attached to an alkoxy radical, as defined herein.

"Cycloalkylalkylthio" refers to a cycloalkyl radical, as defined herein, attached to an alkylthio radical, as defined herein.

"Heterocyclicalkyl" refers to a heterocyclic ring radical, as defined herein, attached to an alkyl radical, as defined herein.

"Arylheterocyclic ring" refers to a bi- or tricyclic ring comprised of an aryl ring, as defined herein, appended via two adjacent carbon atoms of the aryl ring to a heterocyclic ring, as defined herein. Exemplary arylheterocyclic rings include dihydroindole and 1,2,3,4-tetra-hydroquinoline.

"Alkylheterocyclic ring" refers to a heterocyclic ring radical, as defined herein, attached to an alkyl radical, as defined herein. Exemplary alkylheterocyclic rings include 2-pyridylmethyl and 1-methylpiperidin-2-one-3-methyl.

"Alkoxy" refers to $R_{50}O—$, wherein $R_{50}$ is an alkyl group, an alkenyl group or an alkynyl group as defined herein (preferably a lower alkyl group or a haloalkyl group, as defined herein). Exemplary alkoxy groups include methoxy, ethoxy, t-butoxy, cyclopentyloxy, trifluoromethoxy, propenyloxy and propargyloxy.

"Aryloxy" refers to $R_{55}O—$, wherein $R_{55}$ is an aryl group, as defined herein. Exemplary arylkoxy groups include phenoxy, napthyloxy, quinolyloxy, isoquinolizinyloxy.

"Alkylthio" refers to $R_{50}S—$, wherein $R_{50}$ is an alkyl group, as defined herein.

"Lower alkylthio" refers to a lower alkyl group, as defined herein, appended to a thio group, as defined herein.

"Arylalkoxy" or "alkoxyaryl" refers to an alkoxy group, as defined herein, to which is appended an aryl group, as defined herein. Exemplary arylalkoxy groups include benzyloxy, phenylethoxy and chlorophenylethoxy.

"Arylalklythio" refers to an alkylthio group, as defined herein, to which is appended an aryl group, as defined herein. Exemplary arylalklythio groups include benzylthio, phenylethylthio and chlorophenylethylthio.

"Arylalkylthioalkyl" refers to an arylalkylthio group, as defined herein, to which is appended an alkyl group, as defined herein. Exemplary arylalklythioalkyl groups include benzylthiomethyl, phenylethyithiomethyl and chlorophenylethylthioethyl.

"Alkylthioalkyl" refers to an alkylthio group, as defined herein, to which is appended an alkyl group, as defined herein. Exemplary alkylthioalkyl groups include allylthiomethyl, ethylthiomethyl and trifluoroethylthiomethyl.

"Alkoxyalkyl" refers to an alkoxy group, as defined herein, appended to an alkyl group, as defined herein. Exemplary alkoxyalkyl groups include methoxymethyl, methoxyethyl and isopropoxymethyl.

"Alkoxyhaloalkyl" refers to an alkoxy group, as defined herein, appended to a haloalkyl group, as defined herein. Exemplary alkoxyhaloalkyl groups include 4-methoxy-2-chlorobutyl.

"Cycloalkoxy" refers to $R_{54}O—$, wherein $R_{54}$ is a cycloalkyl group or a bridged cycloalkyl group, as defined herein. Exemplary cycloalkoxy groups include cyclopropyloxy, cyclopentyloxy and cyclohexyloxy.

"Cycloalkylthio" refers to $R_{54}S—$, wherein $R_{54}$ is a cycloalkyl group or a bridged cycloalkyl group, as defined herein. Exemplary cycloalkylthio groups include cyclopropylthio, cyclopentylthio and cyclohexylthio.

"Haloalkoxy" refers to an alkoxy group, as defined herein, in which one or more of the hydrogen atoms on the alkoxy group are substituted with halogens, as defined herein. Exemplary haloalkoxy groups include 1,1,1-trichloroethoxy and 2-bromobutoxy.

"Hydroxy" refers to —OH. "Oxy" refers to —O—. "Oxo" refers to $=O$.

"Oxylate" refers to $—O^-R_{77}^+$ wherein $R_{77}$ is an organic or inorganic cation.

"Thiol" refers to —SH. "Thio" refers to —S—.

"Oxime" refers to $=N—OR_{81}$ wherein $R_{81}$ is a hydrogen, an alkyl group, an aryl group, an alkylsulfonyl group, an arylsulfonyl group, a carboxylic ester, an alkylcarbonyl group, an arylcarbonyl group, a carboxamido group, an alkoxyalkyl group or an alkoxyaryl group.

"Hydrazone" refers to $=N—N(R_{81})(R'_{81})$ wherein $R'_{81}$ is independently selected from $R_{81}$, and $R_{81}$ is as defined herein.

"Hydrazino" refers to $H_2N—N(H)—$.

"Organic cation" refers to a positively charged organic ion. Exemplary organic cations include alkyl substituted ammonium cations.

"Inorganic cation" refers to a positively charged metal ion. Exemplary inorganic cations include Group I metal cations such as for example, sodium, potassium, magnesium and calcium.

"Hydroxyalkyl" refers to a hydroxy group, as defined herein, appended to an alkyl group, as defined herein.

"Nitrate" refers to —O—$NO_2$ i.e. oxidized nitrogen.

"Nitro" refers to the group —$NO_2$ and "nitrosated" refers to compounds that have been substituted therewith. "Nitrile" and "cyano" refer to —CN.

"Halogen" or "halo" refers to iodine (I), bromine (Br), chlorine (Cl), and/or fluorine (F).

"Imine" refers to —C($=N—R_{51}$)— wherein $R_{51}$ is a hydrogen atom, an alkyl group, an aryl group or an arylheterocyclic ring, as defined herein.

"Amine" refers to any organic compound that contains at least one basic nitrogen atom.

"Amino" refers to —$NH_2$, an alkylamino group, a dialkylamino group, an arylamino group, a diarylamino group, an alkylarylamino group or a heterocyclic ring, as defined herein.

"Alkylamino" refers to $R_{50}NH—$, wherein $R_{50}$ is an alkyl group, as defined herein. Exemplary alkylamino groups include methylamino, ethylamino, butylamino, and cyclohexylamino.

"Arylamino" refers to $R_{55}NH—$, wherein $R_{55}$ is an aryl group, as defined elsewhere herein.

"Dialkylamino" refers to $R_{52}R_{53}N—$, wherein $R_{52}$ and $R_{53}$ are each independently an alkyl group, as defined herein. Exemplary dialkylamino groups include dimethylamino, diethylamino and methyl propargylamino.

"Diarylamino" refers to $R_{55}R_{60}N—$, wherein $R_{55}$ and $R_{60}$ are each independently an aryl group, as defined herein.

"Alkylarylamino" or "arylalkylamino" refers to $R_{52}R_{55}N—$, wherein $R_{52}$ is an alkyl group, as defined herein, and $R_{55}$ is an aryl group, as defined herein.

"Alkylarylalkylamino" refers to $R_{52}R_{79}N—$, wherein $R_{52}$ is an alkyl group, as defined herein, and $R_{79}$ is an arylalkyl group, as defined herein.

"Alkylcycloalkylamino" refers to $R_{52}R_{80}N—$, wherein $R_{52}$ is an alkyl group, as defined herein, and $R_{80}$ is a cycloalkyl group, as defined herein.

"Aminoalkyl" refers to an amino group, an alkylamino group, a dialkylamino group, an arylamino group, a diarylamino group, an alkylarylamino group or a heterocyclic ring, as defined herein, to which is appended an alkyl group, as defined herein. Exemplary aminoalkyl groups include dimethylaminopropyl, diphenylaminocyclopentyl and methylaminomethyl.

"Aminoaryl" refers to an aryl group to which is appended an alkylamino group, an arylamino group or an arylalkylamino group. Exemplary aminoaryl groups include anilino, N-methylanilino and N-benzylanilino.

"Thio" refers to —S—. "Sulfinyl" refers to —S(O)—.

"Methanthial" refers to —C(S)—. "Thial" refers to =S.
"Sulfonyl" refers to —S(O)$_2$—.

"Sulfonic acid" refers to —S(O)$_2$OR$_{76}$, wherein R$_{76}$ is a hydrogen, an organic cation or an inorganic cation, as defined herein.

"Alkylsulfonic acid" refers to a sulfonic acid group, as defined herein, appended to an alkyl group, as defined herein.

"Arylsulfonic acid" refers to a sulfonic acid group, as defined herein, appended to an aryl group, as defined herein.

"Sulfonic ester" refers to —S(O)$_2$OR$_{58}$, wherein R$_{58}$ is an alkyl group, an aryl group, or an aryl heterocyclic ring, as defined herein.

"Sulfonamido" refers to —S(O)$_2$—N(R$_{51}$)(R$_{57}$), wherein R$_{51}$ and R$_{57}$ are each independently a hydrogen atom, an alkyl group, an aryl group or an arylheterocyclic ring, as defined herein, or R$_{51}$ and R$_{57}$ when taken together are a heterocyclic ring, a cycloalkyl group or a bridged cycloalkyl group, as defined herein.

"Alkylsulfonamido" refers to a sulfonamido group, as defined herein, appended to an alkyl group, as defined herein.

"Arylsulfonamido" refers to a sulfonamido group, as defined herein, appended to an aryl group, as defined herein.

"Alkylthio" refers to R$_{50}$S—, wherein R$_{50}$ is an alkyl group, as defined herein (preferably a lower alkyl group, as defined herein).

"Arylthio" refers to R$_{55}$S—, wherein R$_{55}$ is an aryl group, as defined herein.

"Arylalkylthio" refers to an aryl group, as defined herein, appended to an alkylthio group, as defined herein.

"Alkylsulfinyl" refers to R$_{50}$—S(O)—, wherein R$_{50}$ is an alkyl group, as defined herein.

"Alkylsulfonyl" refers to R$_{50}$—S(O)$_2$—, wherein R$_{50}$ is an alkyl group, as defined herein.

"Alkylsulfonyloxy" refers to R$_{50}$—S(O)$_2$—O—, wherein R$_{50}$ is an alkyl group, as defined herein.

"Arylsulfinyl" refers to R$_{55}$—S(O)—, wherein R$_{55}$ is an aryl group, as defined herein.

"Arylsulfonyl" refers to R$_{55}$—S(O)$_2$—, wherein R$_{55}$ is an aryl group, as defined herein.

"Arylsulfonyloxy" refers to R$_{55}$—S(O)$_2$—O—, wherein R$_{55}$ is an aryl group, as defined herein.

"Amidyl" refers to R$_{51}$C(O)N(R$_{57}$)— wherein R$_{51}$ and R$_{57}$ are each independently a hydrogen atom, an alkyl group, an aryl group or an arylheterocyclic ring, as defined herein.

"Ester" refers to R$_{51}$C(O)R$_{82}$— wherein R$_{51}$ is a hydrogen atom, an alkyl group, an aryl group or an arylheterocyclic ring, as defined herein and R$_{82}$ is oxygen or sulfur.

"Carbamoyl" refers to —O—C(O)N(R$_{51}$)(R$_{57}$), wherein R$_{51}$ and R$_{57}$ are each independently a hydrogen atom, an alkyl group, an aryl group or an arylheterocyclic ring, as defined herein, or R$_{51}$ and R$_{57}$ taken together are a heterocyclic ring, a cycloalkyl group or a bridged cycloalkyl group, as defined herein.

"Carboxyl" refers to —C(O)OR$_{76}$, wherein R$_{76}$ is a hydrogen, an organic cation or an inorganic cation, as defined herein.

"Carbonyl" refers to —C(O)—.

"Alkylcarbonyl" refers to R$_{52}$—C(O)—, wherein R$_{52}$ is an alkyl group, as defined herein.

"Arylcarbonyl" refers to R$_{55}$—C(O)—, wherein R$_{55}$ is an aryl group, as defined herein.

"Arylalkylcarbonyl" refers to R$_{55}$—R$_{52}$—C(O)—, wherein R$_{55}$ is an aryl group, as defined herein, and R$_{52}$ is an alkyl group, as defined herein.

"Alkylarylcarbonyl" refers to R$_{52}$—R$_{55}$—C(O)—, wherein R$_{55}$ is an aryl group, as defined herein, and R$_{52}$ is an alkyl group, as defined herein.

"Heterocyclicalkylcarbonyl" refer to R$_{78}$C(O)— wherein R$_{78}$ is a heterocyclicalkyl group, as defined herein.

"Carboxylic ester" refers to —C(O)OR$_{58}$, wherein R$_{58}$ is an alkyl group, an aryl group or an aryl heterocyclic ring, as defined herein.

"Alkylcarboxylic acid" and "alkylcarboxyl" refer to an alkyl group, as defined herein, appended to a carboxyl group, as defined herein.

"Alkylcarboxylic ester" refers to an alkyl group, as defined herein, appended to a carboxylic ester group, as defined herein.

"Alkyl ester" refers to an alkyl group, as defined herein, appended to an ester group, as defined herein.

"Arylcarboxylic acid" refers to an aryl group, as defined herein, appended to a carboxyl group, as defined herein.

"Arylcarboxylic ester" and "arylcarboxyl" refer to an aryl group, as defined herein, appended to a carboxylic ester group, as defined herein.

"Aryl ester" refers to an aryl group, as defined herein, appended to an ester group, as defined herein.

"Carboxamido" refers to —C(O)N(R$_{51}$)(R$_{57}$), wherein R$_{51}$ and R$_{57}$ are each independently a hydrogen atom, an alkyl group, an aryl group or an arylheterocyclic ring, as defined herein, or R$_{51}$ and R$_{57}$ when taken together are a heterocyclic ring, a cycloalkyl group or a bridged cycloalkyl group, as defined herein.

"Alkylcarboxamido" refers to an alkyl group, as defined herein, appended to a carboxamido group, as defined herein.

"Arylcarboxamido" refers to an aryl group, as defined herein, appended to a carboxamido group, as defined herein.

"Urea" refers to —N(R$_{59}$)—C(O)N(R$_{51}$)(R$_{57}$) wherein R$_{51}$, R$_{57}$, and R$_{59}$ are each independently a hydrogen atom, an alkyl group, an aryl group or an arylheterocyclic ring, as defined herein, or R$_{51}$ and R$_{57}$ taken together are a heterocyclic ring, a cycloalkyl group or a bridged cycloalkyl group, as defined herein.

"Phosphoryl" refers to —P(R$_{70}$)(R$_{71}$)(R$_{72}$), wherein R$_{70}$ is a lone pair of electrons, thial or oxo, and R$_{71}$ and R$_{72}$ are each independently a covalent bond, a hydrogen, a lower alkyl, an alkoxy, an alkylamino, a hydroxy, an oxy or an aryl, as defined herein.

"Phosphoric acid" refers to —P(O)(OR$_{51}$)OH wherein R$_{51}$ is a hydrogen atom, an alkyl group, an aryl group or an arylheterocyclic ring, as defined herein.

"Phosphinic acid" refers to —P(O)(R$_{51}$)OH wherein R$_{51}$ is a hydrogen atom, an alkyl group, an aryl group or an arylheterocyclic ring, as defined herein.

"Silyl" refers to —Si(R$_{73}$)(R$_{74}$)(R$_{75}$), wherein R$_{73}$, R$_{74}$ and R$_{75}$ are each independently a covalent bond, a lower alkyl, an alkoxy, an aryl or an arylalkoxy, as defined herein.

"Organic acid" refers to compound having at least one carbon atom and one or more functional groups capable of releasing a proton to a basic group. The organic acid preferably contains a carboxyl, a sulfonic acid or a phosphoric acid moiety. Exemplary organic acids include acetic acid, benzoic acid, citric acid, camphorsulfonic acid, methanesulfonic acid, taurocholic acid, chlordronic acid, glyphosphate and medronic acid.

"Inorganic acid" refers to a compound that does not contain at least one carbon atom and is capable of releasing a proton to a basic group. Exemplary inorganic acids include hydrochloric acid, sulfuric acid, nitric acid and phosphoric acid.

"Organic base" refers to a carbon containing compound having one or more functional groups capable of accepting a proton from an acid group. The organic base preferably contains an amine group. Exemplary organic bases include triethylamine, benzyldiethylamine, dimethylethyl amine, imidazole, pyridine and pipyridine.

"Independently selected" groups are groups present in the same structure that need not all represent the same substitution. For example, where two substituents are represented as $NOR_A$ and each $R_A$ is said to be independently selected from H, methyl, ethyl, etc., this means that where one $R_A$ is methyl, the other $R_A$ may be methyl but could be H or ethyl (or any other recited substitution).

Some of the compounds for use in the methods of the present invention may contain one or more chiral centers and therefore may exist in enantiomeric and diastereomeric forms. The scope of the present invention is intended to cover use of all isomers per se, as well as mixtures of cis and trans isomers, mixtures of diastereomers and racemic mixtures of enantiomers (optical isomers) as well. Further, it is possible using well known techniques to separate the various forms, and some embodiments of the invention may feature purified or enriched species of a given enantiomer or diastereomer.

A "pharmacological composition" refers to a mixture of one or more of the compounds described herein, or pharmaceutically acceptable salts thereof, with other chemical components, such as pharmaceutically acceptable carriers and/or excipients. The purpose of a pharmacological composition is to facilitate administration of a compound to an organism.

The phrase "pharmaceutically acceptable carrier" as used herein means a pharmaceutically-acceptable material, composition or vehicle, such as a liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. A physiologically acceptable carrier should not cause significant irritation to an organism and does not abrogate the biological activity and properties of the administered compound.

A "solvate" is a complex formed by the combination of a solute (e.g., a metalloprotease inhibitor) and a solvent (e.g., water). See J. Honig et al., The Van Nostrand Chemist's Dictionary, p. 650 (1953).

The terms "optical isomer", "geometric isomer" (e.g., a cis and/or trans isomer), "stereoisomer", and "diastereomer" have the accepted meanings (see, e.g., Hawley's Condensed Chemical Dictionary, 11th Ed.). The illustration of specific protected forms and other derivatives of the compounds of the instant invention is not intended to be limiting. The application of other useful protecting groups, salt forms, prodrugs etc., is within the ability of the skilled artisan.

A "prodrug" is a form of a drug that must undergo chemical conversion by metabolic processes before becoming an active, or fully active, pharmacological agent. A prodrug is not active, or is less active, in its ingested or absorbed or otherwise administered form. For example, a prodrug may be broken down by bacteria in the digestive system into products, at least one of which will become active as a drug. Alternatively, it may be administered systemically, such as by intravenous injection, and subsequently be metabolized into one or more active molecules.

DETAILED DESCRIPTION OF THE INVENTION

In accordance with the present invention, small molecule ligands are capable of reversibly binding non-covalently to the opsin protein and inhibiting the binding of 11-cis-retinal, to an opsin retinal binding pocket. Such interference with retinal binding reduces the formation of visual cycle products, such as all-trans-retinal, and thereby inhibits the production of compounds such as lipofuscin and A2E with resulting reduced risk and occurrence of toxicity that can result from accumulation of these substances. Such compounds, acting as pharmacologic chaperones, are also able to facilitate the proper folding and trafficking of mutant opsins associated with RP. Additionally, by inhibiting 11-cis-retinal binding and rhodopsin formation, the excessive stimulation and resulting activation of rhodopsin caused by exposure of the retina to bright light especially during retinal surgery reduces photocell death.

Certain synthetic retinoids (compounds structurally related to retinol (Vitamin A alcohol)) have been reported to bind to opsin. In the embodiments of the present invention, non-retinoid small molecules (compounds having a molecular weight less than about 1000 daltons, less than 800, less than 600, less than 500, less than 400, or less than about 300 daltons) have been found to bind to opsin.

The invention features compositions and methods that are useful for reducing formation of visual cycle products and toxicity associated with the accumulation of such products in vivo, reducing the probability of apoptotic events associated with excessive rhodopsin activation as well as preventing rod cell death due to aberrant processing and trafficking of mutant opsin proteins associated with RP.

Mislocalization of photoreceptor cell visual pigment proteins (opsins) can occur in various ocular diseases, and also with normal aging. In such cases the accumulation of mislocalized opsin leads to the decline in viability of photoreceptor cells. With time this mislocalized opsin accumulation leads to rod and cone cell death, retinal degeneration, and loss of vision.

In one aspect, the invention provides a method of correcting mislocalized opsin within a photoreceptor cell, comprising contacting a mislocalized opsin protein with an opsin-binding agent that binds reversibly and/or non-covalently to said mislocalized opsin protein, thereby promoting correct intracellular processing and transport of said opsin protein. Such opsin-binding agent is referred to as a "Productive Chaperone."

Such correction of mislocalization reduces photoreceptor cell stress, preventing photoreceptor cell decline in viability and death in various diseases of vision loss, and in normal age-related decline in dim-light and peripheral rod-mediated vision, central cone-mediated vision, and loss of night vision.

In another aspect of the invention, the opsin-binding agent promotes the degradation of the mislocalized opsin protein. This type of opsin-binding agent is referred to as a "Counterproductive", Shipwreck", or "Destructive Chaperone."

Enhancing the degradation of the mislocalized opsin by such an agent reduces the amount of mislocalized protein, thereby relieving photoreceptor cell stress, preventing decline in viability and death of photoreceptor cells in diseases of vision loss, as well as in normal age-related decline in dim-light and peripheral rod-mediated vision, central cone-mediated vision, and loss of night vision.

In embodiments of the foregoing, the ocular protein mislocalization disorder is one or more of wet or dry form of macular degeneration, retinitis pigmentosa, a retinal or macular dystrophy, Stargardt's disease, Sorsby's dystrophy, autosomal dominant drusen, Best's dystrophy, peripherin mutation associate with macular dystrophy, dominant form of Stargart's disease, North Carolina macular dystrophy, light toxicity, retinitis pigmentosa, normal vision loss related aging and normal loss of night vision related to aging.

Opsin, the GPCR (G-protein coupled receptor) responsible for vision, readily regenerates with 11-cis-retinal to form the visual pigment rhodopsin. The pigment is generated by formation of a protonated Schiff base between the aldehyde group of 11-cis-retinal and the ε-amino group of L-lysine in opsin (Matsumoto and Yoshizawa, Nature 1975 Dec. 11; 258(5535):523-6).

Thus, the present invention provides compositions and methods of use of small molecule compounds that bind to wild type and mutant opsins and compete with, or other wise prevent, 11-cis-retinal from combining with opsin to form rhodopsin and thereby inhibit formation of 11-cis-retinal and other visual cycle products.

In one embodiment, the invention provides opsin binding ligands of Formula I and pharmaceutically acceptable salts thereof:

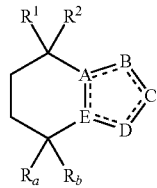

Formula I wherein $R^1$ and $R^2$ are independently:
1) hydrogen,
2) —$CH_3$, or
3) —$CH_2CH_3$;
$R_a$ and $R_b$ are each independently:
1) hydrogen,
2) —$CH_3$, or
3) —$CH_2CH_3$;
A═B═C═D═E is:
1) C(H)—C(═O)—C($R^{3'}$)═C($R^4$)—C($R^3$),
2) C(H)—C(═N—$OR^5$)C($R^{3'}$)═C($R^4$)—C($R^3$),
3) C(H)—C(H)($OR^5$)—C($R^{3'}$)═C($R^4$)—C($R^3$),
4) C(H)—C(═O)—C(H)($R^{3'}$)—C(H)($R^4$)—C($R^3$),
5) C(H)—C(═N—$OR^5$)—C(H)($R^{3'}$)—C(H)($R^4$)—C($R^3$),
6) C(H)—C(H)($OR^5$)—C(H)($R^{3'}$)—C(H)($R^4$)—C($R^3$),
7) C(H)—$CH_2$—C(═O)—N($R^4$)—C($R^3$),
8) C(H)—$CH_2$—C(═O)—O—C($R^3$),
9) C(H)—C(H)($R^{3'}$)—C(H)($R^4$)—C(═O)—C($R^3$),
10) C(H)—$CH_2$—$CH_2$—C(═N—$OR^5$)—C($R^3$),
11) C═C($R^4$)—C(═O)—C($R^{3'}$)($R^{4'}$)—C($R^3$),
12) C═C($R^4$)—C(═N—$OR^5$)—C($R^{3'}$)($R^{4'}$)—C($R^3$),
13) C═C($R^4$)—C(H)($OR^5$)—C($R^{3'}$)($R^{4'}$)—C($R^3$),
14) C(H)—$CH_2$—C($R^6$)═C(H)—C($R^3$),
15) C(H)—$CH_2$—C($R^6$)—C(H)($R^7$)—C($R^3$),
16) C(H)—C(═O)—C($R^{3'}$)($R^4$)—C($R^4$)($R^{5'}$)—C($R^3$),
17) C(H)—C(H)($OR^5$)—C($R^{3'}$)($R^4$)—C($R^4$)($R^{5'}$)—C($R^3$),
18) C(H)—C(═O)—N($R^4$)—$CH_2$—C($R^3$),
19) C(H)—C($R^{3'}$)($R^5$)—C(═O)—C($R^4$)═C,
20) C(H)—C($R^{3'}$)($R^5$)—C(═N—$OR^5$)—C($R^4$)═C,
21) C(H)—C($R^{3'}$)($R^5$)—C(H)($OR^5$)—C($R^4$)═C,
22) C(H)—C($R^{3'}$)($R^5$)—C(═O)—C($R^4$)($R^3$)—C($R^{4'}$),
23) C(H)—C($R^{3'}$)($R^5$)—C(═N—$OR^5$)—C($R^4$)($R^3$)—C($R^{4'}$),
24) C(H)—C($R^{3'}$)($R^5$)—C(H)($OR^5$)—C($R^4$)($R^3$)—C($R^{4'}$),
25) /═C—C(═O)—N($R^4$)—C($R^{3'}$)($R^5$)—C═/,
26) C(H)—C($R^{3'}$)($R^5$)—C($R^4$)($R^3$)—C(H)($OR^5$)—C($R^{4'}$),
27) C(H)—C(═N—$OR^5$)—C($R^{3'}$)($R^4$)—C($R^4$)($R^{5'}$)—C($R^3$), or
28) /═C—C($R^{3'}$)($R^5$)—C($R^4$)($R^{5'}$)—C(O)—C═/,
29) C(H)—C($R^{3'}$)═C($R^4$)—C(O)—C($R^3$), or
30) C(H)—C($R^{3'}$)═C($R^4$)—C(H)($OR^5$)—C($R^3$);
wherein /═ preceding A and ═/ following E are meant to denote a double bond between A and E.
$R^3$, $R^{3'}$, $R^5$ and $R^{5'}$ are each independently:
1) hydrogen, or
2) lower alkyl;
$R^4$ and $R^{4'}$ are each independently:
1) hydrogen,
2) lower alkyl,
3) cycloalkyl, or
4) phenyl;
$R^6$ is:
1) —$CO_2CH_3$,
2) —$CONR^5R^{5'}$, or
3) —$CH^2OR^5$;
$R^7$ is:
1) hydrogen, or
2) —$OR^5$;
with the proviso that if either $R^1$ or $R^2$ are selected as hydrogen then $R_a$ and $R_b$ must be selected as methyl or ethyl.

In preferred embodiments, the compound has the structure of Formula I wherein A═B═C═D═E is C═C($R^4$)—C(═O)—C($R^{3'}$)($R^{4'}$)—C($R^3$) and $R^3$, $R^{3'}$, $R^4$ and $R^{4'}$ are each independently hydrogen or lower alkyl or more preferably are each independently hydrogen or methyl and most preferably $R^3$, $R^{3'}$, $R^4$ and $R^{4'}$ are hydrogen. In other preferred embodiments, $R^1$ and $R^2$ are each independently methyl or ethyl and $R_a$ and $R_b$ are each independently hydrogen or methyl or more preferably $R^1$ and $R^2$ are methyl and $R_a$ and $R_b$ are each independently hydrogen or methyl, and most preferably $R^1$ and $R^2$ are methyl and $R_a$ and $R_b$ are hydrogen.

In preferred embodiments of compounds of Formula I, lower alkyl is methyl or ethyl, most preferably methyl.

In other preferred embodiments, the compound has the structure of Formula I wherein A═B═C═D═E is C═C($R^4$)—C(═O)—C($R^{3'}$)($R^{4'}$)—C($R^3$) and $R^3$, $R^{3'}$, $R^4$ and $R^{4'}$ are each independently hydrogen or lower alkyl or more preferably are each independently hydrogen or methyl, and most preferably $R^3$, $R^{3'}$ and $R^4$ are hydrogen and $R^{4'}$ is lower alkyl or methyl. In other preferred embodiments $R^1$ and $R^2$ are each independently methyl or ethyl and $R_a$ and $R_b$ are each independently hydrogen or methyl or, more preferably, $R^1$ and $R^2$ are methyl and $R_a$ and $R_b$ are each independently hydrogen or methyl, and most preferably $R^1$ and $R^2$ are both methyl and $R_a$ and $R_b$ are both hydrogen.

In other preferred embodiments, the compound has the structure of Formula I wherein A═B═C═D═E is C═C($R^4$)—C(═O)—C($R^{3'}$)($R^{4'}$)—C($R^3$) and $R^3$, $R^{3'}$, $R^4$ and $R^{4'}$ are each independently hydrogen or lower alkyl or more preferably are each independently hydrogen or methyl, and most preferably wherein $R^3$, $R^{3'}$, $R^4$ and $R^{4'}$ are hydrogen. In other preferred embodiments, $R^1$ and $R^2$ are methyl or ethyl and $R_a$ and $R_b$ are hydrogen or methyl or preferably $R^1$ and $R^2$ are methyl and $R_a$ and $R_b$ are hydrogen or methyl, and most preferably $R^1$, $R^2$, $R_a$ and $R_b$ are each methyl.

In other preferred embodiments, the compound has the structure of Formula I wherein A═B═C═D═E is C(H)—C(═O)—C($R^3$)═C($R^4$)—C($R^3$) and $R^3$, $R^{3'}$, $R^4$ and are hydrogen or lower alkyl, or more preferably are each independently hydrogen or methyl, or most preferably $R^3$ is hydrogen and $R^{3'}$ and $R^4$ are methyl. In other preferred embodiments, $R^1$ and $R^2$ are each independently hydrogen or methyl and $R_a$ and $R_b$ are each independently methyl or ethyl, or more preferably $R^1$ and $R^2$ are each independently hydrogen and $R_a$ and $R_b$ are each independently methyl or ethyl, and most preferably $R^1$ and $R^2$ are each hydrogen and $R_a$ and $R_b$ are each methyl.

In other preferred embodiments, the compound has the structure of Formula I wherein A═B═C═D═E is C(H)—C($R^3$)($R^5$)—C(H)(O$R^5$)—C($R^4$)($R^3$)—C($R^4$) and $R^3$, $R^{3'}$, $R^4$, $R^{4'}$, $R^5$ and $R^{5'}$ are hydrogen or lower alkyl more preferably hydrogen or methyl most preferably $R^3$, $R^{3'}$, $R^4$, $R^5$ and $R^{5'}$ are hydrogen and $R^{4'}$ is methyl. In other preferred examples, $R^1$ and $R^2$ are each independently methyl or ethyl and $R_a$ and $R_b$ are each independently hydrogen or methyl, or more preferably $R^1$ and $R^2$ are each independently methyl and $R_a$ and $R_b$ are each independently hydrogen or methyl, or most preferably $R^1$ and $R^2$ are methyl and $R_a$ and $R_b$ are hydrogen.

In other preferred embodiments, the compound has the structure of Formula I wherein A═B═C═D═E is C(H)—C($R^{3'}$)($R^5$)—C(═N—O$R^{5'}$)—C($R^4$)($R^3$)—C($R^{4'}$) and $R^3$, $R^{3'}$, $R^4$, $R^{4'}$, $R^5$ and $R^{5'}$ are hydrogen or lower alkyl, or more preferably hydrogen or methyl, and most preferably $R^3$, $R^{3'}$, $R^4$, $R^5$ and $R^{5'}$ are hydrogen and $R^{4'}$ is methyl. In other preferred embodiments, $R^1$ and $R^2$ are each independently methyl or ethyl and $R_a$ and $R_b$ are each independently hydrogen or methyl, or more preferably $R^1$ and $R^2$ are methyl and $R_a$ and $R_b$ are each independently hydrogen or methyl, and most preferably $R^1$ and $R^2$ are methyl and $R_a$ and $R_b$ are hydrogen.

In other preferred embodiments, the compound has the structure of Formula I wherein A═B═C═D═E is C(H)—C(H)(O$R^5$)—C($R^3$)═C($R^4$)—C($R^3$) and $R^3$, $R^{3'}$, $R^4$ and $R^5$ are each independently hydrogen or lower alkyl, or more preferably are each independently hydrogen or methyl, or most preferably $R^3$, $R^{3'}$, $R^4$ are methyl and $R^5$ is hydrogen. In other preferred embodiments, $R^1$ and $R^2$ are each independently methyl or ethyl and $R_a$ and $R_b$ are each independently hydrogen or methyl, or more preferably $R^1$ and $R^2$ are methyl and $R_a$ and $R_b$ are each independently hydrogen or methyl, or most preferably $R^1$ and $R^2$ are methyl and $R_a$ and $R_b$ are hydrogen.

In yet other preferred embodiments, the compound has the structure of Formula I wherein A═B═C═D═E is C(H)—C(H)(O$R^5$)—C(H)($R^3$)—C(H)($R^4$)—C($R^3$) and $R^3$, $R^{3'}$, $R^4$ and $R^5$ are each independently hydrogen or lower alkyl, or more preferably are each independently hydrogen or methyl, and most preferably $R^{3'}$, $R^4$ and $R^5$ are hydrogen and $R^3$ is methyl. In other preferred embodiments, $R^1$ and $R^2$ are each independently methyl or ethyl and $R_a$ and $R_b$ are each independently hydrogen or methyl, or more preferably $R^1$ and $R^2$ are methyl and $R_a$ and $R_b$ are each independently hydrogen or methyl, or most preferably $R^1$ and $R^2$ are methyl and $R_a$ and $R_b$ are hydrogen.

In yet other preferred embodiments, the compound has the structure of Formula I wherein A═B═C═D═E is C(H)—C($R^3$)($R^5$)—C(═O)—C($R^4$)($R^3$)—C($R^4$) and $R^3$, $R^{3'}$, $R^4$, $R^{4'}$ and $R^5$ are each independently hydrogen or lower alkyl, or more preferably are each independently hydrogen or methyl, and most preferably $R^3$, $R^{3'}$, $R^4$, $R^{4'}$ and $R^5$ are hydrogen. In other preferred embodiments, $R^1$ and $R^2$ are each independently methyl or ethyl and $R_a$ and $R_b$ are each independently hydrogen or methyl, or more preferably $R^1$ and $R^2$ are methyl and $R_a$ and $R_b$ are each independently hydrogen or methyl, or most preferably $R^1$, $R^2$, $R_a$ and $R_b$ are methyl.

In preferred examples of the invention, the compound has the structure of Formula I wherein $R^1$ and $R^2$ are both methyl and $R_a$ and $R_b$ are both hydrogen, or where $R^1$ and $R^2$ are both hydrogen and $R_a$ and $R_b$ are both methyl or where $R^1$, $R^2$, $R_a$ and $R_b$ are all methyl.

In another embodiment, the invention provides opsin binding ligands of Formula (II) and pharmaceutically acceptable salts thereof:

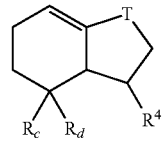

Formula II wherein T is:
1) C(═O),
2) C(H)(O$R^5$), or
3) C(═N—O$R^5$);
$R_c$ and $R_d$ are each independently:
1) —CH$_3$, or
2) —CH$_2$CH$_3$;
and $R^4$ is as defined herein.

In preferred embodiments, the compound has the structure of Formula II wherein T is C(═O) or C(═N—O$R^5$) and $R^4$ is lower alkyl, and $R_c$ and $R_d$ are methyl or ethyl or more preferably wherein T is C(═O) and $R_c$ and $R_d$ are both methyl and most preferably wherein $R^4$ is methyl.

In specific embodiments the opsin binding compound of Formula I is (wherein each compound number corresponds to the number of the example where it was prepared):
(±)-(3aR,7aS)-3,3a,7,7-tetramethyl-3a,4,5,6,7,7a-hexahydro-1H-inden-1-one (Compound 1);
(±)-(3aS,7aR)-4,4-dimethylhexahydro-1H-indol-2(3H)-one (Compound 2);
(±)-(3aS,7aS)-4,4,7,7-tetramethylhexahydrobenzofuran-2 (3H)-one (Compound 3);
(±)-(3aS,7aR)-1,4,4-trimethylhexahydro-1H-indol-2(3H)-one (Compound 4);
(±)-(3aS,7aR)-4,4,7a-trimethyloctahydro-1H-inden-1-one (Compound 5);

4,4,7a-trimethyl-5,6,7,7a-tetrahydro-1H-inden-2(4H)-one (Compound 6);
4,4-dimethylhexahydrobenzofuran-2(3H)-one (Compound 7);
(±)-(3aS,7aS)-methyl 3a,7,7-trimethyl-3a,4,5,6,7,7a-hexahydro-1H-indene-2-carboxylate (Compound 8);
(±)-(3R,3aS,7aS)-3,3a,7,7-tetramethyloctahydro-1H-inden-1-one (Compound 9);
4,4,7a-trimethyl-2,4,5,6,7,7a-hexahydro-1H-inden-2-ol (Compound 10);
2-methoxy-4,4,7a-trimethyl-2,4,5,6,7,7a-hexahydro-1H-indene (Compound 11);
7,7-dimethyl-2,3,4,5,6,7-hexahydro-1H-isoindol-1-one (Compound 12);
2,7,7-trimethyl-2,3,4,5,6,7-hexahydro-1H-isoindol-1-one (Compound 13);
(±)-(3aR,7aS)-3,3a,7,7-tetramethyl-3a,4,5,6,7,7a-hexahydro-1H-inden-1-one oxime (Compound 14);
(±)-(1S,3aR,7aS)-3,3a,7,7-tetramethyl-3a,4,5,6,7,7a-hexahydro-1H-inden-1-ol (Compound 15);
(±)-(3R,3aS,7aS)-3,3a,7,7-tetramethyloctahydro-1H-inden-1-one oxime (Compound 16);
7,7-dimethyloctahydro-1H-isoindol-1-one (Compound 17);
(±)-(1S,3aS,7aR)-4,4,7a-trimethyloctahydro-1H-inden-1-ol (Compound 18);
(±)-(3aR,7aS)-3,3a,7,7-tetramethyl-3a,4,5,6,7,7a-hexahydro-1H-inden-1-one O-methyl oxime (Compound 19);
(±)-(1R,7aS)-1,4,4,7a-tetramethyl-5,6,7,7a-tetrahydro-1H-inden-2(4H)-one (Compound 20);
1,1,4,4,7a-pentamethyl-5,6,7,7a-tetrahydro-1H-inden-2(4H)-one (Compound 21);
(±)-((3aS,7aS)-3a,7,7-trimethyl-3a,4,5,6,7,7a-hexahydro-1H-inden-2-yl)methanol (Compound 22);
(±)-(3aS,7aS)-2-(methoxymethyl)-3a,7,7-trimethyl-3a,4,5,6,7,7a-hexahydro-1H-indene (Compound 23);
(±)-(1S,3aS,7aR)-1-methoxy-4,4,7a-trimethyloctahydro-1H-indene (Compound 24);
(±)-(3aS,7aS)-methyl 3a,7,7-trimethyloctahydro-1H-indene-2-carboxylate (Compound 25);
(±)-((3aS,7aS)-3a,7,7-trimethyloctahydro-1H-inden-2-yl)methanol (Compound 26);
7,7-dimethyl-5,6,7,7a-tetrahydro-1H-inden-2(4H)-one (Compound 27);
(±)-(3aR,7aS)-3a,7,7-trimethyl-3-phenyl-3a,4,5,6,7,7a-hexahydro-1H-inden-1-one (Compound 28);
(±)-(3aR,7aS)-3-isopropyl-3a,7,7-trimethyl-3a,4,5,6,7,7a-hexahydro-1H-inden-1-one (Compound 29);
4,4,7a-trimethyl-5,6,7,7a-tetrahydro-1H-inden-2(4H)-one oxime (Compound 30);
4,4,7a-trimethyl-5,6,7,7a-tetrahydro-1H-inden-2(4H)-one O-methyl oxime (Compound 31);
(±)-(3R,3aS,7aS)-3,3a,7,7-tetramethyloctahydro-1H-inden-1-ol (Compound 32);
(±)-(3aS,7aR)-4,4,7a-trimethyloctahydro-1H-inden-1-one oxime (Compound 33);
(±)-(3aR,7aS)-3-ethyl-3a,7,7-trimethyl-3a,4,5,6,7,7a-hexahydro-1H-inden-1-one (Compound 34);
(±)-(3aS,7aS)-3a,7,7-trimethyl-3a,4,5,6,7,7a-hexahydro-1H-inden-1-one (Compound 35);
(±)-(1S,3aS,7aS)-3a,7,7-trimethyl-3a,4,5,6,7,7a-hexahydro-1H-inden-1-ol (Compound 36);
(±)-(1R,3aS,7aS)-3a,7,7-trimethyl-3a,4,5,6,7,7a-hexahydro-1H-inden-1-ol (Compound 37);
(±)-(1S,2R,3aS,7aR)-2-(hydroxymethyl)-4,4,7a-trimethyl-octahydro-1H-inden-1-ol (Compound 38);
(±)-(1S,2S,3aS,7aR)-2-(hydroxymethyl)-4,4,7a-trimethyl-octahydro-1H-inden-1-ol (Compound 39);

(±)-(3aS,7aS)-3a,7,7-trimethylhexahydro-1H-inden-2(3H)-one (Compound 40);
4,4,7,7-tetramethyl-5,6,7,7a-tetrahydro-1H-inden-2(4H)-one (Compound 41);
(±)-(3aS,7aS)-3a,7,7-trimethyl-3a,4,5,6,7,7a-hexahydro-1H-indene-2-carboxamide (Compound 42);
(±)-(3aR,7aS)-3-tert-butyl-3a,7,7-trimethyl-3a,4,5,6,7,7a-hexahydro-1H-inden-1-one (Compound 43);
(±)-(3aR,7aS)-3-cyclopropyl-3a,7,7-trimethyl-3a,4,5,6,7,7a-hexahydro-1H-inden-1-one (Compound 44);
(±)-(3aR,7aS)-3-isopropyl-3a,7,7-trimethyl-3a,4,5,6,7,7a-hexahydro-1H-inden-1-one oxime (Compound 45);
(±)-(3S,3aS,7aS)-3-isopropyl-3a,7,7-trimethyloctahydro-1H-inden-1-one (Compound 46);
(±)-(1S,3aR,7aS)-3-isopropyl-3a,7,7-trimethyl-3a,4,5,6,7,7a-hexahydro-1H-inden-1-ol (Compound 47);
(±)-(3S,3aS,7aS)-3-isopropyl-3a,7,7-trimethyloctahydro-1H-inden-1-one O-methyl oxime (Compound 48);
(±)-(3aS,7aS)-3a,7,7-trimethyloctahydro-1H-indene-2-carboxamide (Compound 49);
(±)-(1R,3S,3aS,7aS)-3-isopropyl-3a,7,7-trimethyloctahydro-1H-inden-1-ol (Compound 50);
(±)-(3aR,7aS)-3-isopropyl-3a,7,7-trimethyl-3a,4,5,6,7,7a-hexahydro-1H-inden-1-one O-methyl oxime (Compound 51);
(±)-(3S,3aS,7aS)-3-isopropyl-3a,7,7-trimethyloctahydro-1H-inden-1-one oxime (Compound 52);
4,4-dimethyl-5,6,7,7a-tetrahydro-1H-inden-2(4H)-one (Compound 53);
4,4-dimethylhexahydro-1H-inden-2(3H)-one (Compound 54);
4,4-dimethylhexahydro-1H-inden-2(3H)-one oxime (Compound 55);
4,4-dimethyl-2,3,4,5,6,7-hexahydro-1H-inden-1-one (Compound 56);
(±)-(3aS,7aS)-2-(methoxymethyl)-3a,7,7-trimethyloctahydro-1H-indene (Compound 57);
(±)-(1S,3S,3aS,7aS)-3-isopropyl-3a,7,7-trimethyloctahydro-1H-inden-1-ol (Compound 58);
(±)-(3aS,7aS)-3a,7,7-trimethyloctahydro-1H-inden-1-one (Compound 59);
(±)-(1S,3aS,7aS)-3a,7,7-trimethyloctahydro-1H-inden-1-ol (Compound 60);
(±)-(1R,7aS)-1-isopropyl-4,4-dimethyl-5,6,7,7a-tetrahydro-1H-inden-2(4H)-one (Compound 61);
(±)-(3aS,7aS)-3a,7,7-trimethylhexahydro-1H-inden-2(3H)-one oxime (Compound 62);
(±)-(3aS,7aS)-3a,7,7-trimethyloctahydro-1H-inden-2-ol (Compound 63);
(±)-(3aS,7aS)-2,3,4,4-tetramethyl-3a,4,5,6,7,7a-hexahydro-1H-inden-1-one (Compound 64);
(±)-(3aR,7aS)-2,3,3a,7,7-pentamethyl-3a,4,5,6,7,7a-hexahydro-1H-inden-1-one (Compound 65);
(±)-(1R,3aR,7aS)-2,3,3a,7,7-pentamethyl-3a,4,5,6,7,7a-hexahydro 1H inden-1-ol (Compound 66);
(±)-(1R,7aS)-1,4,4-trimethyl-5,6,7,7a-tetrahydro-1H-inden-2(4H)-one (Compound 67);
(±)-(1R,3aS,7aS)-3a,7,7-trimethyloctahydro-1H-inden-1-ol (Compound 68);
(+)-4,4,7,7-tetramethyl-5,6,7,7a-tetrahydro-1H-inden-2(4H)-one (Compound 69a);
(−)-4,4,7,7-tetramethyl-5,6,7,7a-tetrahydro-1H-inden-2(4H)-one (Compound 69b);
(3aR,7aS) and (3aS,7aR)-4,4,7,7-tetramethylhexahydro-1H-inden-2(3H)-one (Compound 70);
(±)-(3R,3aR)-3,4,4-trimethyl-2,3,3a,4,5,6-hexahydro-1H-inden-1-one (Compound 71);

(±)-(1S,3aS,7aS)-2,3,4,4-tetramethyl-3a,4,5,6,7,7a-hexahydro-1H-inden-1-ol (Compound 72);
(±)-(3aS,7aS)-2,3,4,4-tetramethyloctahydro-1H-inden-1-one (Compound 73);
(±)-(3R,3aS,7aR)-3,7,7-trimethyloctahydro-1H-inden-1-one (Compound 74);
7a-ethyl-4,4-dimethyl-5,6,7,7a-tetrahydro-1H-inden-2(4H)-one (Compound 75);
(±)-(1R,7aS)-1-ethyl-4,4,7a-trimethyl-5,6,7,7a-tetrahydro-1H-inden-2(4H)-one (Compound 76);
(±)-(3aR,7aS)-4,4,7,7-tetramethyloctahydro-1H-inden-2-ol (Compound 77);
4,4,7,7-tetramethyl-5,6,7,7a-tetrahydro-1H-inden-2(4H)-one oxime (Compound 78);
(±)-(3aR,7aS)-4,4,7,7-tetramethylhexahydro-1H-inden-2(3H)-one oxime (Compound 79)
including all pharmaceutically acceptable salts, hydrates, or solvates thereof.

All compound names were derived using ChemBioDraw 11.0.1.

The present invention does not include the following compounds (as represented by their indicated CAS registry numbers) as novel compositions of matter (but are claimed for use in the methods of the invention) and are referred to herein as the Excluded Compound Group: 1322705-86-1, 1217498-30-0, 917392-28-0, 901132-06-7, 678160-04-8, 531512-99-9, 531512-94-4, 531512-91-1, 531512-87-5, 531512-85-3, 531512-83-1, 531512-76-2, 334826-84-5, 226546-70-9, 170081-07-9, 165402-62-0, 108613-26-9, 101098-92-4, 75824-85-0, 75824-83-8, 75824-82-7, 75824-78-1, 70006-17-6, 55085-49-9, 42741-51-5, 38881-23-1, 35076-54-1, 31089-96-0, 31089-92-6, 28102-31-0, 28102-26-3, 28102-23-0, 1258783-39-9, 155501-25-0, 104641-34-1, 104640-83-7, 104527-56-2, 87220-77-7, 71075-17-7, 38725-47-2, 37531-06-9, 24739-75-1, 16778-27-1, 136771-91-0, 136771-90-9 and 369366-32-5.

The Excluded Compound Group contains any and all of the compounds in the preceding list as identified by their indicated CAS (Chemical Abstracts Service) numbers.

Thus, the novel compounds and/or compositions of matter of the invention are compounds of Formula I (including their indicated substituent identities) but do not include compounds of the Excluded Compound Group.

However, the methods of the present invention employ any compounds of Formula I (including their indicated substituent identities) but do not exclude use of compounds of the Excluded Compound Group.

Especially preferred examples of the compounds of the invention, and methods using said compounds, include compounds selected from one or more of the group consisting of compounds 8, 13, 14, 16, 20, 22, 26, 27, 29, 30, 33, 34, 36, 37, 41, 44, 45, 46, 53, 55, 58, 60, 62, 63, 64, 66, 67, 69a, 70, 71 and 72 including all pharmaceutically acceptable salts, solvates and hydrates thereof.

Another embodiment of the invention provides the opsin binding ligand metabolites of the opsin binding compounds. These metabolites, include but are not limited to, degradation products, hydrolysis products, gluconoride adducts and the like, of the opsin binding compounds and pharmaceutically acceptable salts thereof, of the opsin compounds.

Another embodiment of the invention provides processes for making the novel compounds of the invention and to the intermediates useful in such processes. The reactions are performed in solvents appropriate to the reagents and materials used are suitable for the transformations being effected. It is understood by one skilled in the art of organic synthesis that the functionality present in the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to one skilled in the art. The use of sulfur, nitrogen and oxygen protecting groups is well known for protecting thiol, amino and alcohol groups against undesirable reactions during a synthetic procedure and many such protecting groups are known and described by, for example, Greene and Wuts, *Protective Groups in Organic Synthesis*, Third Edition, John Wiley & Sons, New York (1999).

Compounds of the invention that have one or more asymmetric carbon atoms may exist as the optically pure enantiomers, pure diastereomers, mixtures of enantiomers, mixtures of diastereomers, racemic mixtures of enantiomers, diasteromeric racemates or mixtures of diastereomeric racemates. It is to be understood that the invention anticipates and includes within its scope all such isomers and mixtures thereof.

The chemical reactions described herein are generally disclosed in terms of their broadest application to the preparation of the compounds of this invention. Occasionally, the reactions may not be applicable as described to each compound included within the disclosed scope. The compounds for which this occurs will be readily recognized by one skilled in the art. In all such cases, either the reactions can be successfully performed by conventional modifications known to one skilled in the art, e.g., by appropriate protection of interfering groups, by changing to alternative conventional reagents, by routine modification of reaction conditions, or other reactions disclosed herein or otherwise conventional, will be applicable to the preparation of the corresponding compounds of this invention. In all preparative methods, all starting materials are known or readily prepared from known starting materials.

METHODS OF THE INVENTION

The present invention provides a method of using compounds of the Formula I for reducing the formation of toxic visual cycle products, comprising contacting an opsin protein with small molecule ligands that reversibly bind to said opsin protein to inhibit 11-cis-retinal binding in said binding pocket, thereby reducing formation of toxic visual cycle products associated with wet or dry ARMD and reducing photocell apoptosis associated with excessive rhodopsin activation as a result of bright light stimulation.

The present invention also provides a method of use of compounds of the Formula I for treating, preventing or reducing the risk of light toxicity in a mammal, comprising administering to a mammal, at risk of developing an ophthalmic condition that is related to the formation or accumulation of a visual cycle product or apoptotic photocell death.

The present invention also provides a method of use of compounds of the Formula I for treating, preventing or reducing the risk of light toxicity in a mammal, comprising administering to a mammal, at risk of developing an ophthalmic condition that is related to the formation or accumulation of a visual cycle product or apoptotic photocell death, an effective amount of a that small molecule ligand that reversibly binds (for example, at or near the retinal binding pocket) to an opsin protein present in the eye of said mammal, for example, to inhibit 11-cis-retinal binding in said binding pocket, thereby reducing light toxicity and photocell apoptosis.

The present invention also provides a method of use of compounds of the Formula I for treating, preventing or reducing the risk of RP in a mammal, comprising administering to a mammal, at risk of RP related to the improper folding and trafficking of mutant opsins, an effective amount of a that small molecule ligand that reversibly binds (for example, at or near the retinal binding pocket) to an opsin protein present in the eye of said mammal, for example, to inhibit 11-cis-retinal binding in said binding pocket, thereby reducing the vision loss caused by RP.

In specific examples of such methods, the small molecule ligand is selective for binding to opsin and/or the small molecule ligand binds to said opsin in the retinal binding pocket of said opsin protein and/or the small molecule ligand binds to said opsin protein so as to inhibit covalent binding of 11-cis-retinal to said opsin protein when said 11-cis-retinal is contacted with said opsin protein when said small molecule ligand is present and/or the mammal is a human being.

In one embodiment, light toxicity is related to an ophthalmic procedure, for example, ophthalmic surgery. Said agent may be administered prior to, during or after said surgery (or at any one or more of those times).

In specific embodiments of the methods of the invention, the native opsin protein is present in a cell, such as a rod cell, preferably, a mammalian and more preferably a human cell. In specific embodiments, the small molecule ligands of the invention inhibit binding of 11-cis-retinal in the binding pocket of opsin and slow the visual cycle thereby reducing the formation of all-trans-retinal, or a toxic visual cycle product formed from it, such as lipofuscin or N-retinylidene-N-retinylethanolamine (A2E). Alternatively, photocell apoptosis as a result of excessive rhodopsin activation is reduced or prevented by inhibition of rhodopsin formation. Additionally, improper folding and trafficking of mutant opsin proteins associated with RP is reduced.

In methods of the invention, administering is preferably by topical administration (such as with an eye wash) or by systemic administration (including oral, intraocular injection or periocular injection). By way of preferred example, the ophthalmic condition to be treated is light toxicity, such as that resulting from ocular surgery, for example, retinal or cataract surgery.

Also encompassed is an ophthalmologic composition comprising an effective amount of compounds of the Formula I in a pharmaceutically acceptable carrier, wherein said agent reversibly binds non-covalently (for example, at or near the retinal binding pocket) to said opsin protein to inhibit 11-cis-retinal binding in said pocket, preferably where the small molecule ligand is selective for opsin protein.

The present invention further provides a screening method for identifying a small molecule ligand that reduces light toxicity in a mammalian eye, comprising:
(a) contacting a native opsin-protein with a test compound in the presence of 11-cis-retinal and under conditions that promote the binding of the test compound and the 11-cis-retinal to the native opsin protein; and
(b) determining a reversible reduction in rate of formation of rhodopsin relative to the rate when said test compound is not present,
thereby identifying said test compound as a small molecule ligand that reduces light toxicity in a mammalian eye.

In a preferred embodiment, said test compound is structurally related to a compound disclosed herein.

The compounds of the Formula I may be administered along with other agents, including a mineral supplement, an anti-inflammatory agent, such as a steroid, for example, a corticosteroid, and/or an anti-oxidant. Among the corticosteroids useful for such administration are those selected from the group consisting of cortisone, hydrocortisone, prednisone, prednisolone, methylprednisolone, triamcinolone, betamethasone, beclamethasone and dexamethasone. Useful anti-oxidants include vitamin A, vitamin C and vitamin E.

The methods of the invention also contemplate reducing light toxicity by using at least one additional agent (in addition to the compounds of the Formula I selected from the group consisting of a proteasomal inhibitor, an autophagy inhibitor, a lysosomal inhibitor, an inhibitor of protein transport from the ER to the Golgi, an Hsp90 chaperone inhibitor, a heat shock response activator, a glycosidase inhibitor, and a histone deacetylase inhibitor, wherein the small molecule opsin binding and the additional compound are administered simultaneously or within fourteen days of each other in amounts sufficient to treat the subject.

In a particular example of the methods of the invention, the compounds of the Formula I and the additional compound are administered within ten days of each other, within five days of each other, within twenty-four hours of each other and preferably are administered simultaneously. In one example, the small molecule opsin binding and the additional compound are administered directly to the eye. Such administration may be intraocular or intravitrial. In other examples, the small molecule opsin binding and the additional compound are each incorporated into a composition that provides for their long-term release, such as where the composition is part of a microsphere, nanosphere, nano emulsion or implant.

As described herein, the compounds of the Formula I are useful in the methods of the invention are available for use alone or in combination with one or more additional compounds to treat or prevent conditions associated with excessive rhodopsin activation, such as light toxicity, for example, resulting from ocular surgical procedures. In one embodiment, compounds of the Formula I of the invention is administered without an additional active compound. In another embodiment, compounds of the Formula I of the invention is used in combination and with another active compound (e.g., as discussed herein). In still another exemplary embodiment, compounds of the Formula I are administered in combination with the proteasomal inhibitor MG132, the autophagy inhibitor 3-methyladenine, a lysosomal inhibitor ammonium chloride, the ER-Golgi transport inhibitor brefeldin A, the Hsp90 chaperone inhibitor Geldamycin, the heat shock response activator Celastrol, the glycosidase inhibitor, and the histone deacetylase inhibitor Scriptaid, can be used to reduce formation of visual cycle products and cell apoptosis as a result of excessive rhodopsin activation.

As described herein, the compounds of the Formula I are useful in the methods of the invention are available for use alone or in combination with one or more additional compounds to treat or prevent the aberrant processing and trafficking of mutant opsin proteins associated with rod cell death as a result of RP. In one embodiment, compounds of the Formula I of the invention is administered without an additional active compound. In another embodiment, compounds of the Formula I of the invention is used in combination and with another active compound (e.g., as discussed herein). In still another exemplary embodiment, compounds of the Formula I are administered in combination with the proteasomal inhibitor MG132, the autophagy inhibitor 3-methyladenine, a lysosomal inhibitor ammonium chloride, the ER-Golgi transport inhibitor brefeldin. A, the Hsp90 chaperone inhibitor Geldamycin, the heat shock response activator Celastrol, the glycosidase inhibitor, and the histone deacetylase inhibitor Scriptaid, can be used to reduce or prevent the rod cell death and resulting blindness associated with RP.

As described herein, the compounds of the Formula I are useful in the methods of the invention are available for use alone or in combination with one or more additional compounds to treat or prevent conditions associated with production and accumulation of toxic visual cycle products derived from all-trans-retinal, such as lipofucin and A2E, for example, the blindness associated with wet or dry ARMD. In one embodiment, compounds of the Formula I of the invention are administered without an additional active compound. In another embodiment, compounds of the Formula I of the invention are used in combination and with another active compound (e.g., as discussed herein). In still another exemplary embodiment, compounds of the Formula I are administered in combination with the proteasomal inhibitor MG132, the autophagy inhibitor 3-methyladenine, a lysosomal inhibitor ammonium chloride, the ER-Golgi transport inhibitor brefeldin A, the Hsp90 chaperone inhibitor Geldamycin, the heat shock response activator Celastrol, the glycosidase inhibitor, and the histone deacetylase inhibitor Scriptaid, can be used to reduce formation of toxic visual cycle product metabolites and photo cell death as a result of dry ARMD.

In a typical competition assay of the invention, a compound is sought that will tie up the retinal binding pocket of the opsin protein. Thus, the assay seeks to identify a small molecule opsin binding compound (one that will not be tightly regulated by the retina as to amount entering rod cells) that competes with or prevents 11-cis-retinal or 9-cis-retinal from forming rhodopsin or isorhodopsin. Over time, this will slow the rate of formation of rhodopsin relative to the rate when 11-cis-retinal alone is present. In one embodiment, the assay is conducted in the presence of 11-cis-retinal, and the rate of formation of rhodopsin is measured as a way of determining competition for the retinal binding pocket, for example, by determining the rate of increase in the 500 nm peak characteristic for rhodopsin. No antibodies for rhodopsin are required for this assay. A useful compound will exhibit a rate of rhodopsin formation that is at least about 2 to 5 fold lower than that observed in the presence of 11-cis-retinal when said test compound is not present.

In specific embodiments of the methods of the invention, the mis-folded opsin protein comprises a mutation in its amino acid sequence, for example, one of the mutations T17M, P347S, R135W or P23H, preferably P23H.

Preferably, in any of the methods of the invention, the opsin-binding agent binds to opsin in its retinal binding pocket.

In one aspect, the present invention provides a method of inhibiting the formation or accumulation of a visual cycle product, comprising contacting an opsin protein with a compound that reduces hydration of said opsin protein, preferably wherein said compound competes with one or more water molecules for binding to opsin. In specific embodiments of such methods, the compound binds chemically to the opsin protein, for example, through hydrogen bonding.

While use of any of the compounds disclosed herein as a means of reducing hydration in the opsin binding pocket should be considered a preferred embodiment of such method, the reduction of formation of a visual cycle product by reducing the formation of rhodopsin is a general method of the invention for reducing such visual cycle product formation, especially production of lipofuscin and/or A2E, and for treating an ophthalmic disease by reducing said hydration is a general aim of the invention and is not necessarily limited in scope only to the use of chemicals disclosed herein but may include use of other known or yet to be known chemical compounds so long as they function in the methods of the invention and reduce hydration (i.e., binding of water) in the retinal binding pocket of opsin.

It should be noted that the compounds disclosed herein for use in the methods of the invention may not function to reduce hydration in the retinal binding pocket of opsin but may still function in one or more of the methods of the invention. For example, a compound of Formula I may bind to an allosteric site on the protein thereby excluding retinal from the retinal binding site without necessarily decreasing hydration yet still reduce formation of a visual cycle product, such as lipofuscin and/or A2E, by virtue of its excluding retinal from the binding pocket, thus non-covalently reducing the activity of the visual cycle.

In embodiments of any of the compositions and methods of the invention, the opsin-binding agent (e.g., a non-retinoid binding agent) is selective for binding to opsin. Such selectivity is not to be taken as requiring exclusivity that said agent may bind to other proteins as well as to opsin but its binding to opsin will be at least selective, whereby the binding constant (or dissociation constant) for binding to opsin will be lower than the average value for binding to other proteins that also bind retinoids, such as retinal analogs. Preferably, opsin binding agents are non-retinoid opsin-binding agents that bind non-covalently to opsin. Preferably, the opsin binding agent binds at or near the opsin retinal binding pocket, where the native ligand, 11-cis-retinal, normally binds. Without wishing to be bound by theory, in one embodiment the binding pocket accommodates retinal or an agent of the invention, but not both. Accordingly, when an agent of the invention is bound at or near the retinal binding pocket, other retinoids, such as 11-cis-retinal, are unable to bind to opsin. Binding of an agent of the invention inside the retinal binding pocket of a mis-folded opsin molecule serves to direct formation of the native or wild-type conformation of the opsin molecule or to stabilize a correctly folded opsin protein, thereby facilitating insertion of the now correctly-folded opsin into the membrane of a rod cell. Again, without wishing to be bound by theory, said insertion may help to maintain the wild-type conformation of opsin and the opsin-binding agent is free to diffuse out of the binding pocket, whereupon the pocket is available for binding to retinal to form light-sensitive rhodopsin.

Other methods of the invention provide a means to restore photoreceptor function in a mammalian eye containing a mis-folded opsin protein that causes reduced photoreceptor function, comprising contacting said mis-folded opsin protein with an opsin-binding agent (e.g., a non-retinoid) that reversibly binds (e.g., that binds non-covalently) at or near the retinal binding pocket. In other embodiments, binding of the opsin-binding agent to the mis-folded opsin protein competes with 11-cis-retinal for binding in said binding pocket. Desirably, binding of the opsin-binding agent restores the native conformation of said mis-folded opsin protein.

In preferred embodiments, the mammalian eye is a human eye. In additional embodiments, said contacting occurs by administering said opsin-binding agent (e.g., non-retinoid) to a mammal afflicted with an ophthalmic condition, such as a condition characterized by reduced photoreceptor function. In various embodiments, the condition is the wet or dry form of macular degeneration, diabetic RP, a retinal or macular dystrophy, Stargardt's disease, Sorsby's dystrophy, autosomal dominant drusen, Best's dystrophy, peripherin mutation associate with macular dystrophy, dominant form of Stargart's disease, North Carolina macular dystrophy, light toxicity (e.g., due to retinal surgery), or retinitis pigmentosa. The administration may be topical administration or by systemic administration, the latter including oral administration, intraocular injection or periocular injection. Topical administration can include, for example, eye drops containing an effective amount of an agent of the invention in a suitable pharmaceutical carrier.

In another embodiment, the present invention also provides a method of stabilizing a mutant opsin protein, comprising contacting said mutant opsin protein with a non-retinoid opsin-binding agent that reversibly binds non-covalently (for example, at or in the retinal binding pocket) to said mutant opsin protein to prevent retinoid binding in said binding pocket, thereby stabilizing said mutant opsin protein.

The present invention also provides a method of ameliorating loss of photoreceptor function in a mammalian eye, comprising administering an effective amount of an opsin-binding agent, such as a non-retinoid, to a mammal afflicted with a mutant opsin protein that has reduced affinity for 11-cis-retinal, whereby the opsin binding agent reversibly binds (e.g., non-covalently) to the retinal binding pocket of said mutant opsin, thereby ameliorating loss of photoreceptor function in said mammalian eye. In one embodiment, the contacting occurs by administering said opsin-binding agent to a mammal afflicted with said reduced photoreceptor function, wherein said administering may be by topical administration or by systemic administration, the latter including oral, intraocular injection or periocular injection, and the former including the use of eye drops containing an agent of the invention. Such loss of photoreceptor function may be a partial loss or a complete loss, and where a partial loss it may be to any degree between 1% loss and 99% loss. In addition, such loss may be due to the presence of a mutation that causes mis-folding of the opsin, such as where the mutation is the P23H mutation. In another embodiment, the opsin binding agent is administered to ameliorate an opthalmic condition related to the mislocalization of an opsin protein. In one embodiment, the invention provides for the treatment of a subject having the dry form of age-related macular degeneration, where at least a portion of the opsin present in an ocular photoreceptor cell (e.g., a rod or cone cell) is mislocalized. The mislocalized protein fails to be inserted into the membrane of a photoreceptor cell, where its function is required for vision. Administration of the opsin binding agent to a subject having a mislocalized opsin protein rescues, at least in part, opsin localization. Accordingly, the invention is useful to prevent or treat an ophthalmic condition related to opsin mislocalization or to ameliorate a symptom thereof.

The present invention provides a method for treating and/or preventing an ophthalmic condition or a symptom thereof, including but not limited to, wet or dry form of macular degeneration, retinitis pigmentosa, a retinal or macular dystrophy, Stargardt's disease, Sorsby's dystrophy, autosomal dominant drusen, Best's dystrophy, peripherin mutation associate with macular dystrophy, dominant form of Stargart's disease, North Carolina macular dystrophy, light toxicity (e.g., due to retinal surgery), or retinitis pigmentosa in a subject, such as a human patient, comprising administering to a subject afflicted with, or at risk of developing, one of the aforementioned conditions or another ophthalmic condition related to the expression of a mis-folded or mislocalized opsin protein using a therapeutically effective amount of an opsin-binding agent, e.g., an agent that shows positive activity when tested in any one or more of the screening assays of the invention.

Such a method may also comprise administering to said subject at least one additional agent selected from the group consisting of a proteasomal inhibitor, an autophagy inhibitor, a lysosomal inhibitor, an inhibitor of protein transport from the ER to the Golgi, an Hsp90 chaperone inhibitor, a heat shock response activator, a glycosidase inhibitor, and a histone deacetylase inhibitor, wherein the opsin-binding compound and the additional compound are administered simultaneously or within fourteen days of each other in amounts sufficient to treat the subject.

Here again the patient may comprise a mutation that affects protein folding where said mutation(s) causes mis-folding, e.g., in an opsin protein, and may be any of the mutations recited elsewhere herein, such as a P23H mutation. In other embodiments, the patient has an ophthalmic condition that is related to the mislocalization of an opsin protein. The mislocalized opsin fails to insert into the membrane of a photoreceptor cell (e.g., a rod or cone cell). In general, this failure in localization would effect only a portion of the opsin present in an ocular cell of a patient.

In particular examples of the methods of the invention, the opsin-binding compound and the additional compound are administered within ten days of each other, more preferably within five days of each other, even more preferably within twenty-four hours of each other and most preferably are administered simultaneously. In one example, the opsin-binding compound and the additional compound are administered directly to the eye. Such administration may be intra-ocular. In other examples, the opsin-binding compound and the additional compound are each incorporated into a composition that provides for their long-term release, such as where the composition is part of a microsphere, nanosphere, or nano emulsion. In one example, the composition is administered via a drug-delivery device that effects long-term release. Such methods also contemplate administering a vitamin A supplement along with an agent of the invention.

As described herein, the opsin-binding agents useful in the methods of the invention are available for use alone or in combination with one or more additional compounds to treat or prevent conditions associated with the wet or dry form of macular degeneration, retinitis pigmentosa, a retinal or macular dystrophy, Stargardt's disease, Sorsby's dystrophy, autosomal dominant drusen, Best's dystrophy, peripherin mutation associate with macular dystrophy, dominant form of Stargart's disease, North Carolina macular dystrophy, light toxicity (e.g., due to retinal surgery), retinitis pigmentosa or another ophthalmic condition related to the expression of a misfolded or mislocalized opsin protein. In one embodiment, an opsin-hinding compound of the invention (e.g., a non-retinoid or a retinoid that fails to covalently bind to opsin) is administered to a subject identified as having or at risk of developing such a condition. Optionally, the opsin binding agent is administered together with another therapeutic agent. In another embodiment, a non-retinoid opsin-binding compound of the invention is used in combination with a synthetic retinoid (e.g., as disclosed in U.S. Patent Publication No. 2004-0242704), and optionally with another active compound (e.g., as discussed herein). In still another exemplary embodiment, an opsin-binding compound is administered in combination with the proteasomal inhibitor MG132, the autophagy inhibitor 3-methyladenine, a lysosomal inhibitor, such as ammonium chloride, the ER-Golgi transport inhibitor brefeldin A, the Hsp90 chaperone inhibitor Geldamycin, the heat shock response activator Celastrol, the glycosidase inhibitor, and/or the histone deacetylase inhibitor Scriptaid, or any other agent that can stabilize a mutant P23H opsin protein in a biochemically functional conformation that allows it to associate with 11-cis-retinal to form rhodopsin.

In specific embodiments, an opsin-binding compound is a non-polymeric (e.g., a small molecule, such as those disclosed herein for use in the methods of the invention) compound having a molecular weight less than about 1000 daltons, less than 800, less than 600, less than 500, less than 400, or less than about 300 daltons. In certain embodiments, a compound of the invention increases the amount (e.g., from or in a cell) of a stably-folded and/or complexed mutant protein by at least 10%, 15%, 20%, 25%, 50%, 75%, or 100% compared to an untreated control cell or protein.

Proteasomal Inhibitors

The 26S proteasome is a multicatalytic protease that cleaves ubiquinated proteins into short peptides. MG-132 is one proteasomal inhibitor that may be used. MG-132 is particularly useful for the treatment of light toxicity and other ocular diseases related to the accumulation of visual cycle products (e.g., all-trans-retinal, A2E, lipofuscin), protein aggregation or protein misfolding. Other proteasomal inhibitors useful in combination with of the invention in the methods of the invention include lactocystin (LC), clasto-lactocystin-beta-lactone, PSI (N-carbobenzoyl-Ile-Glu-(OtBu)-Ala-Leu-CHO), MG-132 (N-carbobenzoyl-Leu-Leu-Leu-CHO), MG-115 (N-carbobenzoyl-Leu-Leu-Nva-CHO), MG-101 (N-Acetyl-Leu-Leu-norLeu-CHO), ALLM (N-Acetyl-Leu-Leu-Met-CHO), N-carbobenzoyl-Gly-Pro-Phe-leu-CHO, N-carbobenzoyl-Gly-Pro-Ala-Phe-CHO, N-carbobenzoyl-Leu-Leu-Phe-CHO, and salts or analogs thereof. Other proteasomal inhibitors and their uses are described in U.S. Pat. No. 6,492,333.

Autophagy Inhibitors

Autophagy is an evolutionarily conserved mechanism for the degradation of cellular components in the cytoplasm, and serves as a cell survival mechanism in starving cells. During autophagy pieces of cytoplasm become encapsulated by cellular membranes, forming autophagic vacuoles that eventually fuse with lysosomes to have their contents degraded. Autophagy inhibitors may be used in combination with an opsin-binding or opsin-stabilizing compound of the invention. Autophagy inhibitors useful in combination with a of the invention in the methods of the invention include, but are not limited to, 3-methyladenine, 3-methyl adenosine, adenosine, okadaic acid, $N^6$-mercaptopurine riboside ($N^6$-MPR), an aminothiolated adenosine analog, 5-amino-4-imidazole carboxamide riboside (AICAR), bafilomycin A1, and salts or analogs thereof.

Lysosomal Inhibitors

The lysosome is a major site of cellular protein degradation. Degradation of proteins entering the cell by receptor-mediated endocytosis or by pinocytosis, and of plasma membrane proteins takes place in lysosomes. Lysosomal inhibitors, such as ammonium chloride, leupeptin, trans-epoxysaccinyl-L-leucylamide-(4-guanidino) butane, L-methionine methyl ester, ammonium chloride, methylamine, chloroquine, and salts or analogs thereof, are useful in combination with an opsin-binding or opsin-stabilizing compound of the invention.

HSP90 Chaperone Inhibitors

Heat shock protein 90 (Hsp90) is responsible for chaperoning proteins involved in cell signaling, proliferation and survival, and is essential for the conformational stability and function of a number of proteins. HSP-90 inhibitors are useful in combination with an opsin-binding or opsin-stabilizing compound in the methods of the invention. HSP-90 inhibitors include benzoquinone ansamycin antibiotics, such as geldanamycin and 17-allylamino-17-demethoxygeldanamycin (I7-AAG), which specifically bind to Hsp90, alter its function, and promote the proteolytic degradation of substrate proteins. Other HSP-90 inhibitors include, but are not limited to, radicicol, novobiocin, and any Hsp90 inhibitor that binds to the Hsp90 ATP/ADP pocket.

Heat Shock Response Activators

Celastrol, a quinone methide triterpene, activates the human heat shock response. In combination with an opsin-binding or opsin-stabilizing compound in methods of the invention, celastrol and other heat shock response activators are useful for the treatment of PCD. Heat shock response activators include, but are not limited to, celastrol, celastrol methyl ester, dihydrocelastrol diacetate, celastrol butyl ester, dihydrocelastrol, and salts or analogs thereof.

Histone Deacetylase Inhibitors

Regulation of gene expression is mediated by several mechanisms, including the post-translational modifications of histones by dynamic acetylation and deacetylation. The enzymes responsible for reversible acetylationl/deacetylation processes are histone acetyltransferases (HATs) and histone deacetylases (HDACs), respectively. Histone deacetylase inhibitors include Scriptaid, APHA Compound 8, Apicidin, sodium butyrate, (−)-Depudecin, Sirtinol, trichostatin A, and salts or analogs thereof. Such inhibitors may be used in combination with compounds of the invention in the methods disclosed herein.

Glycosidase Inhibitors

Glycosidase inhibitors are one class of compounds that are useful in the methods of the invention, when administered in combination with an opsin-binding or opsin-stabilizing compound of the invention. Castanospermine, a polyhydroxy alkaloid isolated from plant sources, inhibits enzymatic glycoside hydrolysis. Castanospermine and its derivatives are particularly useful for the treatment of light toxicity or of an ocular Protein Conformation Disorder, such as RP. Also useful in the methods of the invention are other glycosidase inhibitors, including australine hydrochloride, 6-Acetamido-6-deoxy-castanosperrnine, which is a powerful inhibitor of hexosaminidases, Deoxyfuconojirimycin hydrochloride (DFJ7), Deoxynojirimycin (DNJ), which inhibits glucosidase I and II, Deoxygalactonojirimycin hydrochloride (DGJ), winch inhibits α-D-Deoxymannojirimycin hydrochloride (DM1), 2R,5R-Bis(hydroxymethyl)-3R,4R-dihydroxypyrrolidine (DMDP), also known as 2,5-dideoxy-2,5-imino-D-mannitol, 1,4-Dideoxy-1,4-imino-D-mannitol hydrochloride, (3R,4R,5R,6R)-3,4,5,6-Tetrahydroxyazepane Hydrochloride, which inhibits b-N-acetylglucosaminidase, 1,5-Dideoxy-1,5-imino-xylitol, which inhibits β-glucosidase, and Kifunensine, an inhibitor of mannosidase 1. Also useful in combination with an opsin-binding or opsin-stabilizing compound are N-butyldeoxynojirimycin (EDNJ), N-nonyl DNJ (NDND, N-hexyl DNJ (I5TDNJ), N-methyldeoxynojirimycin (MDNJ), and other glycosidase inhibitors known in the art. Glycosidase inhibitors are available commercially, for example, from Industrial Research Limited (Wellington, New Zealand) and methods of using them are described, for example, in U.S. Pat. Nos. 4,894,388, 5,043,273, 5,103,008, 5,844,102, and 6,831,176; and in U.S. Patent Publication Nos. 20020006909.

Pharmaceutical Compositions

The present invention features pharmaceutical preparations comprising compounds together with pharmaceutically acceptable carriers, where the compounds provide for the inhibition of visual cycle products, such as all-trans-retinal or other products formed from 11-cis-retinal. Such preparations have both therapeutic and prophylactic applications. In one embodiment, a pharmaceutical composition includes an opsin-binding or stabilizing compound (e.g., a compound identified using the methods of Example 1) or a pharmaceutically acceptable salt thereof; optionally in combination with at least one additional compound that is a proteasomal inhibitor, an autophagy inhibitor, a lysosomal inhibitor, an inhibitor of protein transport from the ER to the Golgi, an Hsp9O chaperone inhibitor, a heat shock response activator, a glycosidase inhibitor, or a histone deacetylase inhibitor. The opsin-binding or opsin-stabilizing compound is preferably not a natural or synthetic retinoid. The opsin-binding or opsin-stabilizing compound and the additional compound are formulated together or separately. Compounds of the invention may be administered as part of a pharmaceutical composition. The non-oral compositions should be sterile and contain a therapeutically effective amount of the opsin-binding or opsin-stabilizing compound in a unit of weight or volume suitable for administration to a subject. The compositions and combinations of the invention can be part of a pharmaceutical pack, where each of the compounds is present in individual dosage amounts.

The phrase "pharmaceutically acceptable" refers to those compounds of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Non-oral pharmaceutical compositions of the invention to be used for prophylactic or therapeutic administration should be sterile. Sterility is readily accomplished by filtration through sterile filtration membranes (e.g., 0.2 μm membranes), by gamma irradiation, or any other suitable means known to those skilled in the art. Therapeutic opsin-binding or opsin-stabilizing compound compositions generally are placed into a container having a sterile access port, for example, an intravenous solution bag or vial having a stopper pierceable by a hypodermic injection needle. These compositions ordinarily will be stored in unit or multi-dose containers, for example, sealed ampoules or vials, as an aqueous solution or as a lyophilized formulation for reconstitution. The compounds may be combined, optionally, with a pharmaceutically acceptable excipient.

The components of the pharmaceutical compositions also are capable of being co-mingled with the molecules of the present invention, and with each other, in a manner such that there is no interaction that would substantially impair the desired pharmaceutical efficacy.

Compounds of the present invention can be contained in a pharmaceutically acceptable excipient. The excipient preferably contains minor amounts of additives such as substances that enhance isotonicity and chemical stability. Such materials are non-toxic to recipients at the dosages and concentrations employed, and include buffers such as phosphate, citrate, succinate, acetate, lactate, tartrate, and other organic acids or their salts; tris-hydroxymethylaminomethane (TRIS), bicarbonate, carbonate, and other organic bases and their salts; antioxidants, such as ascorbic acid; low molecular weight (for example, less than about ten residues) polypeptides, e.g., polyarginine, polylysine, polyglutamate and polyaspartate; proteins, such as serum albumin, gelatin, or immunoglobulins; hydrophilic polymers, such as polyvinylpyrrolidone (PVP), polypropylene glycols (PPGs), and polyethylene glycols (PEGs); amino acids, such as glycine, glutamic acid, aspartic acid, histidine, lysine, or arginine; monosaccharides, disaccharides, and other carbohydrates including cellulose or, its derivatives, glucose, mannose, sucrose, dextrins or sulfated carbohydrate derivatives, such as heparin, chondroitin sulfate or dextran sulfate; polyvalent metal ions, such as divalent metal ions including calcium ions, magnesium ions and manganese ions; chelating agents, such as ethylenediamine tetraacetic acid (EDTA); sugar alcohols, such as mannitol or sorbitol; counterions, such as sodium or ammonium; and/or nonionic surfactants, such as polysorbates or poloxamers. Other additives may be included, such as stabilizers, anti-microbials, inert gases, fluid and nutrient replenishers (i.e., Ringer's dextrose), electrolyte replenishers, which can be present in conventional amounts.

The compositions, as described above, can be administered in effective amounts. The effective amount will depend upon the mode or administration, the particular condition being treated and the desired outcome. It may also depend upon the stage of the condition, the age and physical condition of the subject, the nature of concurrent therapy, if any, and like factors well known to the medical practitioner. For therapeutic applications, it is that amount sufficient to achieve a medically desirable result.

With respect to a subject suffering from, or at risk of developing, light toxicity, such as that due to ocular surgery, an effective amount is an amount sufficient to reduce the rate or extent of formation and accumulation of visual cycle products, such as all-trans-retinal, or lipofuscin, or A2E as well as preventing photocell apoptosis as a result of excessive rhodopsin activation. Here, the compounds of the present invention would be from about 0.01 mg/kg per day to about 1000 mg/kg per day. It is expected that doses ranging from about 50 to about 2000 mg/kg will be suitable. Lower doses will result from certain forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of a composition of the present invention.

A variety of administration routes are available. The methods of the invention, generally speaking, may be practiced using any mode of administration that is medically acceptable, meaning any mode that produces effective levels of the active compounds without causing clinically unacceptable adverse effects. In one preferred embodiment, a composition of the invention is administered intraocularly. Other modes of administration include oral, rectal, topical, intraocular, buccal, intravaginal, intracisternal, intracerebroventricular, intratracheal, nasal, transdermal, within/on implants, or parenteral routes. Compositions comprising a composition of the invention can be added to a physiological fluid, such as to the intravitreal humor. For CNS administration, a variety of techniques are available for promoting transfer of the therapeutic across the blood brain barrier including disruption by surgery or injection, drugs which transiently open adhesion contact between the CNS vasculature endothelial cells, and compounds that facilitate translocation through such cells. Oral administration can be preferred for prophylactic treatment because of the convenience to the patient as well as the dosing schedule.

Pharmaceutical compositions of the invention can optionally further contain one or more additional proteins as desired, including plasma proteins, proteases, and other biological material, so long as it does not cause adverse effects upon administration to a subject. Suitable proteins or biological material may be obtained from human or mammalian plasma by any of the purification methods known and available to those skilled in the art; from supernatants, extracts, or lysates of recombinant tissue culture, viruses, yeast, bacteria, or the like that contain a gene that expresses a human or mammalian plasma protein which has been introduced according to standard recombinant DNA techniques; or from the fluids (e.g., blood, milk, lymph, urine or the like) or transgenic animals that contain a gene that expresses a human plasma protein which has been introduced according to standard transgenic techniques.

Pharmaceutical compositions of the invention can comprise one or more pH buffering compounds to maintain the pH of the formulation at a predetermined level that reflects physiological pH, such as in the range of about 5.0 to about 8.0 (e.g., 6.0, 6.5, 6.8, 6.9, 7.0, 7.1, 7.2, 7.3, 7.4, 7.5, 7.6, 7.8). The pH buffering compound used in the aqueous liquid formulation can be an amino acid or mixture of amino acids, such as histidine or a mixture of amino acids such as histidine and glycine. Alternatively, the pH buffering compound is preferably an agent which maintains the pH of the formulation at a predetermined level, such as in the range of about 5.0 to about 8.0, and which does not chelate calcium ions. Illustrative examples of such pH buffering compounds include, but are not limited to, imidazole and acetate ions. The pH buffering compound may be present in any amount suitable to maintain the pH of the formulation at a predetermined level.

Pharmaceutical compositions of the invention can also contain one or more osmotic modulating agents, i.e., a compound that modulates the osmotic properties (e.g., tonicity, osmolality and/or osmotic pressure) of the formulation to a level that is acceptable to the blood stream and blood cells of recipient individuals. The osmotic modulating agent can be an agent that does not chelate calcium ions. The osmotic modulating agent can be any compound known or available to those skilled in the art that modulates the osmotic properties of the formulation. One skilled in the art may empirically determine the suitability of a given osmotic modulating agent for use in the inventive formulation. Illustrative examples of suitable types of osmotic modulating agents include, but are not limited to: salts, such as sodium chloride and sodium acetate; sugars, such as sucrose, dextrose, and mannitol; amino acids, such as glycine; and mixtures of one or more of these agents and/or types of agents. The osmotic modulating agent(s) maybe present in any concentration sufficient to modulate the osmotic properties of the formulation.

Compositions comprising an opsin-binding or opsin-stabilizing compound of the present invention can contain multivalent metal ions, such as calcium ions, magnesium ions and/or manganese ions. Any multivalent metal ion that helps stabilize the composition and that will not adversely affect recipient individuals may be used. The skilled artisan, based on these two criteria, can determine suitable metal ions empirically and suitable sources of such metal ions are known, and include inorganic and organic salts.

Pharmaceutical compositions of the invention can also be a non-aqueous liquid formulation. Any suitable non-aqueous liquid may be employed, provided that it provides stability to the active agents (a) contained therein. Preferably, the non-aqueous liquid is a hydrophilic liquid. Illustrative examples of suitable non-aqueous liquids include: glycerol; dimethyl sulfoxide (DMSO); polydimethylsiloxane (PMS); ethylene glycols, such as ethylene glycol, diethylene glycol, triethylene glycol, polyethylene glycol ("PEG") 200, PEG 300, and PEG 400; and propylene glycols, such as dipropylene glycol, tripropylene glycol, polypropylene glycol ("PPG") 425, PPG 725, PPG 1000, PEG 2000, PEG 3000 and PEG 4000.

Pharmaceutical compositions of the invention can also be a mixed aqueous/non-aqueous liquid formulation. Any suitable non-aqueous liquid formulation, such as those described above, can be employed along with any aqueous liquid formulation, such as those described above, provided that the mixed aqueous/non-aqueous liquid formulation provides stability to the compound contained therein. Preferably, the non-aqueous liquid in such a formulation is a hydrophilic liquid. Illustrative examples of suitable non-aqueous liquids include: glycerol; DMSO; EMS; ethylene glycols, such as PEG 200, PEG 300, and PEG 400; and propylene glycols, such as PPG 425, PPG 725, PEG 1000, PEG 2000, PEG 3000 and PEG 4000. Suitable stable formulations can permit storage of the active agents in a frozen or an unfrozen liquid state. Stable liquid formulations can be stored at a temperature of at least −70° C., but can also be stored at higher temperatures of at least 0° C., or between about 0° C. and about 42° C., depending on the properties of the composition. It is generally known to the skilled artisan that proteins and polypeptides are sensitive to changes in pH, temperature, and a multiplicity of other factors that may affect therapeutic efficacy.

In certain embodiments a desirable route of administration can be by pulmonary aerosol. Techniques for preparing aerosol delivery systems containing polypeptides are well known to those of skill in the art. Generally, such systems should utilize components that will not significantly impair the biological properties of the antibodies, such as the paratope binding capacity (see, for example, Sciarra and Cutie, "Aerosols," in *Remington's Pharmaceutical Sciences* 18th edition, 1990, pp 1694-1712; incorporated by reference). Those of skill in the art can readily modify the various parameters and conditions for producing polypeptide aerosols without resorting to undue experimentation.

Other delivery systems can include time-release, delayed release or sustained release delivery systems. Such systems can avoid repeated administrations of compositions of the invention, increasing convenience to the subject and the physician. Many types of release delivery systems are available and known to those of ordinary skill in the art. They include polymer base systems such as polylactides (U.S. Pat. No. 3,773,919; European Patent No. 58,481), poly(lactideglycolide), copolyoxalates polycaprolactones, polyesteramides, polyorthoesters, poiyhydroxybutyric acids, such as poly-D-(−)-3-hydroxybutyric acid (European Patent No. 133,988), copolymers of L-glutamic acid and gamma-ethyl-L-glutamate (Sidman, K R. et at, Biopolymers 22: 547-556), poly (2-hydroxyethyl methacrylate) or ethylene vinyl acetate (Langer, et al., J. Biomed. Mater. Res. 15:267-277; Langer, B. Chem. Tech. 12:98-105), and polyanhydrides.

Other examples of sustained-release compositions include semi-permeable polymer matrices in the form of shaped articles, e.g., films, or microcapsules. Delivery systems also include non-polymer systems that are: lipids including sterols such as cholesterol, cholesterol esters and fatty acids or neutral fats such as mono-, di- and tri-glycerides; hydrogel release systems such as biologically-derived bioresorbable hydrogel (i.e., chitin hydrogels or chitosan hydrogels); sylastic systems; peptide based systems; wax coatings; compressed tablets using conventional binders and excipients; partially filled implants; and the like. Specific examples include, but are not limited to: (a) aerosional systems in which the agent is contained in a form within a matrix such as those described in 13.5. U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480.

Another type of delivery system that can be used with the methods and compositions of the invention is a colloidal dispersion system. Colloidal dispersion systems include lipid-based systems including oil-in-water emulsions, micelles, mixed micelles, and liposomes. Liposomes are artificial membrane vessels, which are useful as a delivery vector in vivo or in vitro. Large unilamellar vessels (LUV), which range in size from 0.2-4.0 can encapsulate large macromolecules within the aqueous interior and be delivered to cells in a biologically active form (Fraley, R., and Papahadjopoulos, D., Trends Biochem. Sci. 6: 77-80).

Liposomes can be targeted to a particular tissue by coupling the liposome to a specific ligand such as a monoclonal antibody, sugar, glycolipid, or protein. Liposomes are commercially available from Gibco BRL, for example, as LIPOFECTIN™ and LIPOFECTACE™, which are formed of cationic lipids such as N-[1-(2,3 dioleyloxy)-propyl]-N,N,N-trimethylammonium chloride (DOTMA) and dimethyl dioctadecylammonium bromide (DDAB). Methods for making liposomes are well known in the art and have been described in many publications, for example, in DE 3,218,121; Epstein et al., Proc. Natl. Acad. Sci. (USA) 82:3688-3692 (1985); K. Hwang et al., Proc. Nati, Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Liposomes also have been reviewed by Gregoriadis, G., Trends Biotechnol., 3: 235-241.

Another type of vehicle is a biocompatible microparticle or implant that is suitable for implantation into the mammalian recipient. Exemplary bioerodible implants that are useful in accordance with this method are described in PCT International application no. PCTIUS/03307 (Publication No-WO 95/24929, entitled "Polymeric Gene Delivery System"). PCT/US/0307 describes biocompatible, preferably biodegradable polymeric matrices for containing an exogenous gene under the control of an appropriate promoter. The polymeric matrices can be used to achieve sustained release of the exogenous gene or gene product in the subject.

The polymeric matrix preferably is in the form of a microparticle such as a microsphere (wherein an agent is dispersed throughout a solid polymeric matrix) or a microcapsule (wherein an agent is stored in the core of a polymeric shell). Microcapsules of the foregoing polymers containing drugs are described in, for example, U.S. Pat. No. 5,075,109. Other forms of the polymeric matrix for containing an agent include films, coatings, gels, implants, and stents. The size and composition of the polymeric matrix device is selected to result in favorable release kinetics in the tissue into which the matrix is introduced. The size of the polymeric matrix further is selected according to the method of delivery that is to be used. Preferably, when an aerosol route is used the polymeric matrix and composition are encompassed in a surfactant vehicle. The polymeric matrix composition can be selected to have both favorable degradation rates and also to be formed of a material, which is a bioadhesive, to further increase the effectiveness of transfer. The matrix composition also can be selected not to degrade, but rather to release by diffusion over an extended period of time. The delivery system can also be a biocompatible microsphere that is suitable for local, site-specific delivery. Such microspheres are disclosed in Chickering, D. B., et al., Biotechnot. Bioeng, 52: 96-101; Mathiowitz, B., et al., Nature 386: 410-414.

Both non-biodegradable and biodegradable polymeric matrices can be used to deliver the compositions of the invention to the subject. Such polymers may be natural or synthetic polymers. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

Exemplary synthetic polymers which can be used to form the biodegradable delivery system include: polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluoses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulfate sodium salt, poly(methyl methacrylate), polyethyl methacrylate), poly (butyl methacrylate), poly(isobutyl methacrylate), poly (hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly (ethylene glycol), poly(ethylene oxide), poly(ethylene terephthalate), poly(vinyl alcohols), poly(vinyl acetate), poly(vinyl chloride), polystyrene, poly(viny lpyrrolidone), and polymers of lactic acid and glycolic acid, polyanhydrides, poly(ortho)esters, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Methods of Ocular Delivery

The compositions of the invention are particularly suitable for treating ocular diseases or conditions, such as light toxicity, in particular light toxicity related to an ocular surgical procedure.

In one approach, the compositions of the invention are administered through an ocular device suitable for direct implantation into the vitreous of the eye. The compositions of the invention may be provided in sustained release compositions, such as those described in, for example, U.S. Pat. Nos. 5,672,659 and 5,595,760. Such devices are found to provide sustained controlled release of various compositions to treat the eye without risk of detrimental local and systemic side effects. An object of the present ocular method of delivery is to maximize the amount of drug contained in an intraocular device or implant while minimizing its size in order to prolong the duration of the implant. See, e.g., U.S. Pat. Nos. 5,378,475; 6,375,972, and 6,756,058 and U.S. Publications 20050096290 and 200501269448. Such implants may be biodegradable and/or biocompatible implants, or may be non-biodegradable implants.

Biodegradable ocular implants are described, for example, in U.S. Patent Publication No. 20050048099. The implants may be permeable or impermeable to the active agent, and may be inserted into a chamber of the eye, such as the anterior or posterior chambers or may be implanted in the sclera, transchoroidal space, or an avascularized region exterior to the vitreous. Alternatively, a contact lens that acts as a depot for compositions of the invention may also be used for drug delivery.

In a preferred embodiment, the implant may be positioned over an avascular region, such as on the sclera, so as to allow for transcleral diffusion of the drug to the desired site of treatment, e.g. the intraocular space and macula of the eye. Furthermore, the site of transcleral diffusion is preferably in proximity to the macula. Examples of implants for delivery of a composition of the invention include, but are not limited to, the devices described in U.S. Pat. Nos. 3,416,530; 3,828,777; 4,014,335; 4,300,557; 4,327,725; 4,853,224; 4,946,450; 4,997,652; 5,147,647; 164,188; 5,178,635; 5,300,114; 5,322,691; 5,403,901; 5,443,505; 5,466,466; 5,476,511; 5,516,522; 5,632,984; 5,679,666; 5,710,165; 5,725,493; 5,743,274; 5,766,242; 5,766,619; 5,770,592; 5,773,019; 5,824,072; 5,824,073; 5,830,173; 5,836,935; 5,869,079, 5,902,598; 5,904,144; 5,916,584; 6,001,386; 6,074,661; 6,110,485; 6,126,687; 6,146.366; 6,251,090; and 6,299,895, and in WO 01/30323 and WO 01/28474, all of which are incorporated herein by reference.

Examples include, but are not limited to the following: a sustained release drug delivery system comprising an inner reservoir comprising an effective amount of an agent effective in obtaining a desired local or systemic physiological or pharmacological effect, an inner tube impermeable to the passage of the agent, the inner tube having first and second ends and covering at least a portion of the inner reservoir, the inner tube sized and formed of a material so that the inner tube is capable of supporting its own weight, an impermeable member positioned at the inner tube first end, the impermeable member preventing passage of the agent out of the reservoir through the inner tube first end, and a permeable member positioned at the inner tube second end, the permeable member allowing diffusion of the agent out of the reservoir through the inner tube second end; a method for administering a compound of the invention to a segment of an eye, the method comprising the step of implanting a sustained release device to deliver the compound of the invention to the vitreous of the eye or an implantable, sustained release device for administering a compound of the invention to a segment of an eye; a sustained release drug delivery device comprising: a) a drug core comprising a therapeutically effective amount of at least one first agent effective in obtaining a diagnostic effect or effective in obtaining a desired local or systemic physiological or pharmacological effect; b) at least one unitary cup essentially impermeable to the passage of the agent that surrounds and defines an internal compartment to accept the drug core, the unitary cup comprising an open top end with at least one recessed groove around at least some portion of the open top end of the unitary cup; c) a permeable plug which is permeable to the passage of the agent, the permeable plug is positioned at the open top end of the unitary cup wherein the groove interacts with the permeable plug holding it in position and closing the open top end, the permeable plug allowing passage of the agent out of the drug core, though the permeable plug, and out the open top end of the unitary cup; and d) at least one second agent effective in obtaining a diagnostic effect or effective in obtaining a desired local or systemic physiological or pharmacological effect; or a sustained release drug delivery device comprising: an inner core comprising an effective amount of an agent having a desired solubility and a polymer coating layer, the polymer layer being permeable to the agent, wherein the polymer coating layer completely covers the inner core.

Other approaches for ocular delivery include the use of liposomes to target a compound of the present invention to the eye, and preferably to retinal pigment epithelial cells and/or Bruch's membrane. For example, the compound maybe complexed with liposomes in the manner described above, and this compound/liposome complex injected into patients with an ophthalmic condition, such as light toxicity, using intravenous injection to direct the compound to the desired ocular tissue or cell. Directly injecting the liposome complex into the proximity of the retinal pigment epithelial cells or Bruch's membrane can also provide for targeting of the complex with some forms of ocular PCD. In a specific embodiment, the compound is administered via intra-ocular sustained delivery (such as VITRASERT or ENVISION. In a specific embodiment, the compound is delivered by posterior subtenons injection. In another specific embodiment, microemulsion particles containing the compositions of the invention are delivered to ocular tissue to take up lipid from Bruchs membrane, retinal pigment epithelial cells, or both.

Nanoparticles are a colloidal carrier system that has been shown to improve the efficacy of the encapsulated drug by prolonging the serum half-life. Polyalkylcyanoacrylates (PACAs) nanoparticles are a polymer colloidal drug delivery system that is in clinical development, as described by Stella et al, J. Pharm. Sci., 2000. 89: p. 1452-1464; Brigger et al., Tnt. J. Pharm., 2001. 214: p. 37-42; Calvo et al., Pharm. Res., 2001. 18: p. 1157-1166; and Li et al., Biol. Pharm. Bull., 2001. 24: p. 662-665. Biodegradable poly (hydroxyl acids), such as the copolymers of poly (lactic acid) (PLA) and poly (lactic-co-glycolide) (PLGA) are being extensively used in biomedical applications and have received FDA approval for certain clinical applications. In addition, PEG-PLGA nanoparticles have many desirable carrier features including (i) that the agent to be encapsulated comprises a reasonably high weight fraction (loading) of the total carrier system; (ii) that the amount of agent used in the first step of the encapsulation process is incorporated into the final carrier (entrapment efficiency) at a reasonably high level; (iii) that the carrier have the ability to be freeze-dried and reconstituted in solution without aggregation; (iv) that the carrier be biodegradable; (v) that the carrier system be of small size; and (vi) that the carrier enhance the particles persistence.

Nanoparticles are synthesized using virtually any biodegradable shell known in the art. In one embodiment, a polymer, such as poly (lactic-acid) (PLA) or poly (lactic-co-glycolic acid) (PLGA) is used. Such polymers are biocompatible and biodegradable, and are subject to modifications that desirably increase the photochemical efficacy and circulation lifetime of the nanoparticle. In one embodiment, the polymer is modified with a terminal carboxylic acid group (COOH) that increases the negative charge of the particle and thus limits the interaction with negatively charge nucleic acid aptamers. Nanoparticles are also modified with polyethylene glycol (PEG), which also increases the half-life and stability of the particles in circulation. Alternatively, the COOH group is converted to an N-hydroxysuccinimide (NHS) ester for covalent conjugation to amine-modified aptamers.

Biocompatible polymers useful in the composition and methods of the invention include, but are not limited to, polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, poly(vinylpyrrolidone), polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulfate sodium salt poly-methyl methacrylate), poly(ethyl methacrylate), poly(butyl methacrylate), poly(isobutyl methacrylate\poly(hexyl methacrylate), poly(isodecyl methacrylate), poly(lauryl methacrylate), poly(phenyl methacrylate), poly(methyl acrylate), poly(isopropyl acrylate), poly (isobutyl acrylate), poly(octadecyl acrylate), polyethylene, polypropylene poly(ethylene glycol), poly(ethylene oxide), poly(ethylene terephthalate), poly(vinyl alcohols), polyvinyl acetate, polyvinyl chloride polystyrene, poly(vinyl pyrrolidone), polyhyaluronic acids, casein, gelatin, glutin, polyanhydrides, polyacrylic acid, alginate, chitosan, poly(methyl methacrylates), poly(ethyl methacrylates), poly(butyl methacrylate), poly(isobutyl methacrylate), poly(hexyl methacrylate) poly(isodecyl methaerylate), poly(lauryl methacrylate), poly(phenyl methacrylate), poly(methyl acrylate), poly(isopropyl acrylate), poly(isobutyl acrylate), poly(octadecyl acrylate) and combinations of any of these, In one embodiment, the nanoparticles of the invention include PEG-PLGA polymers.

Compositions of the invention may also be delivered topically. For topical delivery, the compositions are provided in any pharmaceutically acceptable excipient that is approved for ocular delivery. Preferably, the composition is delivered in drop form to the surface of the eye. For some application, the delivery of the composition relies on the diffusion of the compounds through the cornea to the interior of the eye.

Those of skill in the art will recognize that treatment regimens for using the compounds of the present invention to treat light toxicity or other opthalmic conditions (e.g., RP) can be straightforwardly determined. This is not a question of experimentation, but rather one of optimization, which is routinely conducted in the medical arts. In vivo studies in nude mice often provide a starting point from which to begin to optimize the dosage and delivery regimes. The frequency of injection will initially be once a week, as has been done in some mice studies. However, this frequency might be optimally adjusted from one day to every two weeks to monthly, depending upon the results obtained front the initial clinical trials and the needs of a particular patient.

Human dosage amounts can initially be determined by extrapolating from the amount of compound used in mice, as a skilled artisan recognizes it is routine in the art to modify the dosage for humans compared to animal models. For certain embodiments it is envisioned that the dosage may vary from between about 1 mg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 10 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, 5000 mg/Kg body weight in other embodiments, it is envisaged that lower does may be used, such doses may be in the range of about 5 mg compound/Kg body to about 20 mg compound/Kg body. In other embodiments the doses may be about 8, 10, 12, 14, 16 15 or 18 mg/Kg body weight. Of course, this dosage amount may be adjusted upward or downward, as is routinely done in such treatment protocols, depending on the results of the initial clinical trials and the needs of a particular patient.

Screening Assays

Useful compounds of the invention are compounds of the formula (I) that reversibly bind to a native or mutated opsin protein, such as in or near the 11-cis-retinal binding pocket. The non bleachable or slowly bleachable pigment rhodopsins formed from these small molecule opsin bindings will prevent light toxicity related to, for example, the accumulation of visual cycle products as well as apoptotic photocell death resulting from excessive rhodopsin stimulation. Such binding will commonly inhibit, if not prevent, binding of retinoids, especially 11-cis-retinal, to the binding pocket and thereby reduce formation of visual cycle products, such as all-trans-retinal. Any number of methods are available for carrying out screening assays to identify such compounds. In one approach, an opsin protein is contacted with a candidate compound or test compound that is a non-retinoid in the presence of 11-cis-retinal or retinoid analog and the rate or yield of formation of chromophore is determined. If desired, the binding of the non-retinoid to opsin is characterized. Preferably, the non-retinoid binding to opsin is non-covalent and reversible. Thus, inhibition of rhodopsin formation by a non-retinoid indicates identification of a successful test compound. An increase in the amount of rhodopsin is assayed, for example, by measuring the protein's absorption at a characteristic wavelength (e.g., 498 nm for rhodopsin) or by measuring an increase in the biological activity of the protein using any standard method (e.g., enzymatic activity association with a ligand). Useful compounds inhibit binding of 11-cis-retinal (and formation of rhodopsin) by at least about 10%, 15%, or 20%, or preferably by 25%, 50%, or 75%, or most preferably by up to 90% or even 100%.

Alternatively, the efficacy of compounds useful in the methods of the invention may be determined by exposure of a mammalian eye to a high intensity light source prior to, during, or following administration of a test compound, followed by determination of the amount of visual cycle products (e.g., all-trans retinal, A2E, or lipofuscin) formed as a result of exposure to the high intensity light source, wherein a compound of the invention will have reduced the amount of visual cycle products related to the exposure.

In sum, preferred test compounds identified by the screening methods of the invention are non-retinoids, are selective for opsin and bind in a reversible, non-covalent manner to opsin protein. In addition, their administration to transgenic animals otherwise producing increased lipofuscin results in a reduced rate of production or a reduced accumulation of lipofuscin in the eye of said animal. Compounds identified according to the methods of the invention are useful for the treatment of light toxicity or other ophthalmic condition in a subject, such as a human patient.

Compositions of the invention useful for the prevention of light toxicity, as well as AMD and retinitis pigmentosa, can optionally be combined with additional therapies as heretofore described.

EXAMPLES

The following non-limiting examples further describe and enable one of ordinary skill in the art to make use of the invention.

Example 1

(±)-(3aR,7aS)-3,3a,7,7-tetramethyl-3a,4,5,6,7,7a-hexahydro-1H-inden-1-one

A mixture of (E)-1-(2,6,6-trimethylcyclohex-1-enyl)but-2-en-1-one (400 mg, 2.06 mmol) in phosphoric acid (85%, 3.0 mL) was stirred at room temperature for 3 hours. The mixture was poured into water (30 mL) and the organics extracted with ethyl acetate (40 mL×2). The organic layer was washed with brine, dried over anhydrous sodium sulfate and then concentrated under reduced pressure. The residue was purified by silica gel chromatography to give the title compound as a light yellow oil (362 mg, Yield: 91%). $R_f$=0.6 (20:1 petroleum ether/ethyl acetate); $^1$H NMR (400 MHz, CDCl$_3$) δ 5.75 (s, 1H), 1.98 (s, 3H), 1.82 (s, 1H), 1.64-1.52 (m, 4H), 1.36-1.33 (m, 2H), 1.18 (s, 3H), 1.16 (s, 3H), 0.88 (s, 3H) ppm; Mass spectrum (ESI+ve) m/z 193 (M+H$^+$).

Example 2

(±)-(3aS,7aR)-4,4-dimethylhexahydro-1H-indol-2(3H)-one

Example 2a 1-benzyl-4,4-dimethyl-3a,4,5,6-tetrahydro-1H-indol-2(3H)-one

To a solution of ethyl 2-(2,2-dimethyl-6-oxocyclohexyl)acetate (300 mg, 1.413 mmol) in 1,2-dichloroethane (2.5 mL) was added benzylamine (182 mg, 1.7 mmol), acetic acid (170 mg, 2.83 mmol) and sodium triacetoxyborohydride (381 mg, 1.8 mmol). The mixture was stirred at room temperature for 48 hours. The reaction mixture was diluted with dichloromethane (10 mL) and saturated aqueous sodium bicarbonate (5 mL) and the layers were separated. The aqueous layer was extracted with dichloromethane (3×10 mL) and the combined organic phase was dried over anhydrous sodium sulfate and concentrated under reduced pressure. The residue was purified by silica gel column chromatography to afford the title compound as a light yellow oil (88 mg, Yield: 19%). $^1$H NMR (400 MHz, CDCl$_3$) δ 7.34-7.21 (m, 5H), 4.78 (d, J=15.2 Hz, 1H), 4.75-4.72 (m, 1H), 4.51 (d, J=16.0 Hz, 1H), 2.78-2.61 (m, 1H), 2.52-2.24 (m, 3H), 1.56-1.40 (m, 3H), 1.01 (s, 3H), 0.85 (s, 3H) ppm; Mass spectrum (ESI+ve) m/z 256 (M+H$^+$).

Example 2b (±)-(3aS,7aR)-1-benzyl-4,4-dimethylhexahydro-1H-indol-2(3H)-one

To a solution of the product of Example 2a (88 mg, 0.35 mmol) in methanol (3 mL) was added wet 10% Pd/C (10 mg). The mixture was stirred under an atmosphere of hydrogen overnight and then was suction filtered and the filtrate was concentrated under reduced pressure. The residue was purified by silica gel column chromatography to give the title compound as a colorless oil (46 mg, Yield: 52%). $^1$H NMR (400 MHz, CDCl$_3$) δ 7.37-7.29 (m, 3H), 7.25 (d, J=7.2 Hz, 2H), 4.94 (d, J=15.6 Hz, 1H), 3.96 (d, J=14.8 Hz, 1H), 3.44-3.32 (m, 1H), 2.38-2.20 (m, 2H), 2.06-1.90 (m, 2H), 1.51-1.48 (m, 1H), 1.32-1.22 (m, 3H), 1.10-0.97 (m, 1H), 0.93 (s, 3H), 0.91 (s, 3H) ppm; Mass spectrum (ESI+ve) m/z 258 (M+H$^+$).

Example 2

(±)-(3aS,7aR)-4,4-dimethylhexahydro-1H-indol-2(3H)-one

To a solution of the product of Example 2b (25 mg, 0.098 mmol) in liquid ammonia (20 mL) was added lithium (50 mg). The mixture was stirred at −50° C. for 2 hours. Ethanol (10 mL) was slowly added to the reaction mixture at −50° C. and then it was allowed to warm slowly to room temperature. The reaction mixture was concentrated under reduced pressure and the residual solid was dissolved in water (10 mL) and then it was extracted with ethyl acetate (3×20 mL). The combined organic phase was washed with brine (5 mL), dried over anhydrous magnesium sulfate, filtered and concentrated under reduced pressure. The residue was purified by silica gel column chromatography to afford the title compound a colorless oil (13 mg, Yield: 79%). $^1$H NMR (400 MHz, CDCl$_3$) δ 5.77 (brs, 1H), 3.60-3.49 (m, 1H), 2.26-2.04 (m, 3H), 1.94-1.82 (m, 1H), 1.54-1.49 (m, 1H), 1.45-1.17 (m, 5H), 0.99 (s, 3H), 0.92 (s, 3H) ppm; Mass spectrum (ESI+ve) m/z 168 (M+H$^+$).

Example 3

(±)-(3aS,7aS)-4,4,7,7-tetramethylhexahydrobenzofuran-2(3H)-one

Example 3a 1,4,4-trimethylcyclohex-2-enol

To a stirred solution of 4,4-dimethylcyclohex-2-enone (40.0 g, 322 mmol) in 400 ml of anhydrous ether at −78° C. was added drop wise an ethereal solution of methyl lithium (220 ml of a 1.6 M ethereal solution). The resulting solution was allowed to warm to room temperature and stirred for 18 hours. The reaction was quenched by the addition of water (200 mL). The phases were separated and the aqueous layer extracted with diethyl ether (2×200 mL). The combined organic phase was washed with brine (2×50 mL), dried over anhydrous sodium sulfate and concentrated under reduced pressure to give the title compound as a light yellow oil (41 g, Yield: 90%). $R_f$=0.5 (5:1 petroleum ether/ethyl acetate);

$^1$H NMR (400 MHz, CDCl$_3$) δ 5.46 (d, J=10.0 Hz, 1H), 5.43 (d, J=10.0 Hz, 1H), 1.73-1.70 (m, 2H), 1.59-1.56 (m, 1H), 1.50-1.45 (m, 1H), 1.27 (s, 3H), 1.01 (s, 3H), 0.95 (s, 3H) ppm; Mass spectrum (ESI+ve) m/z 123 (M−H$_2$O+H$^+$).

Example 3b 3,6,6-trimethylcyclohex-2-enone

To a stirred slurry of pyridinium chlorochromate (123 g, 570 mmol), in dichloromethane (840 mL) at room temperature was added in one portion a solution of the product of Example 3a (40.0 g, 285 mmol) in dichloromethane (240 mL). The resulting dark red mixture was allowed to stir for 18 hours at room temperature after which it was filtered and the precipitate washed with diethyl ether (200 mL). The filtrate was washed successively with 5% aqueous sodium hydroxide (2×200 mL), 5% aqueous hydrochloric acid (200 mL) and saturated aqueous sodium bicarbonate (2×50 mL). The organic phase was dried over anhydrous magnesium sulfate, filtered and concentrated under reduced pressure. The residue was purified by silica gel column chromatography to afford the title compound as a colorless oil (14 g, Yield: 35%). R$_f$=0.4 (5:1 petroleum ether/ethyl acetate); $^1$H NMR (400 MHz, CDCl$_3$) δ 5.77 (s, 1H), 2.29 (t, J=6.0 Hz, 2H), 1.93 (s, 3H), 1.80 (d, J=6.0 Hz, 3H), 1.09 (s, 6H) ppm; Mass spectrum (ESI+ve) m/z 139 (M+H$^+$).

Example 3c 2,2,5,5-tetramethylcyclohexanone

Cuprous iodide (6.9 g, 36.2 mmol) was added to a dry 250-mL round-bottom flask equipped with a stir bar and sealed under argon with a septum. The flask was evacuated with a vacuum pump and purged with argon. This process was repeated three times. Tetrahydrofuran (75 mL) was injected and the slurry was cooled to −78° C. and then methyl lithium (45 mL, 72 mmol) was added drop wise. The mixture was allowed to warm until homogeneous and then was recooled to −78° C. and boron trifluoride etherate (8.9 mL, 72 mmol) was added via a syringe. The compound of Example 3b (5.0 g, 36.2 mmol) was added neat and the reaction mixture was stirred for 1.5 hours. The reaction was quenched with ammonium hydroxide/saturated ammonium chloride (1:9, 250 mL). The organics were extracted with ethyl acetate (250 mL) and the organic layer was washed with aqueous saturated sodium bicarbonate (50 mL×2), brine (50 mL), dried over anhydrous sodium sulfate and concentrated under reduced pressure. The residue was purified by silica gel column chromatography to afford the title compound as a clear oil (1.5 g, Yield: 26%). $^1$H NMR (400 MHz, CDCl$_3$) δ 2.21 (s, 2H), 1.69-1.65 (m, 2H), 1.61-1.57 (m, 2H), 1.09 (s, 6H), 0.94 (s, 6H); $^{13}$C NMR (101 MHz, CDCl$_3$) δ 216.36, 51.32, 44.00, 36.89, 36.62, 34.69, 28.5, 25.15 ppm; Mass spectrum (ESI+ve) m/z 155 (M+H$^+$).

Example 3d ethyl 2-(2,2,5,5-tetramethyl-6-oxocyclohexyl)acetate

To a solution of the product of Example 3c (308 mg, 2.0 mmol) in tetrahydrofuran (5 mL) at −78° C. was added lithium diisopropylamide (1.1 mL, 2.2 mmol) and the solution was stirred for 1 hour. Ethyl 2-bromoacetate (680 mg, 4.0 mmol) and hexamethylphosphoramide (427 mg, 2.4 mmol) was added and the solution was allowed to warm to room temperature and stirred overnight. The mixture was poured into saturated ammonium chloride and the organics were extracted with ethyl acetate (150 mL). The organic layer was washed with water (100 mL×2) and brine (50 mL×2), dried over anhydrous sodium sulfate and concentrated under reduced pressure. The residue was purified by silica gel column chromatography to give the title compound as a colorless oil (200 mg) that was used directly in the next step.

Example 3

(±)-(3aS,7aS)-4,4,7,7-tetramethylhexahydrobenzo-furan-2(3H)-one

To a mixture of the product of Example 3d (180 mg, 0.4 mmol) in methanol (2.0 mL) at 0° C. was added sodium borohydride (38 mg, 1.0 mmol). The reaction mixture was stirred for 2 hours and then the reaction was quenched with saturated aqueous ammonium chloride. The organics were extracted with ethyl acetate (150 mL) and the organic layer was washed with water (100 mL×2), brine (50 mL×2) dried over anhydrous sodium sulfate and concentrated under reduced pressure. The residue was purified by silica gel column chromatography to afford the title compound as a white solid (10 mg, Yield: 13%). Mp=94.8-95.2° C.; R$_f$=0.4 (10:1 petroleum ether/ethyl acetate); $^1$H NMR (400 MHz, CDCl$_3$) δ 4.03 (d, J=5.2 Hz, 1H), 2.44 (d, J=5.2 Hz, 2H), 2.22-2.19 (m, 1H), 1.39-1.26 (m, 4H), 1.07 (s, 3H), 1.01 (s, 3H), 0.94 (s, 3H), 0.91 (s, 3H) ppm; Mass spectrum (ESI+ve) m/z 197 (M+H$^+$).

Example 4

(±)-(3aS,7aR)-1,4,4-trimethylhexahydro-1H-indol-2(3H)-one

Example 4a 1,4,4-trimethyl-3a,4,5,6-tetrahydro-1H-indol-2(3H)-one

To a solution of ethyl 2-(2,2-dimethyl-6-oxocyclohexyl)acetate (300 mg, 1.4 mmol) in 1,2-dichloroethane (3 mL) was added methylamine alcohol solution (340 mg, 2.83 mmol), sodium triacetoxyborohydride (390 mg, 1.84 mmol) and acetic acid (0.17 mL, 2.83 mmol). The mixture was stirred at room temperature overnight. Water (10 mL) was added to the reaction mixture and then the organics were extracted with ethyl acetate (3×30 mL). The organic layer was washed with brine (5 mL), dried over anhydrous sodium sulfate and concentrated under reduced pressure. The residue was purified by silica gel column chromatography to give the title compound as a light yellow oil (40 mg, Yield: 16%). $^1$H NMR (400 MHz, CDCl$_3$) δ 4.72 (dd, J=6.4, 3.2 Hz, 1H), 2.86 (s, 3H), 2.63-2.53 (m, 1H), 2.33 (dd, J=16.4, 9.2 Hz, 1H), 2.22-2.08 (m, 3H), 1.54-1.41 (m, 2H), 0.94 (s, 3H), 0.78 (s, 3H) ppm; Mass spectrum (ESI+ve) m/z 180 (M+H$^+$).

Example 4

(±)-(3aS,7aR)-1,4,4-trimethylhexahydro-1H-indol-2(3H)-one

To a solution of the product of Example 4a (40 mg, 0.223 mmol) in methanol (4 mL) was added Pd/C (10 mg). The mixture was stirred under a hydrogen atmosphere overnight. The reaction mixture was suction filtered and the filtrate was concentrated under reduced pressure. The residue was purified by silica gel column chromatography to afford the title compound as a colorless oil (36 mg, Yield: 89%). $R_f$=0.2 (3:1 petroleum ether/ethyl acetate); $^1$H NMR (400 MHz, CDCl$_3$) δ 3.49-3.36 (m, 1H), 2.78 (s, 3H), 2.25-2.10 (m, 2H), 2.10-1.98 (m, 2H), 1.54-1.49 (m, 1H), 1.37-1.21 (m, 3H), 1.03-0.96 (m, 1H), 0.92 (s, 3H), 0.86 (s, 3H) ppm; Mass spectrum (ESI+ve) m/z 182 (M+H$^+$).

Example 5

(±)-(3aS,7aR)-4,4,7a-trimethyloctahydro-1H-inden-1-one

Example 5a 2-methyl-2-(3-oxopentyl)cyclopentane-1,3-dione

To a solution of 2-methylcyclopentane-1,3-dione (20 g, 178.2 mmol) and pent-1-en-3-one (15 g, 178.2 mmol) in dimethoxyethane (400 mL) was added 1,4-diazabicyclo[2.2.2]octane (20 g, 178.2 mmol). The mixture was stirred for 24 hours at room temperature. The mixture was acidified with 1N hydrochloric acid to pH=4.5 and the organics were extracted with diethyl ether (200 mL×3). The organic layer was washed with brine (100 mL×3) dried over anhydrous sodium sulfate and concentrated under reduced pressure to give the title compound as a light yellow oil (21.9 g, Yield: 63%). $^1$H NMR (400 MHz, CDCl$_3$) δ 2.91-2.69 (m, 4H), 2.46-2.34 (m, 4H), 1.90 (t, J=7.2 Hz, 2H), 1.11 (s, 3H), 1.01 (t, J=7.4 Hz, 3H) ppm; Mass spectrum (ESI+ve) m/z 197 (M+H$^+$).

Example 5b 4,7a-dimethyl-2,3,7,7a-tetrahydro-1H-indene-1,5(6H)-dione

To a solution of the product of Example 5a (21.92 g, 111.7 mmol) in toluene (250 mL) was added p-toluenesulfonic acid (6.37 g, 33.51 mmol). The mixture was refluxed for 1 hour. The mixture was concentrated under reduced pressure and the residue was extracted with dichloromethane (100 mL×3). The organic layer was washed with saturated aqueous sodium bicarbonate (100 mL×2) and brine (100 mL×2), dried over anhydrous sodium sulfate and concentrated under reduced pressure to give the title compound as a brown yellow oil (20 g, yield: 100%). $^1$H NMR (400 MHz, CDCl$_3$) δ 3.00-2.69 (m, 3H), 2.60-2.36 (m, 3H), 2.07 (ddd, J=13.4, 5.2, 2.2 Hz, 1H), 1.90-1.79 (m, 1H), 1.77 (s, 3H), 1.28 (s, 3H) ppm; Mass spectrum (ESI+ve) m/z 179 (M+H$^+$).

Example 5c

4',7a'-dimethyl-2',3',7',7a'-tetrahydrospiro[[1,3]dioxolane-2,1'-inden]-5'(6'H)-one To a solution of Example 5b (5 g, 28.0 mmol) in 2-ethyl-2-methyl-1,3-dioxolane (21 mL) was added p-toluenesulfonic acid (373 mg, 1.96 mmol). The mixture was stirred at room temperature for 3 days. The reaction was quenched by the addition of a few drops of triethylamine. Benzene (50 mL) was added and the solution was washed with water (20 mL×2). The organic layer was washed with saturated aqueous sodium bicarbonate (20 mL×2) and brine (20 mL×2), dried over anhydrous sodium sulfate and concentrated under reduced pressure. The residue was purified by silica gel flash chromatography to give the title compound as yellow oil (4.02 g, Yield: 64%). $^1$H NMR (400 MHz, DMSO) δ 4.05-3.90 (m, 4H), 2.62-2.41 (m, 4H), 2.33-2.15 (m, 2H), 1.99-1.90 (m, 1H), 1.69 (s, 3H), 1.61 (ddd, J=12.6, 5.4, 2.0 Hz, 1H), 1.27 (s, 3H) ppm; Mass spectrum (ESI+ve) m/z 223 (M+H$^+$).

Example 5d (±)-(3a'S,7a'R)-4',4',7a'-trimethylhexahydrospiro[[1,3]dioxolane-2,1'-inden]-5'(6'H)-one A solution of the product of Example 5c (3.0 g, 13.5 mmol) in anhydrous tetrahydrofuran (33 mL) was added drop wise to a solution of lithium (300 mg, 43.2 mmol) in ammonia (189 mL) at −78° C. After the solution was stirred for 1 hour, methyl iodide (4.5 mL, 72.9 mmol) was added drop wise. After 3 hours at −78° C., the reaction was allowed to warm to room temperature and stirring was continued overnight. Water (45 mL) was added and the mixture was extracted with diethyl ether (60 mL×2). The organic layer was washed with water (50 mL×2) and brine (50 mL×2), dried over anhydrous sodium sulfate and concentrated under reduced pressure. The residue was purified by silica gel flash chromatography to give the title compound as a light yellow solid (1.70 g, Yield: 53%). $^1$H NMR (400 MHz, CDCl$_3$) δ 4.06-3.81 (m, 4H), 2.80-2.64 (m, 1H), 2.33-2.20 (m, 1H), 2.09-2.00 (m, 1H), 1.97-1.68 (m, 5H), 1.32-1.26 (m, 1H), 1.29 (s, 3H), 1.26 (s, 3H), 1.01 (s, 3H); $^{13}$C NMR (100 MHz, DMSO) δ 217.26, 120.03, 65.50, 64.26, 55.87, 47.33, 45.10, 34.79, 31.97, 30.74, 27.42, 24.43, 23.32, 21.27 ppm; Mass spectrum (ESI+ve) m/z 239 (M+H$^+$).

Example 5e (±)-(3a'S,7a'R)-4',4',7a'-trimethyloctahydrospiro[[1,3]dioxolane-2,1'-indene]

A mixture of the product of Example 5d (500 mg, 2.1 mmol), potassium hydroxide (943 mg, 16.8 mmol) and hydrazine hydrate (1.03 mL, 21 mmol) in diethylene glycol (12 mL) was heated at 210° C. for 2 hours. Excess hydrazine was removed and the reaction mixture was heated for an additional 12 hours. After dilution with water (40 mL), the mixture extracted with diethyl ether (40 mL×2). The organic layer was washed with brine (30 mL×2), dried over anhydrous sodium sulfate and concentrated under reduced pressure. The residue was purified by flash chromatography to give 260 mg of a colorless oil which was further purified by prep-TLC to give the title compound as a colorless oil (138 mg, Yield: 29%). $^1$H NMR (400 MHz, DMSO) δ 3.87-3.77 (m, 4H), 1.80-1.06 (m, 11H), 0.99 (s, 3H), 0.92 (s, 3H), 0.78 (s, 3H); $^{13}$C NMR (100 MHz, DMSO) δ 120.57, 65.26, 63.61, 51.58, 45.39, 33.65, 31.72, 31.39, 30.73, 29.21, 28.77, 21.96, 19.89, 18.60 ppm; Mass spectrum (ESI+ve) m/z 225 (M+H$^+$).

Example 5

(±)-(3aS,7aR)-4,4,7a-trimethyloctahydro-1H-inden-1-one

To a solution of compound the product of Example 5e (60 mg, 0.27 mmol) in acetone (5 mL) was added p-toluenesulfonic acid (4.2 mg, 0.022 mmol). Then the mixture was refluxed for 1.5 hours. The mixture was concentrated and extracted with ethyl acetate (20 mL). The organic layer was washed by saturated aqueous sodium bicarbonate (20 mL×2) and brine (20 mL×2), dried over anhydrous sodium sulfate and concentrated under reduced pressure. The residue was purified by prep-TLC to give the title compound as a colorless oil (32 mg, Yield: 65%). $R_f$=0.7 (20:1 petroleum ether/ethyl acetate); $^1$H NMR (400 MHz, CDCl$_3$) δ 2.47-2.38 (m, 1H), 2.20-2.08 (m, 1H), 1.96-1.87 (m, 1H), 1.78-1.68 (m, 1H), 1.66-1.53 (m, 2H), 1.50-1.25 (m, 4H), 1.21 (s, 3H), 1.17-1.10 (m, 1H), 1.08 (s, 3H), 0.90 (s, 3H); $^{13}$C NMR (100 MHz, DMSO) δ 223.13, 53.28, 48.44, 35.00, 35.02, 31.52, 29.52, 29.21, 28.70, 22.75, 21.37, 18.22 ppm; Mass spectrum (ESI+ve) m/z 181 (M+H$^+$).

Example 6

4,4,7a-trimethyl-5,6,7,7a-tetrahydro-1H-inden-2 (4H)-one

Example 6a ethyl 2-(1,3,3-trimethyl-2-oxocyclohexyl)acetate

To a solution of 2,2,6-trimethylcyclohexanone (2.0 g, 14.26 mmol) in dry tetrahydrofuran (15.0 mL) was added lithium diisopropylamide (7.8 mL, 15.68 mmol) drop wise over 10 min at −78° C. and the resulting solution was allowed to warm to room temperature over 2 hours. The resulting mixture was recooled to −78° C. and hexamethylphosphoramide (2.7 g, 15.0 mmol) was added. Then, ethyl bromoacetate (4.8 g, 28.52 mmol) in tetrahydrofuran (6.0 mL) was added drop wise at −78° C. The resulting mixture was allowed to warm to room temperature and stirred for 4 hours. Saturated aqueous ammonium chloride (60 mL) was added and the mixture was extracted with ethyl acetate (80 mL×2). The combined organic phase was washed with brine (100 mL) and concentrated under reduced pressure. The residue was purified by silica gel column chromatography (eluent: petroleum ether/ethyl acetate=100/1→70/1) to give the title compound as a colorless oil (3.0 g, Yield: 91%). $^1$H NMR (400 MHz, CDCl$_3$) δ: 4.12-4.04 (m, 2H), 3.03 (d, J=16.4 Hz, 1H), 2.14 (d, J=16.4 Hz, 1H), 2.04 (s, 1H), 1.85-1.81 (m, 2H), 1.69-1.59 (m, 2H), 1.32-1.21 (m, 4H), 1.14 (s, 9H) ppm; Mass spectrum (ESI+ve) m/z 227 (M+H$^+$).

Example 6b dimethyl 2-oxo-3-(1,3,3-trimethyl-2-oxocyclohexyl) propylphosphonate

To a solution of dimethyl methylphosphonate (163 mg, 1.32 mmol) in dry tetrahydrofuran (4 mL) was added n-butyl lithium (0.82 mL, 1.32 mmol) drop wise at −60° C. and the solution was stirred for 30 minutes. The product of Example 6a (100 mg, 0.44 mmol) in dry tetrahydrofuran (2.0 mL) was added drop wise. The resulting mixture was allowed to warm slowly 0° C. and stirred for 4 hours. Acetic acid was added to the solution to adjust to pH=7. Water (10 mL) was added to the solution and the organics were extracted with ethyl acetate (20 mL×2). The combined organic phase was washed with brine (30 mL), dried over anhydrous sodium sulfate and concentrated under reduced pressure. The residue was purified by silica gel column chromatography (eluent: petroleum ether/ethyl acetate=1/3) to give the title compound as a colorless oil (20 mg, Yield: 15%). $^1$H NMR (400 MHz, CDCl$_3$) δ 3.77 (d, J=6.0 Hz, 2H), 3.75 (d, J=8.8 Hz, 1H), 3.30 (d, J=18.4 Hz, 1H), 3.10 (dd, J=22.4, 13.6 Hz, 1H), 2.92 (dd, J=22:8, 13.6 Hz, 1H), 2.60 (d, J=18.4 Hz, 1H), 1.92-1.76 (m, 3H), 1.67-1.51 (m, 3H), 1.15 (s, 3H), 1.12 (s, 6H) ppm; Mass spectrum (ESI+ve) m/z 305 (M+H$^+$).

Example 6

4,4,7a-trimethyl-5,6,7,7a-tetrahydro-1H-inden-2 (4H)-one

To a solution of the product of Example 6b (124 mg, 0.407 mmol) in dry tetrahydrofuran (8.0 mL) was added sodium hydride (163 mg, 4.07 mmol) in one portion and stirred for 10 minutes at room temperature and then the reaction was heated to 60° C. for 3 hours. The reaction was quenched with the addition of saturated aqueous ammonium chloride (20 mL) and water (10 mL). The organic were extracted with ethyl acetate (50 mL×2) and the combined organic extracts were washed with brine (50 mL), dried over anhydrous sodium sulfate and concentrated in vacuo. The residue was purified by column silica gel column chromatography (eluent: petroleum ether/ethyl acetate=5/1) to afford the title compound as a colorless oil (48 mg, Yield: 70%). $R_f$=0.6 (5:1 petroleum ether/ethyl acetate); $^1$H NMR (400 MHz, CDCl$_3$) δ: 5.82 (s, 1H), 2.30 (s, 2H), 1.94-1.80 (m, 2H), 1.69-1.57 (m, 2H), 1.43-1.32 (m, 5H), 1.25 (s, 3H), 1.20 (s, 3H) ppm; Mass spectrum (ESI+ve) m/z 179 (M+H$^+$).

Example 7

4,4-dimethylhexahydrobenzofuran-2(3H)-one

To a solution of ethyl 2-(2,2-dimethyl-6-oxocyclohexyl) acetate (200 mg, 0.942 mmol) in methanol (5 mL) at 0° C. was added sodium borohydride (143 mg, 3.77 mmol) portionwise. The mixture was warmed to room temperature and stirred overnight. The reaction mixture was concentrated under reduced pressure and the residue was partitioned between water and ethyl acetate (2×20 mL). The combined organic phase was washed with brine (5 mL), dried over anhydrous magnesium sulfate, filtered and concentrated under reduced pressure. The residue was purified by silica gel column chromatography to afford the title compound as a colorless oil (100 mg, Yield: 63%). $R_f$=0.2 (20:1 petroleum ether/ethyl acetate); $^1$H NMR (400 MHz, CDCl$_3$) δ 4.64-4.56 (m, 1H), 2.49-2.19 (m, 3H), 2.07-2.02 (m, 1H), 1.63-1.58 (m, 1H), 1.48-1.25 (m, 5H), 0.99 (s, 3H), 0.93 (s, 3H) ppm; Mass spectrum (ESI+ve) m/z 169 (M+H$^+$).

Example 8

(±)-(3aS,7aS)-methyl 3a,7,7-trimethyl-3a,4,5,6,7,7a-hexahydro-1H-indene-2-carboxylate Example 8a (±)-(3aS,7aR)-methyl 4,4,7a-trimethyl-1-oxooctahydro-1H-indene-2-carboxylate To a solution of lithium diisopropylamide (1.66 mL, 3.32 mmol) in tetrahydrofuran (6 mL) at 0° C. under argon was drop wise added a solution of the product of Example 5 (300 mg, 1.66 mmol) in tetrahydrofuran (6 mL). Then the solution was warmed to room temperature and stirred for 45 minutes. The reaction mixture was cooled to 0° C. and dimethyl carbonate (1.40 mL, 16.6 mmol) was added. The mixture was then warmed room temperature and stirred for 6 hours. The reaction was quenched with water and the organics extracted with ethyl acetate (100 mL). The organic layer was washed with saturated ammonium chloride (50 mL×2), water (50 mL×2) and brine (50 mL×2), dried over anhydrous sodium sulfate and concentrated under reduced pressure. The residue was purified by prep-TLC to give the title compound as a yellow oil, which was confirmed as a mixture of stereo isomers (178 mg, Yield: 45%). $R_f$=0.3 (50:1 petroleum ether/ethyl acetate); $^1$H NMR (400 MHz, CDCl$_3$) (Major isomer) δ 3.78 (s, 3H), 3.19 (t, J=6.4 Hz, 1H), 2.18 (t, J=6.4 Hz, 2H), 1.55-1.41 (m, 7H), 1.28 (s, 3H), 1.11 (5, 3H), 0.96 (s, 3H) ppm; Mass spectrum (ESI+ve) m/z 239 (M+H$^+$).

Examples 8b and 8c (±)-(1R,2R,3aR,7aS)-methyl 1-hydroxy-4,4,7a-trimethyloctahydro-1H-indene-2-carboxylate (8b) and (±)-(1S,2R,3aS,7aR)-methyl 1-hydroxy-4,4,7a-trimethyloctahydro-1H-indene-2-carboxylate (8c)

To an ice-cooled solution of the product of Example 8a (100 mg, 0.42 mmol) in tetrahydrofuran (5.2 mL) and methanol (0.6 mL) at 0° C. was added sodium borohydride (16 mg, 0.42 mmol) and the reaction mixture was stirred for 4 hours. The reaction was quenched with 1N hydrochloric acid and extracted with diethyl ether (50 mL). The organic layer was washed with brine (30 mL×2), dried over anhydrous sodium sulfate and concentrated under reduced pressure. The residue was purified by prep-TLC to give the title compound (8b) as a light yellow oil (32 mg, Yield: 32%). $R_f$=0.5 (10:1 petroleum ether/ethyl acetate); $^1$H NMR (400 MHz, CDCl$_3$) δ 3.83-3.82 (m, 1H), 3.70 (s, 3H), 3.06-2.98 (m, 1H), 2.97 (bs, 1H),1.97-1.87 (m, 2H), 1.53-1.50 (m, 2H), 1.43-1.36 (m, 2H), 1.30-1.24 (m, 2H), 1.18-1.13 (m, 1H), 1.15 (s, 3H), 1.03 (s, 3H), 0.81 (s, 3H); $^{13}$C NMR (100 MHz, CDCl$_3$) δ 175.9, 82.6, 51.8, 51.5, 43.6, 43.5, 34.0, 31.8, 30.9, 29.7, 28.5, 25.5, 25.0, 18.5 ppm; Mass spectrum (ESI+ve) m/z 241 (M+H$^+$). The title compound 8c light yellow oil (28 mg, Yield: 28%). $R_f$=0.4 (10:1 petroleum ether/ethyl acetate); $^1$H NMR (400 MHz, CDCl$_3$) δ 3.78 (d, J=8.8 Hz, 1H), 3.71 (s, 3H), 2.74-2.67 (m, 1H), 2.12 (bs, 1H), 1.89-1.81 (m, 2H), 1.53-1.40 (m, 3H); 1.31-1.18 (m, 3H), 1.14 (s, 3H), 1.09-1.03 (m, 1H), 1.02 (s, 3H), 0.79 (s, 3H); $^{13}$C NMR (100 MHz, CDCl$_3$) δ 176.8, 84.4, 52.0, 50.8, 46.9, 43.6, 33.9, 31.8, 30.3, 28.3, 26.8, 26.1, 24.4, 18.2 ppm; Mass spectrum (ESI+ve) m/z 241 (M+H$^+$).

Example 8

(±)-(3aS,7aS)-methyl 3a,7,7-trimethyl-3a,4,5,6,7,7a-hexahydro-1H-indene-2-carboxylate To a solution of the product of Example 8b (50 mg, 0.21 mmol) in dichloromethane (2 mL) was drop wise added thionyl chloride (64 mL) and pyridine (50 mL) and the reaction mixture was refluxed for 4 hours. Dichloromethane (30 mL) was added and the organic phase was washed with water (30 ml×2) and brine (30 ml×2), dried over anhydrous sodium sulfate and concentrated under reduced pressure. Purification of the residue by silica column chromatography gave 44 mg of a colorless oil which was further purified by prep-TLC to afford the title compound as a colorless oil (23 mg, Yield: 48%). $R_f$=0.6 (100:1 petroleum ether/ethyl acetate); $^1$H NMR (400 MHz, CDCl$_3$) δ 6.56 (t, J=1.2 Hz, 1H), 3.72 (s, 3H), 2.49-2.47 (m, 1H), 2.44-2.40 (m, 1H), 1.70-1:68 (m, 1H), 1.51-1.27 (m, 5H), 1.24 (s, 3H), 1.14-1.10 (m, 1H), 1.02 (s, 3H), 0.91 (s, 3H) ppm; Mass spectrum (ESI+ve) m/z 223 (M+H$^+$).

Example 9

(±)-(3R,3aS,7aS)-3,3a,7,7-tetramethyloctahydro-1H-inden-1-one

To a solution of the product of Example 1 (400 mg, 2.08 mmol) in methanol (5 mL) was added 10% Pd/C (80 mg) and the mixture was stirred under an atmosphere of hydrogen for 24 hours. The reaction was suction filtered and the filtrate concentrated under reduced pressure to afford the title compound as a colorless oil (364 mg, Yield: 91%). $R_f$=0.9 (20:1 petroleum ether/ethyl acetate); $^1$H NMR (400 MHz, CDCl$_3$) δ 2.32 (dd, J=18.4, 8.0 Hz, 1H), 1.91 (dd, J=18.0, 12.0 Hz, 1H), 1.85-1.77 (m, 1H), 1.65-1.46 (m, 3H), 1.30-1.06 (m, 9H), 1.04 (s, 3H), 1.02-0.99 (m, 1H), 0.96 (d, J=6.4 Hz, 3H). $^{13}$C NMR (100 MHz, CDCl$_3$) δ 218.0, 65.7, 44.2, 42.3, 38.9, 36.3, 33.1, 29.8, 29.5, 27.7, 25.3, 18.3, 12.3 ppm; Mass spectrum (ESI+ve) m/z 217 (M+Na$^+$).

Example 10

4,4,7a-trimethyl-2,4,5,6,7,7a-hexahydro-1H-inden-2-ol

To a solution of the product of Example 6 (120 mg, 0.67 mmol) in dry tetrahydrofuran (12.0 mL) at 0° C. was added lithium aluminum hydride (77 mg, 2 mmol) in one portion. The resulting mixture was stirred at 0° C. for 1 hour. Water (10 mL) was added to the solution and the organics extracted with ethyl acetate (50 mL×2). The organic phase was washed with brine (50 mL), dried over anhydrous sodium sulfate and concentrated under reduced pressure. The residue was purified by silica gel column chromatography (eluent: petroleum ether/ethyl acetate=8/1) to afford the title compound as a colorless oil (46 mg, Yield: 38%). $R_f$=0.4 (5:1 petroleum ether/ethyl acetate); $^1$H NMR (400 MHz, CDCl$_3$) δ 5.34 (s, 1H), 4.89 (t, J=7.2 Hz, 1H), 2.24 (dd, J=12.0, 6.4 Hz, 1H), 1.78-1.65 (m, 2H), 1.50-1.39 (m, 4H), 1.33-1.11 (m, 2H), 1.17 (s, 3H), 1.03 (s, 3H), 1.01 (s, 3H) ppm; Mass spectrum (ESI+ve) m/z 163 (M−H$_2$O+H$^+$).

Example 11

2-methoxy-4,4,7a-trimethyl-2,4,5,6,7,7a-hexahydro-1H-indene

To a stirred solution of the product of Example 10 (46 mg, 0.25 mmol) in dichloromethane (6.0 mL) at 0° C. was added 1,8-bis(dimethylamino)naphthalene (535 mg, 2.5 mmol), followed by trimethyloxonium tetrafluoroborate (370 mg, 2.5 mmol). The resulting mixture was warmed to room temperature and stirred for 2 hours. The reaction was quenched by the addition of saturated aqueous sodium bicarbonate (15 mL) and the organic phase was separated. The aqueous phase was extracted with dichloromethane (60 mL×2). The combined organic phase was washed with citric acid (60 mL), dried over anhydrous sodium sulfate and concentrated in vacuo. The residue was purified by silica gel column chromatography (eluent: petroleum ether/ethyl acetate=80/1) to afford the title compound as a colorless oil (33 mg, Yield: 69%). $R_f$=0.6 (50:1 hexanes/ethyl acetate);

¹H NMR (400 MHz, CDCl₃) δ 5.44 (d, J=0.8 Hz, 1H), 4.47 (dt, J=0.8, 7.6 Hz, 1H), 3.33 (s, 3H), 2.16 (dd, J=12.0, 6.4 Hz, 1H), 1.78-1.67 (m, 2H), 1.50-1.33 (m, 3H), 1.32-1.17 (m, 2H), 1.17 (s, 3H), 1.11 (s, 3H), 1.07 (s, 3H) ppm; Mass spectrum (APCI+ve) m/z 163 (M–CH₃OH+H⁺).

Example 12

7,7-dimethyl-2,3,4,5,6,7-hexahydro-1H-isoindol-1-one

Example 12a ethyl 6,6-dimethyl-2-(trifluoromethylsulfonyloxy)cyclohex-1-enecarboxylate To a stirred suspension of sodium hydride (0.8 g, 20 mmol) in dry diethyl ether (30 mL) under an argon atmosphere at −20° C. was drop wise added ethyl 2,2-dimethyl-6-oxocyclohexanecarboxylate (1.98 g, 10 mmol). The mixture was stirred at −20° C. for 30 minutes and then at room temperature for 30 minutes. The mixture was cooled again to −20° C. and trifluoromethansulfonic anhydride (2.5 ml, 15 mmol) was added drop wise. The reaction was stirred at −20° C. for 1 hour, and then warmed gradually to room temperature and stirred for 1 hour. The reaction was cooled to 0° C. and diethyl ether (20 mL) was added. Water (50 mL) was added slowly and the layers were separated. The aqueous layer was extracted with diethyl ether (50 mL×3). The combined organic phase was washed with saturated aqueous sodium bicarbonate (100 mL) and brine (100 mL), dried over anhydrous sodium sulfate and concentrated under reduced pressure. Purification of the residue by silica gel column chromatography (eluent: petroleum ether/ethyl acetate=50/1) gave 2.6 g of a light yellow liquid that was repurified by silica gel column chromatography (eluent: hexanes/ethyl acetate=1/0→500/1) to afford the title compound (900 mg, Yield: 27%). R_f=0.6 (20:1 petroleum ether/ethyl acetate); ¹H NMR (400 MHz, CDCl₃) δ 4.26 (q, J=7.6 Hz, 2H), 2.37 (t, J=6.8 Hz, 2H), 1.84-1.80 (m, 2H), 1.52-1.48 (m, 2H), 1.32 (t, J=7.2 Hz, 3H), 1.19 (s, 6H) ppm; Mass spectrum (ESI+ve) m/z 331 (M+H⁺).

Example 12b ethyl 2-cyano-6,6-dimethylcyclohex-1-enecarboxylate

To a stirred solution of the product of Example 12a (802 mg, 2.43 mmol) in dimethylformamide (20 mL) was sequentially added zinc cyanide (426 mg, 3.65 mmol), water (0.5 mL) and tetrakis(triphenylphosphine)palladium(0) (560 mg, 0.48 mmol). The reaction was heated to 100° C. under argon for 5 hours. The reaction was cooled to room temperature and water (200 mL) was added. The mixture was extracted with ethyl acetate (150 mL×4) and the combined organic phase was washed with brine (200 mL×2), dried over anhydrous sodium sulfate and concentrated in vacuo. The crude product was purified by silica gel column chromatography (eluent: petroleum ether/ethyl acetate=50/1→20/1) to afford the title compound as a colorless liquid (360 mg, Yield: 71%). R_f=0.3 (20:1 petroleum ether/ethyl acetate); ¹H NMR (400 MHz, CDCl₃) δ 4.32 (q, J=7.2 Hz, 2H), 2.34-2.30 (m, 2H), 1.75-1.72 (m, 2H), 1.53-1.50 (m, 2H), 1.36 (t, J=7.2 Hz, 3H), 1.19 (s, 6H) ppm; Mass spectrum (ESI+ve) m/z 208 (M+H⁺).

Example 12

7,7-dimethyl-2,3,4,5,6,7-hexahydro-1H-isoindol-1-one

To a stirred solution of the product of Example 12b (287 mg, 1.38 mmol) in THF (15 mL) was added Raney nickel (~0.5 g). aqueous ammonia was added to make the reaction mixture become basic (pH-10, 8.5 ml). The reaction mixture was stirred at room temperature under hydrogen for 2 days. The reaction was filtered and the filtrate concentrated under reduced pressure. The residue was purified by silica gel column chromatography (eluent: dichloromethane/methanol=20/1→10/1) and then repurified by silica gel column chromatography (eluent: petroleum ether/ethyl acetate=1/1) and then repurified again (eluent: dichloromethane/methanol=40/1) to give the title compound as white crystals (68 mg, Yield: 30%). Mp=186-188° C.; R_f=0.6 (20:1 dichloromethane/Methanol); ¹H NMR (400 MHz, CDCl₃) δ 6.07 (bs, 1H), 3.75 (s, 2H), 2.24-2.20 (m, 2H), 1.76-1.70 (m, 2H), 1.52-1.49 (m, 2H), 1.25 (s, 6H) ppm; Mass spectrum (ESI+ve) m/z 166 (M+H⁺).

Example 13

2,7,7-trimethyl-2,3,4,5,6,7-hexahydro-1H-isoindol-1-one

To a solution of the product of Example 12 (100 mg, 0.61 mmol) in dry dichloromethane (10 mL) at 0° C. under argon was sequentially added 1,8-bis(dimethylamino)naphthalene (1.44 g, 6.71 mmol) and trimethyloxonium tetrafluoroborate (812 mg, 5.49 mmol) at 0° C. The reaction was stirred at room temperature for 4 hours. The reaction mixture was concentrated under reduced pressure and the residue purified by prep-TLC to give the title compound as light pink solid (6 mg, Yield: 5%). Mp=40-43° C.; R_f=0.5 (1:1 petroleum ether/ethyl acetate); ¹H NMR (400 MHz, CDCl₃) δ 3.69 (s, 2H), 2.98 (s, 3H), 2.20 (t, J=6.0 Hz, 2H), 1.73-1.70 (m, 2H), 1.51-1.48 (m, 2H), 1.24 (s, 6H) ppm; Mass spectrum (ESI+ve) m/z 180 (M+H⁺).

Example 14

(±)-(3aR,7aS)-3,3a,7,7-tetramethyl-3a,4,5,6,7,7a-hexahydro-1H-inden-1-one oxime

To a solution of the product of Example 1 (76.8 mg, 0.4 mmol) in pyridine (3.0 mL) was added hydroxylamine hydrochloride (294 mg, 4.0 mmol) and the mixture was heated to reflux for 6 hours. The reaction was concentrated under reduced pressure and the residue purified by silica gel column chromatography to give the title compound as a white solid (58 mg, Yield: 70%). Mp=101-102° C.; R_f=0.6 (10:1 petroleum ether/ethyl acetate); ¹H NMR (400 MHz, CDCl₃) δ 6.31 (s, 1H), 2.15 (s, 1H), 1.84 (s, 3H), 1.84-1.81 (m, 1H), 1.70-1.49 (m, 1H), 1.41-1.48 (m, 4H), 1.07 (s, 3H), 1.06 (s, 3H), 0.76 (s, 3H) ppm; Mass spectrum (ESI+ve) m/z 208 (M+H⁺).

Example 15

(±)-(1 S,3aR,7aS)-3,3a,7,7-tetramethyl-3a,4,5,6,7,7a-hexahydro-1H-inden-1-ol

To a solution of the product of Example 1 (100 mg, 0.52 mmol) in ethanol (5 mL) at 0° C. was added cerium trichloride heptahydrate (233 mg, 0.62 mmol) and sodium borohydride (23 mg, 0.62 mmol). The mixture was warmed to room temperature stirred overnight. The reaction was quenched with water and then the organics were extracted with ethyl acetate (20 mL×3). The combined organic phase was washed with water (20 mL) and brine (20 mL), dried over anhydrous sodium sulfate and then concentrated under reduced pressure. The residue was purified by silica gel column chromatography to afford the title compound as a white solid (20 mg, Yield: 20%). Mp=55-56° C.; $R_f$=0.5 (10:1 petroleum ether/ethyl acetate); $^1$H NMR (400 MHz, CDCl$_3$) δ 5.25 (d, J=1.2 Hz, 1H), 4.55 (d, J=7.6 Hz, 1H), 1.62 (t, J=1.6 Hz, 3H), 1.59-1.45 (m, 1H), 1.40-1.23 (m, 6H), 1.17 (s, 3H), 1.09 (s, 3H), 1.07 (s, 3H), 0.96-0.88 (m, 1H) ppm; Mass spectrum (ESI+ve) m/z 177 (M–H$_2$O+H$^+$).

Example 16

(±)-(3R,3aS,7aS)-3,3a,7,7-tetramethyloctahydro-1H-inden-1-one oxime

To a solution of the product of Example 9 (77.6 mg, 0.4 mmol) in pyridine (3.0 mL) was added hydroxylamine hydrochloride (294 mg, 4.0 mmol) and the mixture was heated to reflux for 6 hours. The reaction mixture was concentrated under reduced pressure and the residue was purified by silica gel column chromatography to afford the title compound as a white solid (51 mg, Yield: 61%). Mp=144-145° C.; $R_f$=0.6 (10:1 petroleum ether/ethyl acetate); $^1$H NMR (400 MHz, CDCl$_3$) δ 6.89 (s, 1H), 2.72 (dd, J=18.4, 8.0 Hz, 1H), 2.11-2.04 (m, 2H), 1.62-1.31 (m, 4H), 1.39 (s, 3H), 1.38-1.17 (m, 5H), 1.13 (s, 3H), 1.10-0.98 (m, 1H), 0.89 (d, J=6.8 Hz, 3H) ppm; Mass spectrum (ESI+ve) m/z 210 (M+H$^+$).

Example 17

7,7-dimethyloctahydro-1H-isoindol-1-one

To liquid ammonia (20 mL) at −78° C. was added lithium (~20 mg). The solution became deep blue after stirring for 5 minutes. Then a solution of the product of Example 12 (30 mg, 0.18 mmol) in tetrahydrofuran (1.5 mL) was added slowly. The reaction mixture was stirred at −78° C. for 1 hour and then warmed gradually to room temperature and stirred overnight to evaporate the ammonia. Saturated aqueous ammonium chloride (20 mL) was added and the resulting mixture was extracted with dichloromethane (15 mL×4). The combined organic phase was dried over anhydrous sodium sulfate and concentrated under reduced pressure. The residue was purified by silica gel column chromatography to give the title compound as a light yellow solid (26 mg, Yield: 87%). Mp=141-148° C.; $R_f$=0.5 (10:1 dichloromethane/ethyl acetate); $^1$H NMR (400 MHz, CDCl$_3$+D$_2$O) (Major. trans) δ 3.28-3.24 (m, 1H), 2.90-2.84 (m, 1H), 2.12-2.03 (m, 1H), 1.87-1.83 (m, 1H), 1.66-1.58 (m, 2H), 1.53-1.39 (m, 3H), 1.26 (s, 3H), 1.19-1.11 (m, 1H), 0.97 (s, 3H); (Minor, cis) δ3.28-3.24 (m, 0.4H), 2.3-2.90 (m, 0.4H), 2.57-2.49 (m, 1H), 2.04 (d, J=7.6 Hz), 1.87-1.83 (m, 1H), 1.66-1.58 (m, 0.8H), 1.53-1.39 (m, 0.8H), 1.26-1.11 (m, 0.8 Hz), 1.18 (s, 1.4H), 1.04 (s, 1.5H) ppm; Mass spectrum (ESI+ve) m/z 168 (M+H$^+$).

Example 18

(±)-(1S,3aS,7aR)-4,4,7a-trimethyloctahydro-1H-inden-1-ol

To a stirred solution of the product of Example 5 (50 mg, 0.28 mmol) cooled to 0° C. in methanol/tetrahydrofuran (0.5 mL/3.5 mL) was added sodium borohydride (13 mg, 0.34 mmol). The reaction mixture was warmed to room temperature and stirred for 3 hours. The reaction was quenched with 5% hydrochloric acid (3 mL) and the organics were extracted with ethyl acetate (50 mL). The organic layer was washed with brine (30 mL×2), dried over anhydrous sodium sulfate and concentrated under reduced pressure. The residue was purified by silica gel column chromatography to afford the title compound as a white solid (46 mg, Yield: 90%). Mp=59.7-60.8° C.; $R_f$=0.2 (20:1 petroleum ether/ethyl acetate); $^1$H NMR (400 MHz, CDCl$_3$) δ 3.66 (t, J=8.8 Hz, 1H), 2.02-1.97 (m, 1H), 1.60-1.44 (m, 5H), 1.40-1.27 (m, 3H), 1.18-1.10 (m, 3H), 1.13 (s, 3H), 1.04 (s, 3H), 0.80 (s, 3H); $^{13}$C NMR (100 MHz, CDCl$_3$) δ 82.8, 52.1, 42.7, 34.1, 32.0, 30.5, 28.9, 28.4, 25.4, 24.6, 22.6, 18.4 ppm; Mass spectrum (ESI+ve) m/z 165 (M–H$_2$O+H$^+$).

Example 19

(±)-(3aR,7aS)-3,3a,7,7-tetramethyl-3a,4,5,6,7,7a-hexahydro-O-methyl oxime

Sodium hydride (9.6 mg, 0.24 mmol) was added to a solution of the product of Example 14 (41 mg, 0.2 mmol) in tetrahydrofuran (3 mL) at 0° C., and the resulting solution was allowed to warm to room temperature and stirred for 2 hours. Then, methyl iodide (0.05 mL, 1.0 mmol) was added drop wise and the resulting mixture was stirred for 2 hours. Water (20 mL) was added and the mixture was extracted with ethyl acetate (60 mL×2) and the combined organic phase was washed with brine (60 mL), dried over anhydrous sodium sulfate and concentrated under reduced pressure. The residue was purified by silica gel column chromatography to give the title compound as a colorless oil (20 mg, Yield: 45%). $R_f$=0.7 (10:1 petroleum ether/ethyl acetate); $^1$H NMR (400 MHz, CDCl$_3$) δ 6.20 (s, 1H), 3.86 (s, 3H), 2.13 (s, 1H), 1.84 (s, 3H), 1.51-1.24 (m, 6H), 1.10 (s, 3H), 1.05 (s, 3H), 0.75 (s, 3H) ppm; Mass spectrum (ESI+ve) m/z 222 (M+H$^+$).

Example 20

(±)-(1R,7aS)-1,4,4,7a-tetramethyl-5,6,7,7a-tetrahydro-1H-inden-2(4H)-one

To a solution of the product of Example 6 (98 mg, 0.55 mmol) in dry tetrahydrofuran (4.0 mL) at 0° C. was added lithium diisopropylamide (0.42 mL, 0.84 mmol) and then the mixture was allowed to warmed to room temperature the solution was stirred for 1 hour. The mixture was cooled to −78° C. and methyl iodide (0.27 mL, 5.5 mmol) was added. The solution was allowed to gradually warm to room temperature and stirred for overnight. The mixture was poured into saturated aqueous ammonium chloride and then it was extracted with ethyl acetate (75 mL). The organic layer was washed by saturated aqueous sodium bicarbonate (50 mL×2) and brine (50 mL×2), dried over anhydrous sodium sulfate and concentrated under reduced pressure. The residue was purified by silica gel column chromatography to afford the title compound as a colorless oil (70 mg, Yield: 76%). $R_f$=0.9 (20:1 petroleum ether/ethyl acetate); $^1$H NMR (400 MHz, CDCl$_3$) δ 5.81 (s, 1H), 2.16 (q, J=8.0 Hz, 1H), 1.97-1.85 (m, 1H), 1.70-1.59 (m, 3H), 1.40-1.29 (m, 5H), 1.27 (s, 3H), 1.20 (s, 3H), 1.05 (d, J=7.6 Hz, 3H) ppm; Mass spectrum (ESI+ve) m/z 193 (M+H$^+$).

Example 21

1,1,4,4,7a-pentamethyl-5,6,7,7a-tetrahydro-1H-inden-2(4H)-one

To a solution of the product of Example 20 (30 mg, 0.15 mmol) in tetrahydrofuran (1 mL) 0° C. was added lithium diisopropylamide (0.14 mL, 0.28 mmol) and then the mixture was allowed to warmed to room temperature and the solution was stirred for 1 hour. The mixture was cooled to −78° C. and methyl iodide (0.10 mL, 1.8 mmol) was added. The solution was allowed to gradually warm to room temperature stirred at room temperature overnight. The mixture was poured into saturated aqueous ammonium chloride and then the organics were extracted with ethyl acetate (25 mL). The organic layer was washed with saturated aqueous sodium bicarbonate (50 mL×2) and brine (50 mL×2), dried over anhydrous sodium sulfate and concentrated under reduced pressure. The residue was purified by silica gel column chromatography to afford the title compound as a yellow solid (20 mg, Yield: 64%). Mp=<15° C.; $R_f$=0.4 (10:1 petroleum ether/ethyl acetate); $^1$H NMR (400 MHz, CDCl3) δ 5.80 (s, 1H), 1.90-1.86 (m, 1H), 1.65-1.60 (m, 3H), 1.48-1.34 (m, 2H), 1.26 (s, 3H), 1.21 (s, 3H), 1.20 (s, 3H), 1.01 (s, 6H) ppm; Mass spectrum (EI+ve) m/z 206 (M$^+$).

Example 22

(±)-((3aS,7aS)-3a,7,7-trimethyl-3a,4,5,6,7,7a-hexahydro-1H-inden-2-yl)methanol To a solution of the product of Example 8 (100 mg, 0.45 mmol) in tetrahydrofuran (12 mL) at 0° C. was added lithium aluminum hydride (34 mg, 0.90 mmol) and the mixture was stirred for 3 hours. The reaction was quenched with and water and then the organics were extracted with ethyl acetate (100 mL). The organic layer was washed with water (50 mL×2) and brine (50 mL×2), dried over anhydrous sodium sulfate and concentrated under reduced pressure. Purification of the residue by silica gel column chromatography gave the title compound as a colorless oil (68 mg, Yield: 78%). $R_f$=0.2 (10:1 petroleum ether/ethyl acetate); $^1$H NMR (400 MHz, CDCl$_3$) δ 5.44 (s, 1H), 4.13 (s, 2H), 2.22-2.17 (m, 2H), 1.67-1.62 (m, 1H), 1.52-1.45 (m, 2H), 1.40-1.36 (m, 2H), 1.32-1.25 (m, 2H), 1.18 (s, 3H), 1.17-1.09 (m, 1H), 1.02 (s, 3H), 0.83 (s, 3H); $^{13}$C NMR (100 MHz, CDCl$_3$) δ 139.9, 139.2, 62.4, 56.2, 45.1, 35.3, 35.2, 35.1, 32.0, 31.0, 29.4, 26.8, 18.3 ppm; Mass spectrum (ESI+ve) m/z 177 (M–H$_2$O+H$^+$).

Example 23

(±)-(3aS,7aS)-2-(methoxymethyl)-3a,7,7-trimethyl-3a,4,5,6,7,7a-hexahydro-1H-indene To a stirred solution of the product of Example 22 (54 mg, 0.28 mmol) in dichloromethane (8 mL) at 0° C. was added 1,8-bis(dimethylamino)naphthalene (600 mg, 2.8 mmol) and trimethyloxonium tetrafluoroborate (414 mg, 2.8 mmol). The mixture was warmed to room temperature and stirred for 4 hours. The reaction was quenched with saturated aqueous sodium bicarbonate (20 mL) and then extracted with dichloromethane (50 mL). The organic layer was washed by 5% hydrochloric acid (30 mL×3) and brine (30 mL×2), dried over anhydrous sodium sulfate and concentrated under reduced pressure. Purification of the residue by silica gel column chromatography afforded the title compound as a colorless oil (49 mg, Yield: 84%). $R_f$=0.5 (50:1 petroleum ether/ethyl acetate); $^1$H NMR (400 MHz, CDCl$_3$) δ 5.39 (s, 1H), 3.83 (s, 2H), 3.25 (s, 3H), 2.14-2.11 (m, 2H), 1.58 (dd, J=10.0, 9.2 Hz, 1H), 1.41-1.37 (m, 2H), 1.32-1.17 (m, 3H), 1.11 (s, 3H), 1.10-1.01 (m, 1H), 0.94 (s, 3H), 0.81 (s, 3H); $^{13}$C NMR (100 MHz, CDCl$_3$) δ 140.4, 136.0, 70.7, 57.0, 55.1, 44.2, 34.4, 34.3, 34.2, 30.9, 30.0, 28.4, 25.8, 17.3 ppm; Mass spectrum (EI+ve) m/z 208 (M)$^+$.

Example 24

(±)-(1S,3aS,7aR)-1-methoxy-4,4,7a-trimethyloctahydro-1H-indene

To a stirred solution of the product of Example 18 (50 mg, 0.28 mmol) cooled to 0° C. in methanol/tetraydrofuran (0.5 mL/3.5 mL) was added sodium borohydride (13 mg, 0.34 mmol). Then the solution was warmed to room temperature and stirred for 3 hours. The reaction was quenched with 5% hydrochloric acid (3 mL) and the mixture was extracted with ethyl acetate (50 mL). The organic layer was washed with brine (30 mL×2), dried over anhydrous sodium sulfate and concentrated under reduced pressure. The residue was purified by silica gel column chromatography to give the title compound as a white solid (46 mg, Yield: 90%). Mp=59.7-60.8° C.; $R_f$=0.2 (20:1 petroleum ether/ethyl acetate); $^1$H NMR (400 MHz, CDCl$_3$) δ 3.66 (t, J=9.0 Hz, 1H), 2.02-1.97 (m, 1H), 1.60-1.44 (m, 5H), 1.40-1.27 (m, 3H), 1.18-1.10 (m, 3H), 1.13 (s, 3H), 1.04 (s, 3H), 0.80 (s, 3H); $^{13}$C NMR (100 MHz, CDCl$_3$) δ 82.8, 52.1, 42.7, 34.1, 32.0, 30.5, 28.9, 28.4, 25.4, 24.6, 22.6, 18.4 ppm; Mass spectrum (ESI+ve) m/z 165 (M–H$_2$O+H$^+$).

Example 25

(±)-(3aS,7aS)-methyl 3a,7,7-trimethyloctahydro-1H-indene-2-carboxylate

To a solution of the product of Example 8 (78 mg, 0.35 mmol) in methanol (8 mL) was added Pd/C (~50 mg). Then the mixture was stirred under an atmosphere of hydrogen overnight. The reaction mixture was filtered and the filtrate concentrated under reduced pressure. The residue was purified by silica gel column chromatography to give the title compound as a colorless oil (55 mg, Yield: 71%). $R_f$=0.6 (100:1 petroleum ether/ethyl acetate); $^1$H NMR (400 MHz, CDCl$_3$) δ 3.66 (s, 3H), 2.78-2.74 (m, 1H), 1.96 (t, J=9.6 Hz, 2H), 1.77 (d, J=9.6 Hz, 2H), 1.55-1.35 (m, 5H), 1.20-1.15 (m, 2H), 1.11 (s, 3H), 1.02 (s, 3H), 0.84 (s, 3H); $^{13}$C NMR (100 MHz, CDCl$_3$) δ 177.70, 55.60, 51.68, 45.96, 40.54, 39.49, 34.34, 33.97, 32.78, 31.99, 31.63, 28.89, 27.87, 19.39 ppm; Mass spectrum (ESI+ve) m/z 225 (M+H$^+$).

Example 26

(±)-((3aS,7aS)-3a,7,7-trimethyloctahydro-1H-inden-2-yl)methanol

To a solution of the product of Example 25 (70 mg, 0.31 mmol) in tetrahydrofuran (8 mL) at 0° C. was added lithium aluminum hydride (24 mg, 0.62 mmol). The mixture was stirred for 3 hours and then the reaction was quenched with water. The organics were extracted with ethyl acetate, dried over anhydrous sodium sulfate and concentrated under reduced pressure. The residue was purified by silica gel column chromatography to afford the title compound as a colorless oil (54 mg, Yield: 89%). $R_f$=0.4 (5:1 petroleum ether/ethyl acetate); $^1$H NMR (400 MHz, CDCl$_3$) δ 3.58-3.50 (m, 2H), 2.18-2.10 (m, 1H), 1.84-1.80 (m, 1H), 1.67 (t, J=12.4 Hz, 1H), 1.56-1.49 (m, 1H), 1.40-1.23 (m, 6H), 1.21-1.12 (m, 3H), 1.12 (s, 3H), 1.03 (s, 3H), 0.84 (s, 3H); $^{13}$C NMR (100 MHz, CDCl$_3$) δ 68.8, 55.6, 46.1, 40.2, 38.1, 35.7, 34.7, 32.9, 32.0, 31.9, 29.1, 28.6, 19.6 ppm; Mass spectrum (ESI+ve) m/z 179 (M−H$_2$O+H$^+$).

Example 27

7,7-dimethyl-5,6,7,7a-tetrahydro-1H-inden-2(4H)-one

Example 27a 2-(hydroxymethylene)-6-methylcyclohexanone

To an ice cold suspension of powdered sodium methoxide (24.5 g, 454 mmol) in toluene (450 mL) was added 2-methylcyclohexanone (60 g, 178 mmol) and ethyl formate (79.2 g, 1069 mmol). The mixture was stirred at room temperature overnight. Ice water and toluene were added and the phases were separated. The organic phase was washed with 10% sodium hydroxide (100 mL×2). The aqueous layer was acidified with dilute hydrochloric acid to pH ~3 and then extracted with diethyl ether (200 mL×3). The combined organic layer was washed with water (100 mL×2) and brine (100 mL×2) and dried over anhydrous sodium sulfate. Concentration under reduced pressure gave the title compound as a light orange oil (50 g, Yield: 66%).

Example 27b 2-(isopropoxymethylene)-6-methylcyclohexanone

To a solution of the product of Example 27a (50 g, 357 mmol) in acetone (500 mL) was added potassium carbonate (74.1 g, 536 mmol) and 2-iodopropane (45 mL, 446 mmol) and the reaction mixture was refluxed overnight. After concentration under reduced pressure and the residue was extracted with ether (800 mL) and the organic layer was washed with 5% aqueous sodium hydroxide (100 mL×2), brine (100 mL), dried over anhydrous sodium sulfate, and concentrated under reduced pressure to give the title compound as a light yellow oil (55 g, Yield: 84%), which was used in the next step without any further purification.

Example 27c (E)-6-(tert-butoxymethylene)-2,2-dimethylcyclohexanone and (E)-6-(isopropoxymethylene)-2,2-dimethylcyclohexanone To a solution of potassium tert-butoxide (106 g, 945 mmol) in tetrahydrofuran (550 mL) cooled to 0° C. was added the product of Example 27b (55 g, 302 mmol). The mixture was stirred at 0° C. for 10 minutes and then methyl iodide (141 g, 993 mmol) was added. The mixture began to reflux and when reflux ceased the cooling bath was removed and the mixture was then stirred at room temperature for 1 hour. The mixture was filtered and the filtrate concentrated under reduced pressure. The residue was diluted with diethyl ether (600 mL), washed by 10% aqueous sodium hydroxide (100 mL×2), brine (100 mL), dried over anhydrous sodium sulfate and concentrated under reduced pressure to give 45 g of an orange oil. Purification of 6.0 g of material by silica gel column chromatography (eluent: petroleum ether/ethyl acetate=1/0→30/1 gave a 4:1 mixture of (E)-6-(tert-butoxymethylene)-2,2-dimethylcyclohexanone and (E)-6-(isopropoxymethylene)-2,2-dimethylcyclohexanone as a colorless oil (3.52 g) $^1$H NMR (400 MHz, CDCl$_3$) Major: δ 7.58 (t, J=2.0 Hz, 1H), 2.41-2.39 (m, 2H), 1.70-1.66 (m, 4H), 1.35 (s, 9H), 1.12 (s, 6H); Minor: δ 7.37 (t, J=1.8 Hz, 1H), 4.23-4.15 (m, 1H), 2.41-2.39 (m, 2H), 1.70-1.66 (m, 4H), 1.29 (d, J=6.4 Hz, 6H), 1.12 (s, 6H).

Example 27d 2,2-dimethylcyclohexanone

To the product of Example 27c (3.52 g, 16.7 mmol) was added a solution of 20% aqueous sodium hydroxide (28 mL). The resulting mixture was heated to reflux for 24 hours then ethanol (20 mL) was added and refluxing was continued for additional 45 minutes. The mixture was diluted with water (50 mL) and then it was extracted with petroleum ether (50 mL×4). The combined organic phase was washed with brine (100 mL), dried over anhydrous sodium sulfate and concentrated under reduced pressure to give the title compound as light yellow liquid (0.99 g, Yield: 47%). $^1$H NMR (400 MHz, CDCl$_3$) δ 2.39 (t, J=6.8 Hz, 2H), 1.85-1.80 (m, 2H), 1.75-1.71 (m, 2H), 1.67-1.62 (m, 2H), 1.11 (s, 6H) ppm.

Example 27e 6-allyl-2,2-dimethylcyclohexanone

Potassium t-butoxide (393 mg, 3.5 mmol) was added to t-butanol (5 mL) in one portion at room temperature. The mixture was stirred for 10 minutes under argon. A solution of the product of Example 27d (441 mg, 3.5 mmol) in t-butanol (2 mL) was added slowly. After stirring for 10 minutes, allyl bromide (0.46 ml, 5.25 mmol) was added and the mixture was stirred at room temperature overnight. Another portion of potassium t-butoxide (39 mg, 0.35 mmol) was added and the reaction was heated to reflux for 1 hour. The mixture was partitioned between diethyl ether (30 mL) and water (30 mL). The aqueous layer was extracted with diethyl ether (30 mL×2) and the combined organic phase were dried over anhydrous sodium sulfate and concentrated under reduced pressure. Purification of the residue by silica gel column chromatography afforded the title compound as a colorless oil contaminated with 2,2-diallyl-6,6-dimethylcyclohexanone (256 mg). This material was used directly for the next step without further purification. $^1$H NMR (400 MHz, CDCl$_3$) Major: δ 5.83-5.73 (m, 1H), 5.04-4.97 (m, 2H), 2.64-2.49 (m, 2H), 2.15-2.09 (m, 1H), 1.96-1.65 (m, 5H), 1.29-1.25 (m, 1H), 1.19 (s, 3H), 1.05 (s, 3H); Minor: δ 5.67-5.57 (m, 2H), 5.04-4.97 (m, 4H), 2.41-2.32 (m, 2H), 2.24-2.18 (m, 2H), 1.96-1.54 (m, 6H), 1.10 (s, 6H) ppm.

Example 27f 2,2-dimethyl-6-(2-oxopropyl)cyclohexanone

A 50 ml round-bottom-flask was charged with palladium dichloride (14 mg, 0.076 mmol), cupric acetate hydrate (76 mg, 0.38 mmol), dimethylacetamide (3.5 mL) and water (0.5 mL) and then the product of Example 27e (251 mg, 1.51 mmol) was added to the mixture. The system was cooled to −78° C. then evacuated with vacuum and back-filled with an atmosphere of oxygen. The mixture was warmed to room temperature and stirred vigorously for 60 hours under oxygen. The reaction was then directly loaded onto a silica gel column and purified by flash chromatography (eluent: petroleum ether/ethyl acetate=1/0→100/1) to afford the title compound as a light yellow liquid (101 mg, Yield: 37%). $^1$H NMR (400 MHz, CDCl$_3$) δ 3.28-3.20 (m, 1H), 2.93 (dd, J=17.6, 7.6 Hz, 1H), 2.21 (s, 3H), 2.11 (dd, J=17.2, 4.8 Hz, 1H), 2.06-2.03 (m, 1H), 1.98-1.87 (m, 1H), 1.82-1.76 (m, 1H), 1.70-1.64 (m, 1H), 1.59-1.50 (m, 1H), 1.39-1.31 (m, 1H), 1.23 (s, 3H), 1.03 (s, 3H) ppm; Mass spectrum (ESI+ve) m/z 205 (M+Na$^+$).

Example 27

7,7-dimethyl-5,6,7,7a-tetrahydro-1H-inden-2(4H)-one

To a stirred solution of the product of Example 27f (101 mg, 0.55 mmol) in xylenes (3 mL) was added freshly powdered potassium hydroxide (14 mg, 0.25 mmol). The reaction was stirred at 120° C. for 3 hours. The reaction solution was directly loaded onto a silica gel column and purified by silica gel flash chromatography (eluent: petroleum ether/ethyl acetate=20/1) to give a light yellow oil which was further purified by prep-HPLC to obtain a colorless oil which was further purified again by silica gel flash chromatography (eluent: petroleum ether/ethyl acetate=10/1) to afford the title compound as a colorless oil (5 mg, Yield: 5%). R$_f$=0.15 (10:1 petroleum ether/ethyl acetate); $^1$H NMR (400 MHz, CDCl$_3$) δ 5.86 (s, 1H), 2.77 (dd, J=14.0, 3.6 Hz, 1H), 2.55 (d, J=6.4 Hz, 1H), 2.32 (dd, J=19.0, 6.6 Hz, 1H), 2.25-2.15 (m, 2H), 1.85-1.81 (m, 1H), 1.68-1.62 (m, 1H), 1.54-1.44 (m, 2H), 1.02 (s, 3H), 0.69 (s, 3H) ppm; Mass spectrum (ESI+ve) m/z 165 (M+H$^+$).

Example 28

(±)-(3aR,7aS)-3a,7,7-trimethyl-3-phenyl-3a,4,5,6,7,7a-hexahydro-1H-inden-1-one

Example 28a 1-(2,6,6-trimethylcyclohex-1-enyl)ethanol

To a stirred solution of 2,6,6-trimethylcyclohex-1-enecarbaldehyde (950 mg, 6.24 mmol) in dry tetrahydrofuran (25 mL) at −78° C. under argon was added methyl magnesium iodide (3.0 M, 5.2 mL, 15.6 mmol). The resulting solution was warmed gradually to room temperature and stirred for 1 hour. Additional dry tetrahydrofuran (15 mL) was added and the reaction was stirred overnight. Saturated aqueous ammonium chloride (25 mL) was added to quench the reaction and the mixture was diluted with water (25 mL) and the organics were extracted with ethyl acetate (50 mL×3). The combined organic phase was washed with brine (50 mL×2), dried over anhydrous sodium sulfate and concentrated under reduced pressure. Purification of the residue by silica gel flash chromatography gave the title compound as a colorless liquid (856 mg, Yield: 82%). $^1$H NMR (400 MHz, CDCl$_3$) δ 4.51 (q, J=6.4 Hz, 1H), 1.98-1.91 (m, 2H), 1.86 (s, 3H), 1.56-1.52 (m, 2H), 1.44 (d, J=6.4 Hz, 3H), 1.45-1.35 (m, 3H), 1.09 (s, 3H), 0.96 (s, 3H) ppm; Mass spectrum (ESI+ve) m/z 151 (M−H$_2$O+H$^+$).

Example 28b 1-(2,6,6-trimethylcyclohex-1-enyl)ethanone

To a stirred solution of the product of Example 28a (850 mg, 5.06 mmol) in dichloromethane (25 mL) at 0° C. was added Dess-Martin periodinane (3.88 g, 9.14 mmol). The reaction was stirred at room temperature for 1.5 hours. The reaction mixture was concentrated and then the residue diluted with petroleum ether (100 mL). The mixture was filtered and the filtrate concentrated under reduced pressure. Purification of the residue by silica gel column chromatography (eluent: petroleum ether/ethyl acetate=100/1) gave a colorless liquid that was further purified by silica gel column chromatography (eluent: petroleum ether/ethyl acetate=100/1→25/1) to afford the title compound as a colorless liquid (87 mg, Yield: 10%). R$_f$=0.5 (20:1 petroleum ether/ethyl acetate); $^1$H NMR (400 MHz, CDCl$_3$+D$_2$O) δ 2.28 (s, 3H), 1.95 (t, J=6.4 Hz, 2H), 1.67-1.64 (m, 2H), 1.58 (s, 3H), 1.45-1.42 (m, 2H), 1.07 (s, 6H) ppm; Mass spectrum (ESI+ve) m/z 189 (M+Na$^+$).

Example 28c 3-hydroxy-3-phenyl-1-(2,6,6-trimethylcyclohex-1-enyl)propan-1-one

To a stirred solution of the product of Example 28b (100 mg, 0.60 mmol) in dry tetrahydrofuran (1.5 mL) at −78° C. was slowly added lithium diisopropylamide (0.36 mL, 0.72 mmol). After 15 minutes, a solution of benzaldehyde (76 mg, 0.72 mmol) in dry tetrahydrofuran (1.5 mL) was added. The mixture was stirred at −78° C. for 30 minutes. The mixture was quenched with saturated aqueous ammonium chloride and the mixture was extracted with diethyl ether (30 mL×3). The combined organic phase was washed with brine (30 mL), dried over anhydrous sodium sulfate and concentrated under reduced pressure. Purification of the residue by silica gel column chromatography (eluent: petroleum ether/ethyl acetate=100/1) to give a colorless oil which was further purified by silica gel column chromatography (eluent: petroleum ether/ethyl acetate=250/1→50/1) to afford the title compound as a pale yellow solid (90 mg, Yield: 55%). R$_f$=0.2 (20:1 petroleum ether/ethyl acetate); $^1$H NMR (400 MHz, CDCl$_3$+D$_2$O) δ 7.39-7.33 (m, 4H), 7.27-7.26 (m, 1H), 5.22 (t, J=6.0 Hz, 1H), 2.94 (d, J=6.0 Hz, 2H), 1.95 (t, J=6.4 Hz, 2H), 1.68-1.62 (m, 2H), 1.58 (s, 3H), 1.44-1.41 (m, 2H), 1.08 (s, 3H), 1.07 (s, 3H) ppm.

Example 28d (E)-3-phenyl-1-(2,6,6-trimethylcyclohex-1-enyl)prop-2-en-1-one

A solution of the product of Example 28c (29 mg, 0.11 mmol) in phosphoric acid (2 mL) and tetrahydrofuran (5 mL) was stirred at room temperature for 22 hours. The mixture was added to saturated aqueous sodium bicarbonate (30 mL). The resulting mixture was extracted with ethyl acetate (30 mL×3). The combined organic phase was washed with brine (30 mL), dried over anhydrous sodium sulfate and concentrated under reduced pressure. Purification of the residue by silica gel column chromatography (eluent: petroleum ether/ethyl acetate=100/1) afforded the title compound as a yellow oil (29 mg, Yield: 100%). R$_f$=0.6 (10:1 petroleum ether/ethyl acetate); $^1$H NMR (400 MHz, CDCl$_3$) δ 7.57-7.55 (m, 2H), 7.43-7.39 (m, 3H), 7.41 (d, J=16.0 Hz, 1H), 6.76 (d, J=16.0 Hz, 1H), 2.05 (t, J=6.4 Hz, 2H), 1.77-1.71 (m, 2H), 1.58 (s, 3H), 1.54-1.51 (m, 2H), 1.08 (s, 6H) ppm.

Example 28

(±)-(3aR,7aS)-3a,7,7-trimethyl-3-phenyl-3a,4,5,6,7, 7a-hexahydro-1H-inden-1-one

A solution of the product of Example 28d (23 mg, 0.09 mmol) in methansulfonic acid (2 ml) was stirred at 50° C. for 3 hours. The mixture was added to saturated aqueous sodium bicarbonate (30 mL). The resulting material was extracted with ethyl acetate (30 mL×3). The combined organic phase was washed with brine (30 mL), dried over anhydrous sodium sulfate and concentrated under reduced pressure. Purification by prep-TLC (eluent:
petroleum ether/ethyl acetate=30/1) afforded the title compound as a white solid (7 mg, Yield: 30%). Mp=46-48° C.; $R_f$=0.5 (10:1 petroleum ether/ethyl acetate); $^1$H NMR (400 MHz, CDCl$_3$+D$_2$O) δ 7.41 (br, m, 5H), 6.08 (s, 1H), 2.03 (s, 1H), 2.00-1.95 (m, 1H), 1.72-1.49 (m, 3H), 1.46-1.33 (m, 2H), 1.33 (s, 3H), 1.22 (s, 3H), 0.97 (s, 3H) ppm; Mass spectrum (ESI+ve) m/z 255 (M+H$^+$).

Example 29

(±)-(3aR,7aS)-3-isopropyl-3a,7,7-trimethyl-3a,4,5,6, 7,7a-hexahydro-1H-inden-1-one

Example 29a 3-hydroxy-4-methyl-1-(2,6,6-trimethylcyclohex-1-enyl)pentan-1-one A stirred solution of the product of Example 28b (86 mg, 0.52 mmol) in dry tetrahydrofuran (2 mL) at −78° C. was slowly added lithium diisopropylamide (0.39 mL, 0.78 mmol). After 15 minutes, a solution of isobutyraldehyde (75 mg, 1.04 mmol) in dry tetrahydrofuran (2 mL) was added. The mixture was stirred at −78° C. for 2 hours and then the mixture was quenched with saturated aqueous ammonium chloride. The mixture was extracted with diethyl ether (30 mL×3). The combined organic phase was washed with brine (30 mL), dried over anhydrous sodium sulfate and concentrated under reduced pressure. Purification of the residue by column chromatography (eluent: petroleum ether/ethyl acetate=100/1→25/1) gave the title compound as a colorless oil (99 mg, Yield: 80%). $R_f$=0.4 (10:1 petroleum ether/ethyl acetate); $^1$H NMR (400 MHz, CDCl$_3$) δ 3.90-3.86 (m, 1H), 3.38 (d, J=2.4 Hz, 1H), 2.74 (d, J=18.4 Hz, 1H), 2.57 (dd, J=18.4, 6.0 Hz, 1H), 1.96 (t, J=6.4 Hz, 2H), 1.74-1.63 (m, 3H), 1.59 (s, 3H), 1.46-1.40 (m, 2H), 1.08 (s, 3H), 1.07 (s, 3H), 0.95 (d, J=6.8 Hz, 3H), 0.92 (d, J=6.8 Hz, 3H) ppm.

Example 29

(±)-(3aR,7aS)-3-isopropyl-3a,7,7-trimethyl-3a,4,5,6, 7,7a-hexahydro-1H-inden-1-one A solution of the product of Example 29a (84 mg, 0.35 mmol) in phosphoric acid (3 mL) was stirred at room temperature for 3 hours. The mixture was added to saturated aqueous sodium bicarbonate and the mixture was extracted with ethyl acetate (30 mL×3). The combined organic phase was washed with brine (30 mL×2), dried over anhydrous sodium sulfate and concentrated under reduced pressure. Purification of the residue by prep-TLC (eluent: petroleum ether/ethyl acetate=20/1 afforded the title compound as a colorless oil (15 mg, Yield: 19%). $R_f$=0.5 (10:1 petroleum ether/ethyl acetate); $^1$H NMR (400 MHz, CDCl$_3$+D$_2$O) δ 5.86 (s, 1H), 2.62-2.56 (m, 1H), 1.85 (s, 1H), 1.77-1.50 (m, 4H), 1.37-1.35 (m, 2H), 1.19 (s, 6H), 1.16 (d, J=6.8 Hz, 3H), 1.15 (d, J=6.4 Hz, 3H), 0.88 (s, 3H) ppm; Mass spectrum (ESI+ve) m/z 221 (M+H$^+$).

Example 30

4,4,7a-trimethyl-5,6,7,7a-tetrahydro-1H-inden-2 (4H)-one oxime

To a solution of the product of Example 6 (71 mg, 0.4 mmol) in pyridine (3.0 mL) was added hydroxylamine hydrochloride (278 mg, 4.0 mmol) and the mixture was heated to reflux overnight. The reaction was concentrated under reduced pressure and the residue was purified by silica gel column chromatography to afford the title compound as a white solid (54 mg, Yield: 75% yield). Mp=129-130° C.; $R_f$=0.3 (5:1 petroleum ether/ethyl acetate); $^1$H NMR (400 MHz, CDCl$_3$+D$_2$O) δ 5.84 (s, 1H), 2.69 (d, J=18.0 Hz, 1H), 2.45 (d, J=18.4 Hz, 1H), 1.87-1.78 (m, 2H), 1.58-1.53 (m, 2H), 1.34-1.24 (m, 5H), 1.17 (s, 6H) ppm; Mass spectrum (ESI+ve) m/z 194 (M+H$^+$).

Example 31

4,4,7a-trimethyl-5,6,7,7a-tetrahydro-1H-inden-2 (4H)-one O-methyl oxime

To a solution of the product of Example 30 (39.8 mg, 0.21 mmol) in tetrahydrofuran (5.0 mL) at 0° C. was added sodium hydride (10 mg, 0.25 mmol) and the mixture was warmed to room temperature and stirred for 2 hours. Methyl iodide (0.064 ml, 1.03 mmol) was added drop wise and the reaction was stirred overnight. Water was added to the mixture and then the organics were extracted with ethyl acetate. The combined organic phase was washed with brine, dried over anhydrous sodium sulfate and concentrated under reduced pressure. The residue was purified by silica gel column chromatography to afford the title compound as a colorless oil (6.9 mg, Yield: 15%). $R_f$=0.3 (50:1 petroleum ether/ethyl acetate); $^1$H NMR (400 MHz, CDCl$_3$+D$_2$O) b 5.84 (s, 1H), 3.86 (s, 3H), 2.61 (d, J=18.0 Hz, 1H), 2.39 (d, J=18.0 Hz, 1H), 1.84-1.77 (m, 2H), 1.55-1.52 (m, 2H), 1.32-1.25 (m, 5H), 1.21 (s, 6H) ppm; Mass spectrum (ESI+ve) m/z 208 (M+H$^+$).

Example 32

(±)-(3R,3aS,7aS)-3,3a,7,7-tetramethyloctahydro-1H-inden-1-ol

To a solution of the product of Example 9 (80 mg, 0.41 mmol) in methanol (5 mL) was added sodium borohydride (30 mg, 0.49 mmol) and cerium trichloride heptahydrate (184 mg, 0.49 mmol). The reaction was stirred at room temperature for 2 days. The reaction mixture was concentrated under reduced pressure and then water (2 mL) was added. The mixture was then extracted with ethyl acetate (30 mL×3). The combined organic phase was washed with water (20 mL) and brine (20 mL), dried over anhydrous sodium sulfate and concentrated under reduced pressure. The residue was purified by silica gel column chromatography to afford the title compound as a white solid (20 mg, Yield:

25%). Mp=98-102° C.; R$_f$=0.4 (10:1 petroleum ether/ethyl acetate); $^1$H NMR (400 MHz, CDCl$_3$+D$_2$O) δ 4.12 (t, J=6.8 Hz, 1H), 1.88-1.41 (m, 5H), 1.25-1.13 (m, 4H), 1.06-1.00 (m, 9H), 0.91-0.84 (m, 1H), 0.77 (d, J=6.8 Hz, 3H) ppm; Mass spectrum (ESI+ve) m/z 179 (M–H$_2$O+H$^+$).

Example 33

(±)-(3aS,7aR)-4,4,7a-trimethyloctahydro-1H-inden-1-one oxime

To a solution of the product of Example 5 (50 mg, 0.28 mmol) in ethanol (5 mL) was added hydroxylamine hydrochloride (39 mg, 0.56 mmol) and pyridine (44 mg, 0.56 mmol). The mixture was heated to reflux for 2 hours. The reaction mixture was concentrated under reduced pressure and the residue diluted with ethyl acetate (50 mL). The organic phase was washed with 1N hydrochloric acid (30 mL×3) and brine (30 mL×2), dried over anhydrous sodium sulfate and concentrated under reduced pressure. The residue was purified by silica gel column chromatography to afford the title compound as a white solid (28 mg, Yield: 51%). Mp=117.6-118.6° C.; R$_f$=0.3 (30:1 petroleum ether/ethyl acetate); $^1$H NMR (400 MHz, CDCl$_3$) δ 8.38 (br, 1H), 2.64 (dd, J=19.0, 8.6 Hz, 1H), 2.38-2.29 (m, 1H), 1.83-1.80 (m, 1H), 1.66-1.43 (m, 5H), 1.38-1.17 (m, 3H), 1.27 (s, 3H), 1.04 (s, 3H), 0.84 (s, 3H); $^{13}$C NMR (100 MHz, CDCl$_3$) δ 172.8, 55.0, 44.3, 35.4, 32.4, 31.8, 29.6, 29.5, 25.4, 24.7, 23.5, 18.7 ppm; Mass spectrum (ESI+ve) m/z 196 (M+H$^+$).

Example 34

(±)-(3aR,7aS)-3-ethyl-3a,7,7-trimethyl-3a,4,5,6,7,7a-hexahydro-1H-inden-1-one

Example 34a (E)-1-(2,6,6-trimethylcyclohex-1-enyl)pent-2-en-1-one

To stirred solution of the product of 28b (140 mg, 0.84 mmol) in dry tetrahydrofuran (2 mL) at −78° C. was slowly added lithium diisopropylamide (2M, 0.56 ml, 1.12 mmol). After 15 minutes, a solution of propionaldehyde (98 mg, 1.68 mmol) in dry tetrahydrofuran (2 mL) was added. The mixture was stirred at −78° C. for 2 hours and then the mixture was stirred room temperature overnight. The reaction was quenched with saturated aqueous ammonium chloride and the mixture was extracted with ethyl acetate (50 mL×3). The combined organic phase was washed with brine (30 mL×2), dried over anhydrous sodium sulfate and concentrated under reduced pressure. Purification of the residue by silica gel column chromatography (eluent: petroleum ether/ethyl acetate=200/1) gave the title compound as a pale yellow oil (98 mg, Yield: 57%). R$_f$=0.6 (20:1 petroleum ether/ethyl acetate; $^1$H NMR (400 MHz, CDCl$_3$) δ 6.78-6.72 (m, 1H), 6.11 (d, J=16.0 Hz, 1H), 2.29-2.22 (m, 2H), 2.01-1.95 (m, 2H), 1.72-1.67 (m, 2H), 1.51 (s, 3H), 1.48-1.44 (m, 2H), 1.08 (t, J=7.2 Hz, 3H), 1.02 (s, 6H).

Example 34

(±)-(3aR,7aS)-3-ethyl-3a,7,7-trimethyl-3a,4,5,6,7,7a-hexahydro-1H-inden-1-one

A solution of the product of Example 34a (50 mg, 0.24 mmol) in phosphoric acid (2 mL) was stirred at room temperature for 4 hours. The mixture was added to saturated aqueous sodium bicarbonate (30 mL). The mixture was extracted with ethyl acetate (30 mL×3) and the combined organic phase was washed with brine (30 mL×2), dried over anhydrous sodium sulfate and concentrated under reduced pressure. The residue was purified by prep-TLC (eluent: petroleum ether/ethyl acetate=25/1) to afford the title compound as a pale yellow oil (26 mg, Yield: 53%). R$_f$=0.6 (10:1 petroleum ether/ethyl acetate; $^1$H NMR (400 MHz, CDCl$_3$) δ 5.81 (s, 1H), 2.33-2.26 (m, 2H), 1.86 (s, 1H), 1.71-1.61 (m, 2H), 1.57-1.48 (m, 2H), 1.40-1.32 (m, 2H), 1.20 (s, 3H), 1.18 (s, 3H), 1.18 (t, J=7.2 Hz, 3H), 0.89 (s, 3H) ppm; Mass spectrum (ESI+ve) m/z 207 (M+H$^+$).

Example 35

(±)-(3aS,7aS)-3a,7,7-trimethyl-3a,4,5,6,7,7a-hexahydro-1H-inden-1-one

Example 35a 1-(2,6,6-trimethylcyclohex-1-enyl)prop-2-en-1-ol

To a solution of 2,6,6-trimethylcyclohex-1-enecarbaldehyde (400 mg, 2.63 mmol) in dry tetrahydrofuran (8 mL) at room temperature under argon was added vinyl magnesium bromide (4.51 mL, 3.16 mmol). The mixture was stirred for 10 minutes and then saturated aqueous ammonium chloride was added. The heterogeneous mixture was stirred for 5 min and then extracted with diethyl ether (100 mL). The organic layer was washed with brine (50 mL×2), dried over anhydrous sodium sulfate and concentrated under reduced pressure. Purification of the residue by silica gel column chromatography gave the title compound as a colorless oil (360 mg, Yield: 76%). R$_f$=0.3 (20:1 petroleum ether/ethyl acetate; $^1$H NMR (400 MHz, CDCl$_3$) δ 6.11-6.03 (m, 1H), 5.24 (d, J=17.6 Hz, 1H), 5.11 (d, J=10.4 Hz, 1H), 4.82 (s, 1H), 1.95 (t, J=6.0 Hz, 2H), 1.75 (s, 3H), 159-1.56 (m, 3H), 1.44 (t, J=6.0 Hz, 2H), 1.12 (s, 3H), 0.98 (s, 3H).

Example 35b 1-(2,6,6-trimethylcyclohex-1-enyl)prop-2-en-1-one

To a solution of the product of Example 35a (355 mg, 1.97 mmol) in pentane (7 mL) was added manganese dioxide (2.57 g, 29.55 mmol). The reaction was stirred under argon at room temperature for 12 hours. The mixture was filtered and the filtrate concentrated to give a yellow oil that was dissolved in dichloromethane (5 mL) at 0° C. and Dess-Martin periodinane (835 mg, 1.97 mmol) was added. The resulting mixture was stirred at room temperature for 1.5 hours. Water was added and the mixture was extracted with dichloromethane (100 mL). The organic phase was washed by saturated aqueous sodium bicarbonate (50 mL×2) and brine (50 mL×2), dried over anhydrous sodium sulfate and concentrated under reduced pressure. Purification of the residue by silica gel column chromatography (eluent: petroleum ether/ethyl acetate=50/1) afforded the title compound as a light yellow oil (242 mg, Yield: 69%). R$_f$=0.5 (30:1 petroleum ether/ethyl acetate; $^1$H NMR (400 MHz, CDCl$_3$) δ 6.38 (dd, J=17.6, 10.4 Hz, 1H), 6.13 (d, J=17.6 Hz, 1H), 5.97 (d, J=10.4 Hz, 1H), 2.01 (t, J=6.4 Hz, 2H), 1.72-1.68 (m, 2H), 1.52 (s, 3H), 1.49-1.46 (t, J=6.0 Hz, 2H), 1.03 (s, 6H).

Example 35

(±)-(3aS,7aS)-3a,7,7-trimethyl-3a,4,5,6,7,7a-hexahydro-1H-inden-1-one

A mixture of the product of Example 35b (230 mg, 1.29 mmol), phosphoric acid (500 mg) and formic acid (98%, 1.5 g) was kept at 80° C. for 1 hour under argon. After cooling, the mixture was added to water (10 mL) and the resulting solution was extracted with diethyl ether (100 mL). The organic layer was washed with 10% aqueous sodium carbonate (50 mL×2), water (50 mL×2) and brine (50 mL×2), dried over anhydrous sodium sulfate and concentrated in vacuo. The residue was purified by silica gel column chromatography (eluent: petroleum ether/ethyl acetate=50/1) to afford the title compound as a light yellow syrup (128 mg, Yield: 56%). $R_f$=0.5 (30:1 petroleum ether/ethyl acetate; $^1$H NMR (400 MHz, CDCl$_3$) δ 7.37 (d, J=5.6 Hz, 1H), 5.98 (d, J=5.6 Hz, 1H), 1.80 (s, 1H), 1.67-1.65 (m, 1H), 1.60-1.57 (m, 3H), 1.37-1.35 (m, 2H), 1.20 (s, 6H), 0.95 (s, 3H) ppm; Mass spectrum (ESI+ve) m/z 179 (M+H$^+$).

Example 36

(±)-(1S,3aS,7aS)-3a,7,7-trimethyl-3a,4,5,6,7,7a-hexahydro-1H-inden-1-ol

To a solution of the product of Example 35 (111 mg, 0.62 mmol) in tetrahydrofuran (4 mL) was slowly added 9-borabicyclo[3.3.1]nonane (2.48 mL, 1.24 mmol). The reaction mixture was stirred under argon at room temperature for 25 minutes, then methanol (1.5 mL) was slowly added and stirring was continued for 1 hour. Concentration of the reaction in vacuo and purification of the residue by silica column chromatography afforded the title compound as a white solid (28 mg, Yield: 25%). Mp=55.6-57.2° C.; $R_f$=0.3 (20:1 petroleum ether/ethyl acetate; $^1$H NMR (400 MHz, CDCl$_3$) δ 5.68 (d, J=5.6 Hz, 1H), 5.56 (d, J=5.6 Hz, 1H), 4.68 (br, 1H), 1.54-1.50 (m, 2H), 1.41-1.28 (m, 5H), 1.22 (s, 3H), 1.10 (s, 3H), 1.06 (s, 3H), 0.99-0.93 (m, 1H); $^{13}$C NMR (100 MHz, CDCl$_3$) δ 143.6, 127.9, 77.4, 63.0, 43.9, 35.0, 34.3, 29.6, 29.5, 27.8, 25.5, 15.6 ppm; Mass spectrum (ESI+ve) m/z 163 (M−H$_2$O+H$^+$).

Example 37

(±)-(1R,3aS,7aS)-3a,7,7-trimethyl-3a,4,5,6,7,7a-hexahydro-1H-inden-1-ol

To a solution of the product of Example 35 (77 mg, 0.43 mmol) in tetrahydrofuran (4 mL) was slowly added 9-borabicyclo[3.3.1]nonane (2.58 mL, 1.29 mmol). The reaction mixture was stirred under argon at room temperature for 2 hours and then methanol (1.5 mL) was slowly added and stirring was continued for 1 hour. The reaction mixture was concentrated in vacuo and the residue was purified by silica gel column chromatography to afford the title compound as a colorless oil (15 mg, Yield: 20%). $R_f$=0.4 (20:1 petroleum ether/ethyl acetate; $^1$H NMR (400 MHz, CDCl$_3$) δ 5.94 (d, J=5.2 Hz, 1H), 5.83 (br, 1H), 4.62 (br, 1H), 1.73-1.53 (m, 4H), 1.30-1.18 (m, 3H), 1.22 (s, 3H), 1.18 (s, 3H), 1.07 (s, 3H), 0.86 (br, 1H); $^{13}$C NMR (100 MHz, CDCl$_3$) δ 150.9, 129.5, 79.5, 57.8, 45.3, 39.1, 37.5, 32.7, 31.2, 28.9, 26.3, 19.6 ppm; Mass spectrum (ESI+ve) m/z 163 (M−H$_2$O+H$^+$).

Example 38

(±)-(1S,2R,3aS,7aR)-2-(hydroxymethyl)-4,4,7a-trimethyloctahydro-1H-inden-1-ol

To a solution of the product of Example 8b (50 mg, 0.21 mmol) in tetrahydrofuran (5 mL) at 0° C. was added lithium aluminum hydride (16 mg, 0.42 mmol) and the mixture was stirred for 3 hours. The reaction was quenched with ethyl acetate and water. The mixture was filtered and concentrated in vacuo. Purification of the residue by silica gel column chromatography gave the title compound as a white solid (35 mg, Yield: 78%). Mp=78.9-80.2° C.; $R_f$=0.4 (2:1 petroleum ether/ethyl acetate; $^1$H NMR (400 MHz, CDCl$_3$) δ 3.94 (dd, J=10.0, 5.2 Hz, 1H), 3.78-3.76 (m, 1H), 3.70-3.66 (m, 1H), 2.69 (t, J=5.2 Hz, 1H), 2.34-2.30 (m, 1H), 2.19 (d, J=5.2 Hz, 1H), 1.67-1.50 (m, 3H), 1.40-1.29 (m, 4H), 1.19-1.15 (m, 2H), 1.16 (s, 3H), 1.04 (s, 3H), 0.81 (s, 3H); $^{13}$C NMR (100 MHz, CDCl$_3$) δ 84.6, 64.8, 52.0, 43.9, 40.4, 34.2, 31.7, 31.3, 28.7, 28.6, 26.340, 26.267, 18.7 ppm; Mass spectrum (ESI+ve) m/z 213 (M+H$^+$).

Example 39

(±)-(1S,2S,3aS,7aR)-2-(hydroxymethyl)-4,4,7a-trimethyloctahydro-1H-inden-1-ol

To a solution of the product of Example 8c (50 mg, 0.21 mmol) in tetrahydrofuran (5 mL) at 0° C. was added lithium aluminum hydride (16 mg, 0.42 mmol) and the mixture was stirred for 3 hours. The reaction was quenched with ethyl acetate and water. The mixture was filtered and concentrated in vacuo. Purification of the residue by silica gel column chromatography gave the title compound as a white solid (40.9 mg, Yield: 92%). Mp=103.6-105.4° C.; $R_f$=0.2 (2:1 petroleum ether/ethyl acetate; $^1$H NMR (400 MHz, CDCl$_3$) δ 3.76 (dd, J=9.4, 5.8 Hz, 1H), 3.63-3.58 (m, 1H), 3.41 (d, J=8.8 Hz, 1H), 2.05-1.98 (m, 3H), 1.77-1.71 (m, 1H), 1.55-1.51 (m, 2H), 1.34-1.25 (m, 3H), 1.18-1.13 (m, 3H), 1.13 (s, 3H), 1.02 (s, 3H), 0.78 (s, 3H); $^{13}$C NMR (100 MHz, CDCl3) δ 86.8, 67.4, 50.9, 43.6, 43.3, 34.0, 31.9, 30.4, 28.4, 26.5, 26.2, 24.6, 18.4 ppm; Mass spectrum (ESI+ve) m/z 213 (M+H$^+$).

Example 40

(±)-(3aS,7aS)-3a,7,7-trimethylhexahydro-1H-inden-2(3H)-one

The solution of the product of Example 6 (50 mg, 0.28 mmol) in methanol (1 mL) was added dry Pd/C (10.0 mg) and the mixture was stirred under an atmosphere of hydrogen for 24 hours. The reaction was suction filtered and the filtrate concentrated under reduced pressure to give the title compound as a yellow semisolid (46.2 mg, Yield: 92%). $R_f$=0.4 (10:1 petroleum ether/ethyl acetate; $^1$H NMR (400 MHz, CDCl$_3$) δ 2.25 (m, 2H), 2.10 (s, 2H), 1.80 (m, 1H), 1.59 (m, 1H), 1.49 (m, 1H), 1.34-1.30 (m, 7H), 1.10 (s, 3H), 0.83 (s, 3H) ppm; Mass spectrum (EI+ve) m/z 180 (M$^+$).

Example 41

4,4,7,7-tetramethyl-5,6,7,7a-tetrahydro-1H-inden-2(4H)-one

Example 41a 6-allyl-2,2,5,5-tetramethylcyclohexanone

To a solution of the product of Example 3c (500 mg, 3.24 mmol) in tetrahydrofuran (6 mL) at −78° C. under argon, was added 2.0 M lithium diisopropylamide (1.8 ml, 3.6 mmol) and then the reaction was warmed to −20° C. and stirred for 2 hours. After recooling to −78° C., hexamethylphosphoramide (0.72 ml, 3.4 mmol) and 3-bromoprop-1-ene (0.6 ml, 6.48 mmol) were added and the mixture was stirred for 3 hours. The mixture was diluted with ethyl acetate (60 mL) and the organic layer was washed with brine (50 mL), dried over anhydrous sodium sulfate and concentrated in vacuo. The residue was purified by silica gel column chromatography to afford the title compound (180 mg, Yield: 29%). $^1$H NMR (400 MHz, CDCl$_3$) δ 5.80-5.76 (m, 1H), 5.00-4.89 (m, 2H), 2.55-2.47 (m, 2H), 1.99-1.86 (m, 2H), 1.69-1.59 (m, 2H), 1.38 (m, 1H), 1.18 (s, 3H), 1.10 (s, 3H), 1.03 (s, 3H), 0.69 (s, 3H).

Example 41b 2,2,5,5-tetramethyl-6-(2-oxopropyl)cyclohexanone

A mixture of the product of Example 41a (180 mg, 0.93 mmol) palladium dichloride (10 mg, 0.05 mmol), cupric acetate hydrate (47 mg, 0.23 mmol) in dimethylacetamide (6 mL) and water (0.9 mL) under oxygen was stirred at room temperature for 3 days. The reaction mixture was concentrated in vacuo and the residue purified by silica gel column chromatography to afford the title compound as a yellow oil (50 mg, Yield: 26%). $^1$H NMR (400 MHz, CDCl3) δ 3.20 (d, J=10.8 Hz, 1H), 2.89 (dd, J=10.8, 16.8 Hz, 1H), 2.24 (s, 3H), 2.13 (dd, J=6.8, 16.8 Hz, 1H), 1.99-1.93 (m, 1H), 1.67-1.64 (m, 2H), 1.40 (d, J=13.6 Hz, 1H), 1.24 (s, 3H), 1.03 (s, 3H), 1.01 (s, 3H), 0.69 (s, 3H).

Example 41

4,4,7,7-tetramethyl-5,6,7,7a-tetrahydro-1H-inden-2 (4H)-one

To a solution of the product of Example 41b (50 mg, 0.24 mmol) in xylene (10 mL) under argon, was added potassium hydroxide (6 mg, 0.108 mmol) and the reaction was stirred at reflux for 2 hours. The mixture was concentrated under reduced pressure and the residue was purified by prep-TLC to afford the title compound as a yellow solid (30 mg, Yield: 65%). Mp=33° C.; R$_f$=0.6 (10:1 petroleum ether/ethyl acetate; $^1$H NMR (400 MHz, CDCl$_3$+D$_2$O) δ 5.87 (s, 1H), 2.76 (d, J=6.4 Hz, 1H), 2.30-2.18 (m, 2H), 1.59-1.39 (m, 4H), 1.21 (s, 3H), 1.18 (s, 3H), 1.01 (s, 3H), 0.64 (s, 3H) ppm; Mass spectrum (ESI+ve) m/z 193 (M+H$^+$).

Example 42

(±)-(3aS,7aS)-3a,7,7-trimethyl-3a,4,5,6,7,7a-hexahydro-1H-indene-2-carboxamide

Example 42a (±)-(3aS,7aS)-3a,7,7-trimethyl-3a,4,5,6,7,7a-hexahydro-1H-indene-2-carboxylic acid To a solution of the product of Example 8 (50 mg, 0.22 mmol) in methanol/water (5 mL/1 mL) was added sodium hydroxide (44 mg, 1.1 mmol). The mixture was stirred at room temperature overnight and then refluxed for 1 hour. The reaction mixture acidified to pH=2-3 with 1N hydrochloric acid, concentrated under reduced pressure and the aqueous residue extracted with ethyl acetate (60 mL). The organic layer was washed by brine (30 mL×3), dried over anhydrous sodium sulfate and concentrated under reduced pressure to afford the title compound as a white solid (44 mg, Yield: 95%). $^1$HNMR (400 MHz, CDCl$_3$) δ 6.70 (s, 1H), 2.52-2.41 (m, 2H), 1.75-1.69 (m, 1H), 1.52-1.41 (m, 3H), 1.34-1.26 (m, 5H), 1.16-1.13 (m, 1H), 1.02 (s, 3H), 0.91 (s, 3H).

Example 42

(±)-(3aS,7aS)-3a,7,7-trimethyl-3a,4,5,6,7,7a-hexahydro-1H-indene-2-carboxamide

To a solution of the product of Example 42a (41 mg, 0.20 mmol) in tetrahydrofuran (5 mL) at 0° C. was added triethylamine (30 μL, 0.22 mmol) and isobutyl chloroformate (29 μL, 0.22 mmol) and the reaction was stirred for 1 hour. Then 25% ammonium hydroxide (40.9 mg, 0.60 mmol) was added and the mixture was stirred for 35 minutes. The organics were extracted with ethyl acetate (60 mL), the organic layer was washed by 2N HCl (30 mL×2), water (30 mL×2) and brine (30 mL×2), dried over anhydrous sodium sulfate and concentrated under reduced pressure. Purification of the residue by silica column chromatography gave the title compound as a white solid (30 mg, Yield: 72%). Mp=109.9-112.6° C.; R$_f$=0.3 (1:1 petroleum ether/ethyl acetate; $^1$H NMR (400 MHz, CDCl$_3$) δ 6.33 (s, 1H), 5.46 (br, s, 2H), 2.45 (d, J=9.6 Hz, 1H), 1.73 (t, J=9.8 Hz, 1H), 1.52-1.44 (m, 3H), 1.34-1.25 (m, 5H), 1.18-1.11 (m, 1H), 0.1.03 (s, 3H), 0.91 (s, 3H) ppm; Mass spectrum (ESI+ve) m/z 208 (M+H$^+$).

Example 43

(±)-(3aR,7aS)-3-tert-butyl-3a,7,7-trimethyl-3a,4,5,6,7,7a-hexahydro-1H-inden-1-one

Example 43a 3-hydroxy-4,4-dimethyl-1-(2,6,6-trimethylcyclohex-1-enyl)pentan-1-one To a solution of the product of Example 28b (324 mg, 1.98 mmol) in dry tetrahydrofuran (13 mL) under argon at −78° C. was added drop wise lithium diisopropylamide (1.19 mL, 2.38 mmol). The mixture was stirred for 1 h, then warmed to 0° C. and stirred for 30 minutes. The reaction solution was recooled to −78° C. and pivalaldehyde (341.1 mg, 3.96 mmol) was slowly added. The reaction was stirred for 2.5 hours. The mixture was quenched by the addition of saturated aqueous ammonium chloride (20 mL) and after warming to room temperature the mixture was extracted with ethyl acetate. The organic phase was dried over anhydrous sodium sulfate and then the organic phase was concentrated under reduced pressure. The residue was purified by silica gel column chromatography (eluent: petroleum ether/ethyl acetate=80/1→40/1) to afford the title compound as a colorless oil (318 mg, Yield 63%). R$_f$=0.4 (10:1 petroleum ether/ethyl acetate; $^1$H NMR (400 MHz, CDCl$_3$) δ 3.78-3.75 (m, 1H), 3.34 (s, 1H), 2.76 (d, J=18.0 Hz, 1H), 2.50 (dd, J=18.4, 10.0 Hz, 1H), 1.95 (t, J=6.0 Hz, 2H), 1.68-1.62 (m, 2H), 1.57 (s, 3H), 1.45-1.42 (m, 2H), 1.06 (d, J=5.2 Hz, 6H), 0.91 (s, 9H).

Example 43b (E)-4,4-dimethyl-1-(2,6,6-trimethylcyclohex-1-enyl)pent-2-en-1-one To a stirred solution of the product of Example 43a (175.3 mg, 0.69 mmol) in toluene (3.5 mL) was added p-toluenesulfonic acid (6.6 mg, 0.03 mmol). The mixture was warmed and stirred at 90° C. for 30 minutes and then after cooling to room temperature aqueous 0.1N sodium hydroxide (10 mL) and water (5 mL) were added. The organics were then extracted with ethyl acetate and the organic phase was dried over anhydrous sodium sulfate. The reaction mixture was concentrated in vacuo and the residue was purified by silica gel column chromatography (eluent: petroleum ether/ethyl acetate=60/1) to afford the title compound as a colorless oil (132 mg, Yield: 82%). $R_f$=0.45 (10:1 petroleum ether/ethyl acetate; $^1$H NMR (400 MHz, CDCl$_3$) δ 6.65 (d, J=16.0 Hz, 1H), 6.11 (d, J=16.0 Hz, 1H), 2.01-1.98 (m, 2H), 1.72-1.66 (m, 2H), 1.48-1.45 (m, 5H), 1.07 (s, 9H), 1.01 (s, 6H).

Example 43

(±)-(3aR,7aS)-3-tert-butyl-3a,7,7-trimethyl-3a,4,5,6,7,7a-hexahydro-1H-inden-1-one The product of Example 43b (80 mg, 0.34 mmol) was dissolved in 85% phosphoric acid (0.5 mL) and the mixture was stirred at 90° C. for 2 hours. The reaction was cooled to room temperature and water (10 mL) was added and then the organics were extracted with ethyl acetate. The organic phase was dried over anhydrous sodium sulfate and then concentrated under reduced pressure. The residue was purified by prep-TLC to afford the title compound as a colorless oil (10 mg, Yield: 12%). $R_f$=0.4 (10:1 petroleum ether/ethyl acetate; $^1$H NMR (400 MHz, CDCl$_3$) δ 5.83 (s, 1H), 2.20-2.14 (m, 1H), 1.86 (s, 1H), 1.66-1.62 (m, 1H), 1.60-1.53 (m, 2H), 1.40-1.31 (m, 1H), 1.30 (s, 3H), 1.28 (s, 9H), 1.30-1.25 (m, 1H), 1.45 (s, 3H); 0.80 (s, 3H) ppm; Mass spectrum (ESI+ve) m/z 235 (M+H$^+$).

Example 44

(±)-(3aR,7aS)-3-cyclopropyl-3a,7,7-trimethyl-3a,4,5,6,7,7a-hexahydro-1H-inden-1-one Example 44a (E)-3-cyclopropyl-1-(2,6,6-trimethylcyclohex-1-enyl)prop-2-en-1-one To a solution of the product of Example 28b (310 mg, 1.89 mmol) in dry tetrahydrofuran (13 mL) under argon at −78° C. was drop wise added lithium diisopropylamide (1.13 mL, 2 mmol). The mixture was stirred for 1 hour, then warmed to 0° C. and stirred for 30 minutes. After recooling to −78° C., cyclopropanecarbaldehyde (264.6 mg, 3.78 mmol) was added to the reaction mixture. The reaction was stirred for 2.5 hours and then was quenched by the addition of saturated aqueous ammonium chloride (20 mL). After warming to room temperature, the reaction was extracted with ethyl acetate and the organic phase was dried over anhydrous sodium sulfate and then concentrated under reduced pressure. The residue was purified by silica gel column chromatography (eluent: petroleum ether/ethyl acetate=80/1→40/1) to afford the title compound as a white solid (232 mg, Yield: 56%). $R_f$=0.45 (10:1 petroleum ether/ethyl acetate; $^1$H NMR (400 MHz, CDCl$_3$) δ 6.18 (s, 1H), 6.17 (d, J=1.6 Hz, 1H), 1.96-1.93 (m, 2H), 1.67-1.58 (m, 3H), 1.43-1.39 (m, 5H), 0.99-0.94 (m, 8H), 0.68-0.65 (m, 2H).

Example 44

(±)-(3aR,7aS)-3-cyclopropyl-3a,7,7-trimethyl-3a,4,5,6,7,7a-hexahydro-1H-inden-1-one The product of Example 44a (100 mg, 0.46 mmol) was dissolved in 85% phosphoric acid (0.6 mL) and the mixture was stirred at 60° C. for 3 hours. The reaction was cooled to room temperature and water (10 mL) was added. The organics were extracted with ethyl acetate and the organic phase was dried over anhydrous sodium sulfate and then concentrated under reduced pressure. The residue was purified by prep-TLC to afford the get the title compound as colorless oil (42 mg, Yield: 42%). $R_f$=0.4 (10:1 petroleum ether/ethyl acetate; $^1$H NMR (400 MHz, CDCl$_3$) δ 5.38 (s, 1H), 1.86 (s, 1H), 1.81-1.76 (m, 1H), 1.71-1.45 (m, 4H), 1.38-1.34 (m, 2H), 1.27 (s, 3H), 1.19 (s, 3H), 1.11-1.03 (m, 2H), 0.88 (s, 3H), 0.73-0.69 (m, 2H) ppm; Mass spectrum (ESI+ve) m/z 219 (M+H$^+$).

Example 45

(±)-(3aR,7aS)-3-isopropyl-3a,7,7-trimethyl-3a,4,5,6,7,7a-hexahydro-1H-inden-1-one oxime To a stirred solution of the product of Example 29 (45 mg, 0.19 mmol) in pryidine (4 mL) was added hydroxylamine hydrochloride (40 mg, 0.57 mmol) and the mixture was refluxed overnight. The mixture was concentrated under reduced pressure and 1N hydrochloric acid (10 mL) and water (20 mL) was added. The mixture was extracted with ethyl acetate (30 mL×3). The combined organic phase was washed with 1N hydrochloric acid (20 mL×2) and brine (30 mL×2), dried over anhydrous sodium sulfate and concentrated under reduced pressure. Purification of the residue by silica gel column chromatography (eluent: petroleum ether/ethyl acetate=100/1→50/1) and then by prep-TLC (eluent: petroleum ether/ethyl acetate=5/1) gave title compound as a white solid (28 mg, Yield: 62%). Mp=136-138° C.; $R_f$=0.3 (10:1 petroleum ether/ethyl acetate); $^1$H NMR (400 MHz, CDCl$_3$) δ 6.39 (s, 1H), 2.48-2.41 (m, 1H), 2.12 (s, 1H), 1.97-1.92 (m, 1H), 1.54-1.50 (m, 1H), 1.41-1.21 (m, 5H), 1.15 (d, J=6.8 Hz, 6H), 1.08 (s, 3H), 1.07 (s, 3H), 0.77 (s, 3H) ppm; Mass spectrum (ESI+ve) m/z 236 (M+H$^+$).

Example 46

(±)-(3S,3aS,7aS)-3-isopropyl-3a,7,7-trimethyloctahydro-1H-inden-1-one

To a solution of the product of Example 29 (230 mg, 1.11 mmol) in methanol (3 mL) was added 5% Pd/C (36 mg). The mixture was stirred at room temperature under an atmosphere of hydrogen overnight. The mixture was filtered and the filtrate concentrated under reduced pressure. Purification of the residue by silica gel column chromatography (eluent: petroleum ether/ethyl acetate=100/1) gave the title compound as a white solid (208 mg, Yield: 84%). Mp=36-38° C.; $R_f$=0.8 (10:1 petroleum ether/ethyl acetate); $^1$H NMR (400 MHz, CDCl$_3$) δ 2.32-2.24 (m, 1H), 2.02 (dd, J=18.8, 12.4 Hz, 1H), 1.87-1.82 (m, 1H), 1.65 (s, 1H), 1.65-1.42 (m, 4H), 1.33 (s, 3H), 1.25 (s, 3H), 1.25-1.11 (m, 3H), 1.06 (s, 3H), 1.02 (d, J=6.8 Hz, 3H), 0.87 (d, J=6.8 Hz, 3H); $^{13}$C NMR (100 MHz, CDCl$_3$) δ 218.2, 66.2, 50.9, 43.6, 40.4, 36.1, 33.1, 30.2, 29.6, 28.2, 27.1, 27.0, 24.8, 21.4, 18.2 ppm; Mass spectrum (ESI+ve) m/z 223 (M+H$^+$).

Example 47

(±)-(1S,3aR,7aS)-3-isopropyl-3a,7,7-trimethyl-3a,4,
5,6,7,7a-hexahydro-1H-inden-1-ol A stirred solution of the product of Example 29 (77 mg, 0.35 mmol) in dry tetrahydrofuran (4 mL) cooled to −78° C. was added lithium aluminum hydride (80 mg, 2.10 mmol). The reaction was stirred at −78° C. for 2 hours. Water (0.2 mL), 15% aqueous sodium hydroxide (0.2 mL) and water (0.6 mL) was added to quench the reaction. Water (20 mL) was added and the reaction and the mixture was extracted with ethyl acetate (30 mL×3). The combined organic phase was washed with brine (30 mL×2), dried over anhydrous sodium sulfate and then concentrated under reduced pressure. Purification of the residue by silica gel column chromatography (eluent: petroleum ether/ethyl acetate=250/1) gave a white solid (62 mg) that was further purified by prep-HPLC to afford the title compound as a white solid (30 mg, Yield: 38%). Mp=95-96° C.; $R_f$=0.5 (10:1 petroleum ether/ethyl acetate); $^1$H NMR (400 MHz, CDCl$_3$) δ 5.32 (s, 1H), 4.58 (t, J=7.2 Hz, 1H), 2.26-2.22 (m, 1H), 1.65-1.61 (m, 1H), 1.53-1.46 (m, 1H), 1.39-1.23 (m, 5H), 1.21 (s, 3H), 1.09-1.03 (m, 12H), 0.94 (dt, J=13.2, 4.0 Hz, 1H) ppm; Mass spectrum (ESI+ve) m/z 205 (M−H$_2$O+H$^+$).

Example 48

(±)-(3S,3aS,7aS)-3-isopropyl-3a,7,7-trimethyloctahydro-1H-inden-1-one O-methyl oxime A solution of the product of Example 46 (22 mg, 0.10 mmol) in pyridine (2 ml) was added O-methylhydroxylamine (50 mg, 0.60 mmol). The reaction was stirred at 150° C. under microwave irradiation for 1 hour. The mixture was concentrated under reduced pressure, water (20 mL) was added and the mixture was extracted with ethyl acetate (30 mL×3). The combined organic phase was washed with 1N hydrochloric acid (20 mL×2) and brine (30 mL×2), dried over anhydrous sodium sulfate and concentrated under reduced pressure. The residue was purified by silica gel column chromatography (eluent: petroleum ether) to afford the title compound as a colorless oil (6.6 mg, Yield: 26%). $R_f$=0.5 (100:1 petroleum ether/ethyl acetate); $^1$H NMR (400 MHz, CDCl$_3$) δ 3.84 (s, 3H), 2.64 (dd, J=18.0, 8.0 Hz, 1H), 2.12-2.04 (m, 1H), 2.02 (s, 1H), 1.75-1.72 (m, 1H), 1.60-1.52 (m, 2H), 1.44-1.38 (m, 1H), 1.32-1.16 (m, 10H), 1.09 (s, 3H), 0.97 (d, J=6.8 Hz, 3H), 0.87 (d, J=6.8 Hz, 3H); $^{13}$C NMR (100 MHz, CDCl$_3$) δ 165.8, 61.4, 60.3, 53.3, 44.3, 34.5, 33.6, 30.9, 30.3, 29.3, 27.2, 27.0, 26.9, 24.6, 21.4, 18.0 ppm; Mass spectrum (ESI+ve) m/z 252 (M+H$^+$).

Example 49

(±)-(3aS,7aS)-3a,7,7-trimethyloctahydro-1H-indene-2-carboxamide

To a solution of the product of Example 42 (18.5 mg, 0.09 mmol) in methanol (4 mL) was added 5% Pd/C (20 mg) and then the mixture was stirred at room temperature under an atmosphere of hydrogen overnight. The mixture was filtered and the filtrate was concentrated under reduced pressure. Purification of the residue by silica gel column chromatography afforded the title compound as a white solid (15.5 mg, Yield: 82%). Mp=97.7-99.6° C.; $R_f$=0.35 (1:1 petroleum ether/ethyl acetate); $^1$H NMR (400 MHz, CDCl$_3$) δ 5.31 (bs, 2H), 2.68-2.63 (m, 1H), 2.04-1.91 (m, 2H), 1.77 (d, J=8.8 Hz, 2H), 1.52-1.37 (m, 5H), 1.21-1.12 (m, 2H), 1.12 (s, 3H), 1.03 (s, 3H), 0.85 (s, 3H); $^{13}$C NMR (100 MHz, CDCl$_3$) δ 178.7, 55.7, 46.2, 40.8, 40.4, 34.2, 34.1, 33.0, 31.8, 31.6, 28.8, 27.9, 19.2 ppm; Mass spectrum (ESI+ve) m/z 210 (M+H$^+$).

Example 50

(±)-(1R,3S,3aS,7aS)-3-isopropyl-3a,7,7-trimethyloctahydro-1H-inden-1-ol

To a stirred solution of the product of Example 46 (60 mg, 0.27 mmol) in dry tetrahydrofuran (4 mL) cooled to −78° C. was added lithium aluminum hydride (62 mg, 1.62 mmol). The reaction was stirred at −78° C. for 3 hours and then allowed to warm to room temperature and stirred for an additional 1.5 hours. Water (0.2 mL), 15% aqueous sodium hydroxide (0.2 mL) and water (0.6 mL) was added to quench the reaction. Additional water (20 mL) was added to the reaction mixture and then the organics were extracted with ethyl acetate (30 mL×3). The combined organic phase was washed with brine (30 mL×2), dried over anhydrous sodium sulfate and then concentrated under reduced pressure. Purification of the residue by silica gel column chromatography (eluent: petroleum ether/ethyl acetate=100/1) gave the title compound as a colorless liquid (45 mg, Yield: 74%). $R_f$=0.8 (10:1 petroleum ether/ethyl acetate); $^1$H NMR (400 MHz, CDCl$_3$) δ 4.31-4.29 (m, 1H), 2.29-2.23 (m, 1H), 1.80-1.54 (m, 5H), 1.38-1.25 (m, 3H), 1.19-1.07 (m, 3H), 1.14 (s, 3H), 1.13 (s, 3H), 1.07 (s, 3H), 0.97 (d, J=6.4 Hz, 3H), 0.88 (d, J=6.4 Hz, 3H); $^{13}$C NMR (100 MHz, CDCl$_3$) δ 75.1, 61.2, 56.1, 43.6, 38.5, 36.7, 32.7, 31.0, 30.9, 28.7, 28.6, 27.8, 24.4, 21.8, 19.1 ppm; Mass spectrum (EI+ve) m/z 224 (M$^+$).

Example 51

(±)-(3aR,7aS)-3-isopropyl-3a,7,7-trimethyl-3a,4,5,6,7,7a-hexahydro-1H-inden-1-one O-methyl oxime A solution of the product of Example 29 (70 mg, 0.32 mmol) in pyridine (2 mL) was added O-methylhydroxylamine hydrochloride (160 mg, 1.91 mmol). The reaction was stirred at 150° C. under microwave irradiation for 1 hour. The mixture was concentrated under reduced pressure and water (20 mL) was added. The reaction mixture was extracted with ethyl acetate (30 mL×3) and the combined organic phase was washed with 1N hydrochloric acid (20 mL×2) and brine (30 mL×2), dried over anhydrous sodium sulfate and then concentrated under reduced pressure. Purification of the residue by silica gel column chromatography (eluent: petroleum ether/ethyl acetate=100/1) afforded a 35 mg of a colorless liquid which was further purified by prep-TLC (eluent: petroleum ether/ethyl acetate=100/1) to afford the title compound as a pale yellow liquid (23 mg, Yield: 29%). $R_f$=0.9 (100:1 petroleum ether/ethyl acetate); $^1$H NMR (400 MHz, CDCl$_3$) (major isomer) δ 6.27 (s, 1H), 3.88 (s, 3H), 2.45-2.41 (m, 0.1H), 2.11 (s, 1H), 1.98-1.94 (m, 1H), 1.52-1.21 (m, 5H), 1.15-1.07 (m, 12H), 0.71 (s, 3H) ppm; Mass spectrum (ESI+ve) m/z 250 (M+H$^+$).

Example 52

(±)-(3S,3aS,7aS)-3-isopropyl-3a,7,7-trimethyloctahydro-1H-inden-1-one oxime

To a solution of the product of Example 46 (39 mg, 0.18 mmol) in pyridine (2 mL) was added hydroxylamine hydrochloride (38 mg, 0.54 mmol). The reaction was stirred at 150° C. under microwave irradiation for 1 hour. The mixture was concentrated under reduced pressure and water (20 mL) was added. The mixture was extracted with ethyl acetate (30 mL×3) and the combined organic phase was washed with 1N hydrochloric acid (20 mL×2) and brine (20 mL×2), dried over anhydrous sodium sulfate and concentrated under reduced pressure. Purification of the residue by silica gel column chromatography (eluent: petroleum ether/ethyl acetate 100:1→20/1) to afford 18 mg of material was purified by crystallization from cold petroleum ether to afford the title compound as a white solid (7 mg, Yield: 16%). Mp=152-153° C.; $R_f$=0.6 (10:1 petroleum ether/ethyl acetate); $^1$H NMR (400 MHz, CDCl$_3$+D$_2$O) δ 2.74 (dd, J=18.0, 8.0 Hz, 1H), 2.15 (dd, J=18.0, 12.4 Hz, 1H), 2.04 (s, 1H), 1.79-1.74 (m, 1H), 1.60-1.51 (m, 3H), 1.37-1.14 (m, 4H), 1.24 (s, 3H), 1.18 (s, 3H), 1.09 (s, 3H), 0.99 (d, J=6.8 Hz, 3H), 0.88 (d, J=6.8 Hz, 3H); $^{13}$C NMR (100 MHz, CDCl$_3$) δ 167.5, 60.3, 53.2, 44.5, 34.7, 33.6, 30.9, 30.4, 28.8, 27.2, 27.1, 27.0, 24.6, 21.4, 18.0 ppm; Mass spectrum (ESI+ve) m/z 238 (M+H$^+$).

Example 53

4,4-dimethyl-5,6,7,7a-tetrahydro-1H-inden-2(4H)-one

To a solution of the product of Example 27f (116 mg, 0.64 mmol) in tetrahydrofuran (5 mL) at 0° C. was added potassium t-butoxide (71.8 mg, 0.64 mmol) and the mixture was stirred for 30 minutes. The reaction was quenched with saturated aqueous ammonium chloride (3 mL) and the mixture was extracted with ethyl acetate (100 mL). The organic phase was washed with water (50 mL×2) and brine (50 mL×2), dried over anhydrous sodium sulfate and concentrated under reduced pressure. Purification of the residue by prep-TLC gave the title compound as light yellow oil (8 mg, Yield: 8%). $R_f$=0.3 (10:1 petroleum ether/ethyl acetate); $^1$H NMR (400 MHz, CDCl$_3$) δ 5.85 (s, 1H), 2.91-2.88 (m, 1H), 2.59 (dd, J=18.8, 6.8 Hz, 1H), 2.19-2.15 (m, 1H), 1.99 (dd, J=18.8, 2.0 Hz, 1H), 1.75-1.63 (m, 3H), 1.41-1.36 (m, 1H), 1.24 (s, 3H), 1.21 (s, 3H), 1.12-1.05 (m, 1H) ppm; Mass spectrum (ESI+ve) m/z 165 (M+H$^+$).

Example 54

4,4-dimethylhexahydro-1H-inden-2(3H)-one

To a solution of a mixture of the product of Example 53 and the product of Example 27 (56 mg, 0.34 mmol) in methanol (5 mL) was added Pd/C (50 mg). The reaction mixture was stirred at room temperature overnight under an atmosphere of hydrogen. The reaction was filtered and the filtrate was concentrated in vacuo. The residue was purified by silica gel column chromatography (eluent: petroleum ether/ethyl acetate=100/1) to afford the title compound as a light yellow oil (27 mg, Yield: 48%). $R_f$=0.6 (10:1 petroleum ether/ethyl acetate); $^1$H NMR (400 MHz, CDCl$_3$): δ 2.39-2.27 (m, 2H), 2.14-1.99 (m, 4H), 1.58-1.47 (m, 3H), 1.32-1.21 (m, 2H), 1.05 (s, 3H), 0.98-0.89 (m, 1H), 0.87 (s, 3H); $^{13}$C NMR (100 MHz, CDCl$_3$): 220.02, 47.70, 46.68, 37.63, 33.28, 32.95, 31.32, 30.10, 27.71, 26.94, 20.99 ppm; Mass spectrum (ESI+ve) m/z 167 (M+H$^+$).

Example 55

4,4-dimethylhexahydro-1H-inden-2(3H)-one oxime

To a solution of the product of Example 54 (45 mg, 0.27 mmol) in ethanol (5 mL) was added hydroxylamine hydrochloride (37.5 mg, 0.54 mmol) and pyridine (42.7 mg, 0.54 mmol). The mixture was heated to reflux for 2 hours. The mixture was concentrated under reduced pressure and water (20 ml) was added to the residue. The organics were extracted with ethyl acetate (50 mL) and the organic layer was washed with 1N hydrochloric acid (30 mL×2) and brine (30 mL×2), dried over anhydrous sodium sulfate and concentrated under reduced pressure. Purification of the residue by silica gel column chromatography gave the title compound as a white solid (38 mg, Yield: 78%). Mp=67.4-69.6° C.; $R_f$=0.3 (5:1 petroleum ether/ethyl acetate); $^1$H NMR (400 MHz, CDCl$_3$) δ 2.54-2.39 (m, 2H), 2.35-2.14 (m, 3H), 1.79-1.76 (m, 1H), 1.48-1.45 (m, 3H), 1.34-1.26 (m, 2H), 1.20-1.17 (m, 1H), 1.01 (s, 3H), 0.96-0.85 (m, 4H); $^{13}$C NMR (100 MHz, CDCl$_3$) δ 166.6, 166.4, 48.2, 48.0, 38.4, 35.2, 34.8, 34.3, 33.3, 33.1, 31.4, 31.3, 30.0, 29.9, 29.8, 27.9, 27.6, 26.9, 26.8, 21.3, 21.1 ppm; Mass spectrum (ESI+ve) m/z 182 (M+H$^+$).

Example 56

4,4-dimethyl-2,3,4,5,6,7-hexahydro-1H-inden-1-one

Example 56a 3,3-dimethylcyclohex-1-enecarbaldehyde

To a stirred solution of a mixture of the product of Example 27c (2.10 g, 10.0 mmol) in dry diethyl ether (50 mL) at −20° C. was added lithium aluminum hydride (0.57 g, 15.0 mmol) portion wise. The resulting mixture was stirred for 1 hour during which time the reaction temperature was allowed to warm to room temperature. The reaction was diluted with ethyl acetate (5 mL) and then saturated aqueous ammonium chloride (5 mL) was added and the mixture was further diluted with diethyl ether (300 mL). The organic phase was dried over anhydrous magnesium sulfate, filtered and then concentrated under reduced pressure to give a colorless liquid. The material was dissolved in acetone (20 mL) and 2N HCl (0.05 mL) was added and the solution was shaken for 1 minute. Solid sodium bicarbonate (50 mg) was added and the solution was concentrated under reduced pressure. The residue was purified by silica gel column chromatography give the title compound as a colorless liquid (1.15 g, Yield: 83%). $^1$H NMR (400 MHz, CDCl$_3$) δ 9.39 (s, 1H), 6.47 (s, 1H), 2.14 (t, J=6.0 Hz, 2H), 1.69-1.63 (m, 2H), 1.53-1.50 (m, 2H), 1.10 (s, 6H).

Example 56b 1-(3,3-dimethylcyclohex-1-enyl)prop-2-en-1-ol

To a stirred solution of the product of Example 56a (200 mg, 1.45 mmol) in tetrahydrofuran (5 mL) at 0° C. was added vinylmagnesium bromide (3.1 ml, 2.17 mmol) and then the mixture was warmed to room temperature and stirred for 1 h. The reaction was quenched with saturated aqueous ammonium chloride (10 mL) and the organic were then extracted with ethyl acetate (10 mL×3). The combined organic phase was washed brine, dried over anhydrous sodium sulfate and concentrated under reduced pressure to afford the title compound as a colorless oil (256 mg, Yield, 100%). $^1$H NMR (400 MHz, CDCl$_3$) δ 5.90-5.81 (m, 1H), 5.45 (s, 1H), 5.26 (dt, J=17.2, 1.2 Hz, 1H), 5.14 (dt, J=14.4, 1.2 Hz, 1H), 4.45 (d, J=6.0 Hz, 1H), 1.95-1.88 (m, 2H), 1.66-1.58 (m, 3H), 1.43-1.39 (m, 2H), 0.98 (s, 3H), 0.97 (s, 3H).

Example 56c 1-(3,3-dimethylcyclohex-1-enyl)prop-2-en-1-one

To a solution of compound of the product of Example 56b (246 mg, 1.47 mmol) in dichloromethane (5 mL) at 0° C. was portion wise added Dess-Martin periodinane (1.13 g, 2.66 mmol) and then the mixture was warmed to room temperature and stirred for 1 hour. Then dichlormethane (20 mL) was added and the mixture was washed with saturated aqueous sodium bicarbonate and brine, dried over anhydrous sodium sulfate and concentrated under reduced pressure. The residue was purified by prep-TLC to afford the title compound as a colorless oil (61 mg, Yield: 25%). $^1$H NMR (400 MHz, CDCl$_3$) δ 6.94 (dd, J=17.2, 10.8 Hz, 1H), 6.59 (s, 1H), 6.24 (dd, J=17.2, 1.8 Hz, 1H), 5.70 (dd, J=10.4, 2.0 Hz, 1H), 2.26-2.23 (m, 2H), 1.68-1.65 (m, 2H), 1.48-1.45 (m, 2H), 1.08 (s, 6H).

Example 56

4,4-dimethyl-2,3,4,5,6,7-hexahydro-1H-inden-1-one

A mixture of the product of Example 56c (40.0 mg, 0.244 mmol) in phosphoric acid (86 mg) and formic acid (0.26 g) was stirred at 80° C. for 2 hours. Dichloromethane (10 mL) was added and the mixture was washed with saturated aqueous sodium bicarbonate (5 mL×2) and brine (10 mL), dried over anhydrous sodium sulfate and concentrated under reduced pressure. The residue was purified by prep-TLC to afford the title compound as a yellow oil (14 mg, Yield: 35%). R$_f$=0.4 (10:1 petroleum ether/ethyl acetate); $^1$H NMR (400 MHz, CDCl$_3$) δ 2.52-2.50 (m, 2H), 2.38-2.35 (m, 2H), 2.11-2.08 (m, 2H), 1.69-1.64 (m, 2H), 1.56-1.53 (m, 2H), 1.14 (s, 6H); $^{13}$C NMR (100 MHz, CDCl$_3$) δ 209.8, 179.8, 137.3, 38.3, 34.5, 27.3, 25.0, 20.6, 18.7 ppm; Mass spectrum (ESI+ve) m/z 165 (M+H$^+$).

Example 57

(±)-(3aS,7aS)-2-(methoxymethyl)-3a,7,7-trimethyl-octahydro-1H-indene

To a stirred solution of the product of Example 26 (43 mg, 0.22 mmol) in dichloromethane (6 mL) at 0° C. was added 1,8-bis(dimethylamino)naphthalene (471.5 mg, 2.2 mmol) and trimethyloxonium tetrafluoroborate (325 mg, 2.2 mmol). The mixture was warmed to room temperature stirred overnight. The reaction was quenched with saturated aqueous sodium bicarbonate (15 mL) and the resulting mixture was extracted with dichloromethane (50 mL). The organic layer was washed 5% hydrochloric acid (30 mL×3) and brine (30 mL×2), dried over anhydrous sodium sulfate and concentrated in vacuo. Purification of the residue by silica gel column chromatography afforded the title compound as a colorless oil (10 mg, Yield: 22%). R$_f$=0.6 (50:1 petroleum ether/ethyl acetate); $^1$H NMR (400 MHz, CDCl$_3$) δ 3.27 (s, 3H), 3.21 (d, J=7.2 Hz, 2H), 2.15-2.08 (m, 1H), 1.75-1.73 (m, 1H), 1.60 (t, J=12.2 Hz, 1H), 1.51-1.45 (m, 1H), 1.31-1.19 (m, 6H), 1.14-1.10 (m, 2H), 1.03 (s, 3H), 0.95 (s, 3H), 0.77 (s, 3H); $^{13}$C NMR (100 MHz, CDCl$_3$) δ 78.2, 57.7, 54.6, 45.5, 39.1, 34.7, 34.3, 33.7, 32.4, 30.94, 30.86, 28.1, 27.5, 18.6 ppm; Mass spectrum (ESI+ve) m/z 209 (M+H$^+$).

Example 58

(±)-(1S,3S,3aS,7aS)-3-isopropyl-3a,7,7-trimethyl-octahydro-1H-inden-1-ol

A mixture of the product of Example 47 (30.0 mg, 0.135 mmol) and 10% Pd/C (50 mg) in methanol (7 mL) was stirred at room temperature under a hydrogen atmosphere overnight. The mixture was filtered and concentrated under reduced pressure. The residue was purified by silica gel column chromatography (eluent: petroleum ether/ethyl acetate=50/1) to afford the title compound as a colorless oil (20 mg, Yield: 66%). R$_f$=0.5 (10:1 petroleum ether/ethyl acetate); $^1$H NMR (400 MHz, CDCl$_3$) δ 4.13-4.11 (m, 1H), 1.93-1.85 (m, 1H), 1.66-1.61 (m, 3H), 1.59-1.48 (m, 1H), 1.45-1.40 (m, 2H), 1.25-1.20 (m, 5H), 1.17 (s, 3H), 1.08 (s, 3H), 1.00 (s, 3H), 0.96 (d, J=6.4 Hz, 3H), 0.83 (d, J=6.4 Hz, 3H); $^{13}$C NMR (100 MHz, CDCl$_3$) δ 73.0, 66.7, 55.5, 44.9, 36.2, 35.9, 31.8, 31.6, 29.2, 28.9, 27.2, 26.6, 24.5, 21.4, 18.6 ppm; Mass spectrum (ESI+ve) m/z 224 (M+H$^+$).

Example 59

(±)-(3aS,7aS)-3a,7,7-trimethyloctahydro-1H-inden-1-one

To a solution of the product of Example 35 (50 mg, 0.28 mmol) in methanol (5 mL) was added Pd/C (30 mg). The solution was stirred at room temperature under an atmosphere of hydrogen overnight. The mixture was filtered and concentrated under reduced pressure. Purification of the residue by silica gel column chromatography (eluent: petroleum ether/dichloromethane=2/1) afforded the title compound as a colorless semisolid (32 mg, Yield: 63%). R$_f$=0.5 (2:1 petroleum ether/dichloromethane); $^1$H NMR (400 MHz, CDCl$_3$) δ 2.34-2.27 (m, 1H), 2.23-2.16 (m, 1H), 2.05-1.97 (m, 1H), 1.61-1.43 (m, 5H), 1.40-1.31 (m, 2H), 1.19-1.12 (m, 1H), 1.06 (s, 3H), 0.97 (s, 3H), 0.93 (s, 3H); $^{13}$C NMR (100 MHz, CDCl$_3$) δ 222.2, 64.0, 39.8, 38.9, 36.9, 35.5, 32.5, 32.3, 32.1, 31.5, 23.9, 18.2 ppm; Mass spectrum (ESI+ve) m/z 181 (M+H$^+$).

Example 60

(±)-(1S,3aS,7aS)-3a,7,7-trimethyloctahydro-1H-inden-1-ol

To a solution of the product of Example 59 (36 mg, 0.20 mmol) in methanol (5 mL) was added Pd/C (20 mg). The solution was stirred under an atmosphere of hydrogen at room temperature overnight. The mixture was filtered and the filtrate was concentrated under reduced pressure. The residue was purified by silica gel column chromatography (eluent: petroleum ether/ethyl acetate=20/1) to afford the title compound as a white solid (24 mg, Yield: 67%). Mp=59.2-61.3° C.; R$_f$=0.2 (20:1 petroleum ether/ethyl acetate); $^1$H NMR (400 MHz, CDCl$_3$) δ 4.24 (t, J=6.6 Hz, 1H), 2.16-2.10 (m, 1H), 1.76-1.67 (m, 1H), 1.61-1.31 (m, 5H), 1.25-1.15 (m, 5H), 1.13 (s, 3H), 1.05 (s, 3H), 1.01 (s, 3H); $^{13}$C NMR (100 MHz, CDCl$_3$) δ 76.2, 64.3, 42.0, 41.0, 35.8, 33.2, 32.0, 31.6, 31.0, 29.0, 28.1, 18.9 ppm; Mass spectrum (ESI+ve) m/z 165 (M−H$_2$O+H$^+$).

Example 61

(±)-(1R,7aS)-1-isopropyl-4,4-dimethyl-5,6,7,7a-tetrahydro-1H-inden-2(4H)-one

To a solution of lithium diisopropyl amide (0.35 mL, 0.70 mmol) in dry tetrahydrofuran (1 mL) at 0° C. under argon was added the solution of the product of Example 53 (57 mg, 0.35 mmol) in dry tetrahydrofuran (2 mL). Then the solution was stirred at room temperature for 30 minutes after which it was cooled to −78° C. and isopropyl iodide (0.35 mL, 3.50 mmol) was added. The solution mixture was warmed to room temperature and stirred overnight. The reaction was quenched with water and the organics were extracted with ethyl acetate (50 mL). The combined organic phase was washed with brine (30 mL×2), dried over anhydrous sodium sulfate and concentrated under reduced pressure. Purification of the residue by silica gel column chromatography (eluent: petroleum ether/ethyl acetate=50/1→20/1) afforded the title compound as a light yellow oil (19 mg, Yield: 26%). $R_f$=0.5 (20:1 petroleum ether/ethyl acetate); $^1$H NMR (400 MHz, CDCl$_3$) δ 5.80 (s, 1H), 2.63-2.58 (m, 1H), 2.26-2.21 (m, 1H), 2.14-2.10 (m, 1H), 1.91-1.89 (m, 1H), 1.75-1.64 (m, 3H), 1.40-1.31 (m, 1H), 1.21 (s, 3H), 1.19 (s, 3H), 1.15-1.08 (m, 1H), 1.00 (d, J=6.8 Hz, 1H), 0.77 (d, J=6.8 Hz, 1H) ppm; Mass spectrum (ESI+ve) m/z 207 (M+H$^+$).

Example 62

(±)-(3aS,7aS)-3a,7,7-trimethylhexahydro-1H-inden-2(3H)-one oxime

To a solution of the product of Example 40 (50 mg, 0.28 mmol) in ethanol (5 mL) was added hydroxylamine hydrochloride (39 mg, 0.56 mmol) and pyridine (44 mg, 0.56 mmol). The mixture was heated to reflux for 2 hours. The reaction mixture was concentrated under reduced pressure and the residue was portioned between water and ethyl acetate (50 mL). The organic phase was washed with 1N hydrochloric acid (30 mL×2) and brine (30 mL×2), dried over anhydrous sodium sulfate and concentrated under reduced pressure. Purification of the residue by silica gel column chromatography gave the title compound as a white solid (34 mg, Yield: 62%). Mp=124.7-126.1° C.; $R_f$=0.3 (5:1 petroleum ether/ethyl acetate); $^1$H NMR (400 MHz, CDCl$_3$) (Major isomer) δ 8.32 (br, 1H), 2.60-2.17 (m, 4H), 1.59-1.53 (m, 2H), 1.46-1.40 (m, 1H), 1.37-1.30 (m, 1H), 1.28-1.20 (m, 3H), 1.18 (s, 3H), 1.05 (s, 3H), 0.87 (s, 3H); $^{13}$C NMR (100 MHz, CDCl$_3$) (Isomers) δ 165.0, 164.9, 53.0, 52.6, 47.6, 44.3, 39.7, 39.3, 34.2, 33.8, 33.5, 32.9, 32.4, 32.1, 32.0, 30.6, 30.5, 30.0, 28.9, 28.7, 27.6, 27.1, 18.9, 18.7 ppm; Mass spectrum (ESI+ve) m/z 196 (M+H$^+$).

Example 63

(±)-(3aS,7aS)-3a,7,7-trimethyloctahydro-1H-inden-2-ol

To a 0° C. stirred solution of the product of Example 40 (100 mg, 0.55 mmol) in methanol (1 mL) and tetrahydrofuran (7 mL) was added sodium borohydride (25 mg, 0.66 mmol) and the reaction was warmed to room temperature and stirred for 2 hours. The reaction was quenched with 5% hydrochloric acid (3 mL) and then the organics were extracted with ethyl acetate (50 mL). The organic layer was washed with brine (30 mL×2), dried over anhydrous sodium sulfate and concentrated under reduced pressure.

Purification of the residue by silica gel column chromatography (eluent: petroleum ether/ethyl acetate=10/1) afforded the title compound as a colorless oil (95 mg, Yield: 94%). $R_f$=0.3 (10:1 petroleum ether/ethyl acetate); $^1$H NMR (400 MHz, CDCl$_3$) (Major isomer) δ 4.30-4.24 (m, 1H), 2.20-2.13 (m, 1H), 1.83 (dd, J=14.2, 5.0 Hz, 2H), 1.72-1.40 (m, 6H), 1.36-1.15 (m, 3H), 1.08 (s, 3H), 1.02 (s, 3H), 0.83 (s, 3H); $^{13}$C NMR (100 MHz, CDCl$_3$) (Major isomer) δ 70.7, 54.6, 53.3, 40.0, 39.4, 34.4, 34.2, 32.0, 31.6, 29.0, 28.0, 19.4; (Minor isomer) δ 70.3, 54.2, 52.6, 41.1, 39.1, 34.3, 34.2, 31.7, 31.4, 28.9, 28.0, 19.2 ppm; Mass spectrum (ESI+ve) m/z 165 (M−H$_2$O+H$^+$).

Example 64

(±)-(3aS,7aS)-2,3,4,4-tetramethyl-3a,4,5,6,7,7a-hexahydro-1H-inden-1-one

Example 64a 1-(3,3-dimethylcyclohex-1-enyl)-2-methylbut-2-en-1-ol

To a solution of the product of Example 56a (300 mg, 2.17 mmol) in tetrahydrofuran (8 mL) at 0° C. was added 1-methyl-1-propenylmagnesium bromide (0.5 M in tetrahydrofuran, 6.7 mL, 3.26 mmol) and the reaction was then warmed to room temperature and stirred for 1.5 hours. The mixture was quenched with saturated aqueous ammonium chloride and the organics were extracted with ethyl acetate. The organic layer was washed with brine, dried over anhydrous sodium sulfate and concentrated under reduced pressure. The residue was purified by silica gel column chromatography to give the title compound as a colorless oil (252 mg, Yield: 60%). $R_f$=0.6 (10:1 petroleum ether/ethyl acetate); $^1$H NMR (400 MHz, CDCl$_3$) (Major isomer) δ 5.50 (s, 1H), 5.42 (q, 1H J=6.8 Hz, 1H), 4.92 (d, J=3.2 Hz, 1H), 1.76-1.47 (m, 11H), 1.42-1.39 (m, 2H), 0.99 (s, 3H), 0.98 (s, 3H) ppm.

Example 64b 1-(3,3-dimethylcyclohex-1-enyl)-2-methylbut-2-en-1-one

To a solution of the product of Example 64a (230 mg, 1.18 mmol) in dichloromethane (4 mL) at 0° C. was added Dess-Martin periodinane (1.35 g, 3.19 mmol) and the reaction mixture was warmed to room temperature and stirred for 1 hour. The mixture was diluted with petroleum ether and filtered. The filtrate was concentrated under reduced pressure and the residue purified by silica gel column chromatography to afford the title compound as a colorless oil (207 mg, Yield: 91%). $R_f$=0.5 (20:1 petroleum ether/ethyl acetate); $^1$H NMR (400 MHz, CDCl$_3$) (Major isomer) δ 6.52 (s, 1H), 5.61-5.55 (m, 1H), 2.21 (dt, J$_1$=6.0 Hz, J$_2$=1.6 Hz, 2H), 1.85-1.84 (m, 3H), 1.70-1.64 (m, 2H), 1.52-1.45 (m, 5H), 1.05 (s, 6H) ppm; Mass spectrum (ESI+ve) m/z 193 (M+H$^+$).

Example 64

(±)-(3aS,7aS)-2,3,4,4-tetramethyl-3a,4,5,6,7,7a-hexahydro-1H-inden-1-one

To the product of Example 64b (95 mg, 0.49 mmol) was added phosphoric acid (1.5 mL) and the mixture was stirred at room temperature for 6 hours. The mixture was diluted with ethyl acetate and adjusted to pH=8 with saturated aqueous sodium carbonate and then the phases were separated. The aqueous layer was extracted with ethyl acetate. The combined organic phase was washed with brine, dried over anhydrous sodium sulfate and concentrated under reduced pressure. The residue was purified by silica gel column chromatography to afford the title compound as a light yellow oil (40 mg, Yield: 42%). $R_f$=0.3 (20:1 petroleum ether/ethyl acetate); $^1$H NMR (400 MHz, CDCl$_3$) δ 2.56 (d, J=6.0 Hz, 1H), 2.35 (t, J=6.8 Hz, 1H), 2.29-2.25 (m, 1H), 2.07 (d, J=0.4 Hz, 3H), 1.71 (s, 3H), 1.44-1.22 (m, 5H), 1.16 (s, 3H), 0.45 (s, 3H) ppm; Mass spectrum (ESI+ve) m/z 193 (M+H$^+$).

Examples 65

(±)-(3aR,7aS)-2,3,3a,7,7-pentamethyl-3a,4,5,6,7,7a-hexahydro-1H-inden-1-one

Example 65a 2-methyl-1-(2,6,6-trimethylcyclohex-1-enyl)but-2-en-1-ol

To a solution of 2,6,6-trimethylcyclohex-1-enecarbaldehyde (300 mg, 1.97 mmol) in tetrahydrofuran (7 mL) at −78° C. was added 1-methyl-1-propenylmagnesium bromide (0.5 M in tetrahydrofuran, 5.92 mL, 2.96 mmol) and then the mixture was warmed to room temperature and stirred for 2 hours. The mixture was quenched with saturated aqueous ammonium chloride and then extracted with ethyl acetate. The combined organic phase was washed with brine, dried over anhydrous sodium sulfate and concentrated under reduced pressure. Purification of the residue by silica gel column chromatography (eluent: petroleum ether/ethyl acetate=80/1) to afford the title compound as a colorless oil (256 mg, Yield: 62%). $R_f$=0.35 (20:1 petroleum ether/ethyl acetate); $^1$H NMR (400 MHz, CDCl$_3$) (Major isomer) δ 5.44-5.38 (m, 1H), 5.13 (s, 1H), 1.98-1.94 (m, 2H), 1.82 (s, 3H), 1.79 (d, J=8.0 Hz, 3H), 1.69 (s, 3H), 1.65-1.54 (m, 2H), 1.45-1.43 (m, 2H), 1.13 (s, 3H), 0.91 (s, 3H) ppm.

Example 65b 2-methyl-1-(2,6,6-trimethylcyclohex-1-enyl)but-2-en-1-one

To a solution of the product of Example 65a (250 mg, 1.20 mmol) in dichloromethane (8 mL) at 0° C. was added sodium bicarbonate (100.9 mg, 1.20 mmol) and Dess-Martin periodinane (1.0 g, 2.40 mmol). The mixture was warmed to room temperature and stirred for 2 hours. Saturated aqueous sodium bicarbonate (20 mL) was added to the reaction mixture and then the organics were extracted with dichloromethane. The organic phase was washed with brine, dried over anhydrous sodium sulfate and concentrated under reduced pressure. The residue was purified by silica gel column chromatography (eluent: petroleum ether/ethyl acetate=90/1) to afford 182 mg of a colorless oil which was further purified by prep-TLC to give the title compound as a mixture of isomers as a colorless oil (165 mg, Yield: 67%). $R_f$=0.5 (20:1 petroleum ether/ethyl acetate); $^1$H NMR (400 MHz, CDCl$_3$) δ 6.03-5.98 (m, 1H), 2.00-1.93 (m, 5H), 1.90-1.89 (m, 3H), 1.70-1.68 (m, 2H), 1.56 (s, 3H), 1.49-1.45 (m, 2H), 1.07 (s, 6H) ppm.

Examples 65

(±)-(3aR,7aS)-2,3,3a,7,7-pentamethyl-3a,4,5,6,7,7a-hexahydro-1H-inden-1-one

The product of Example 65b (60 mg, 0.29 mmol) was dissolved in phosphoric acid (0.5 mL) and the mixture was stirred at room temperature for 3 hours. To the solution was added water (3 mL) and the resulting mixture was extracted with ethyl acetate. The combined the organic phase was dried over anhydrous sodium sulfate and then concentrated under reduced pressure. The residue was purified by prep-TLC to afford the title compound as a colorless oil (42 mg, Yield: 70%). $R_f$=0.4 (20:1 petroleum ether/ethyl acetate); $^1$H NMR (400 MHz, CDCl$_3$) δ 1.90 (s, 3H), 1.80 (s, 1H), 1.64 (s, 3H), 1.64-1.47 (m, 4H), 1.37-1.34 (m, 2H), 1.21 (s, 3H), 1.13 (s, 3H), 0.84 (s, 3H) ppm; Mass spectrum (ESI+ve) m/z 207 (M+H$^+$).

Example 66

(±)-(1R,3aR,7aS)-2,3,3a,7,7-pentamethyl-3a,4,5,6,7,7a-hexahydro 1H inden-1-ol

To a mixture of lithium aluminum hydride (5.5 mg, 0.15 mmol) in dry tetrahydrofuran (1 mL) under argon at 0° C. was added a solution of the product of Example 65 (20 mg, 0.097 mmol) in dry tetrahydrofuran. The reaction was warmed to room temperature stirred for 2 hours. The reaction was quenched by the addition of the mixture of sodium sulfate and water. The mixture was filtered and then concentrated under reduced pressure. The residue combined with the crude product was purified by silica gel column chromatography (eluent: petroleum ether/ethyl acetate=100/1→80/1) to afford the title compound as a white solid (8.1 mg, Yield: 40%). Mp=73-75° C.; $R_f$=0.3 (20:1 petroleum ether/ethyl acetate); $^1$H NMR (400 MHz, CDCl$_3$) δ 4.34-4.31 (m, 1H), 1.62 (s, 3H), 1.57-1.46 (m, 4H), 1.34-1.21 (m, 6H), 1.15 (s, 3H), 1.09 (s, 3H), 1.08 (s, 3H), 0.85 (dt, J=12.8, 4.0 Hz, 1H) ppm; Mass spectrum (ESI+ve) m/z 191 (M−H$_2$O+H$^+$).

Example 67

(±)-(1R,7aS)-1,4,4-trimethyl-5,6,7,7a-tetrahydro-1H-inden-2(4H)-one

To a mixture of the product of Example 53 (39 mg, 0.24 mmol) in tetrahydrofuran (2 mL) at −78° C. under argon was added lithium diisopropylamide (2.0 M, 0.24 ml, 0.48 mmol). The mixture was warmed to room temperature and stirred for 1 hour and then cooled to −78° C. Methyl iodide (0.15 mL) was added to the mixture and then the reaction was again stirred at room temperature for 3 hours. The reaction was quenched with saturated aqueous ammonium chloride and then the mixture was extracted with ethyl acetate (20 mL×3) and the combined organic phase was washed with brine (20 mL), dried over anhydrous sodium sulfate and concentrated under reduced pressure. The residue was purified by prep-TLC to give the title compound as a yellow oil (14 mg, Yield: 33%). $R_f$=0.8 (10:1 petroleum ether/ethyl acetate); $^1$H NMR (400 MHz, CDCl3) δ 5.81 (s, 1H), 2.43-2.38 (m, 1H), 2.23-2.19 (m, 1H), 1.97-1.92 (m, 1H), 1.71-1.60 (m, 3H), 1.41-1.33 (m, 1H), 1.22 (s, 3H), 1.17-1.16 (m, 6H), 1.13-1.02 (m, 1H) ppm; Mass spectrum (ESI+ve) m/z 179 (M+H$^+$).

Example 68

(±)-(1R,3aS,7aS)-3a,7,7-trimethyloctahydro-1H-inden-1-ol

To a stirred solution of the product of Example 59 (45 mg, 0.25 mmol) in anhydrous tetrahydrofuran (4 mL) under argon at −78° C. was added lithium aluminum hydride (47 mg, 1.25 mmol). The reaction was allowed to warm to room temperature and stirred for 2 hours. The mixture was diluted with diethyl ether (20 mL) and wet sodium sulfate was added to quench the reaction. The resulting mixture was stirred for another 30 minutes and then filtered. The filtrate was concentrated under reduced pressure and the residue was purified by silica gel column chromatography (eluent: petroleum ether/ethyl acetate=50:1→10:1) to afford the title compound as a colorless liquid. $R_f$=0.6 (20:1 petroleum ether/ethyl acetate); $^1$H NMR (400 MHz, CDCl$_3$) δ 4.38 (dd, J=7.6, 4.0 Hz, 1H), 1.83-1.72 (m, 2H), 1.64-1.53 (m, 5H), 1.49-1.43 (m, 2H), 1.25-1.21 (m, 1H), 1.16 (s, 3H), 1.14 (d, J=4.0 Hz, 1H), 1.13 (s, 3H), 1.09 (d, J=4.0 Hz, 1H), 1.03 (s, 3H); $^{13}$C NMR (100 MHz, CDCl$_3$) δ 78.4, 59.2, 41.8, 39.5, 39.2, 37.7, 33.2, 32.1, 31.2, 30.8, 30.4, 19.6 ppm; Mass spectrum (ESI+ve) m/z 165 (M–H$_2$O+H$^+$).

Examples 69a and 69b (+)-4,4,7,7-tetramethyl-5,6,7,7a-tetrahydro-1H-inden-2(4H)-one (69a) and (−)-4,4,7,7-tetramethyl-5,6,7,7a-tetrahydro-1H-inden-2(4H)-one (69b)

The product of Example 41 (80 mg, 0.42 mmol) was resolved using chiral column (Chiralpark AY-H 5 cm ID×25 cm Length) HPLC chromatography (eluent: hexane/ethanol=95:5) to afford the title compound (69a) as a yellow solid (32 mg, Yield: 40%). Mp=35-38° C.; $^1$H NMR (400 MHz, CDCl$_3$+D$_2$O) δ 5.87 (d, J=1.6 Hz, 1H), 2.77 (dt, J=6.8, 1.8 Hz, 1H), 2.32 (dd, J=19.0, 6.6 Hz, 1H), 2.16 (dd, J=19.0, 2.2 Hz, 1H), 1.69-1.36 (m, 4H), 1.21 (s, 3H), 1.18 (s, 3H), 1.02 (s, 3H), 0.64 (s, 3H) ppm; Mass spectrum (ESI+ve) m/z 193 (M+H$^+$); $[α]_D^{25}$=+83.6° (c=0.61, dichloromethane). The title compound (69b) as a yellow solid (19.7 mg, Yield: 25%). $[α]_D^{25}$=−86.1° (c=0.36, dichloromethane).

Example 70

(3aR,7aS) and (3aS,7aR)-4,4,7,7-tetramethylhexahydro-1H-inden-2(3H)-one

To a solution of the product of Example 41 (110 mg, 0.57 mmol) in methanol (10 mL) was added 5% Pd/C (20 mg). The mixture was stirred at room temperature overnight under an atmosphere of hydrogen. The mixture was filtered and the filtrate concentrated under reduced pressure. The residue was purified by silica gel column chromatography to afford the title compound as a white solid (80 mg, Yield: 72%). $R_f$=0.7 (10:1 petroleum ether/ethyl acetate); $^1$H NMR (400 MHz, CDCl$_3$) δ 2.25-2.09 (m, 6H), 1.39-1.32 (m, 4H), 0.97 (s, 6H), 0.83 (s, 6H) ppm; Mass spectrum (ESI+ve) m/z 195 (M+H$^+$).

Example 71

(±)-(3R,3aR)-3,4,4-trimethyl-2,3,3a,4,5,6-hexahydro-1H-inden-1-one

Example 71a 1-(3,3-dimethylcyclohex-1-enyl)but-2-yn-1-ol

To a mixture of the product of 56a (700 mg, 5.0 mmol) in tetrahydrofuran (10 mL) at −78° C. under argon was added prop-1-ynylmagnesium bromide (0.5 M, 14.1 ml, 7.05 mmol) dropwise and then the reaction was warmed to room temperature and stirred for 3 hours. The reaction was quenched with saturated aqueous ammonium chloride and the organics were extracted with ethyl acetate (150 mL). The organic phase was washed with brine (50 mL×2), dried over anhydrous sodium sulfate and concentrated under reduced pressure to give the title compound as a colorless oil (844 mg, Yield: 95%). $^1$H NMR (400 MHz, CDCl$_3$) δ 5.56 (s, 1H), 4.68 (d, J=2.4 Hz, 1H), 2.12-2.04 (m, 2H), 1.88 (d, J=2.0 Hz, 3H), 1.72-1.64 (m, 3H), 1.43-1.40 (m, 2H), 0.99 (s, 3H), 0.98 (s, 3H).

Example 71b (E)-1-(3,3-dimethylcyclohex-1-enyl)but-2-en-1-ol

To a mixture of the product of Example 71a (844 mg, 4.73 mmol) in tetrahydrofuran (25 mL) at 0° C. under argon was added lithium aluminum hydride (720 mg, 19 mmol). The reaction was warmed to room temperature and stirred overnight. The reaction was quenched by water and then the organics were extracted with ethyl acetate (20 mL×4). The combined organic 3.0 phase was washed with water (100 mL), brine (100 mL), dried over anhydrous sodium sulfate and concentrated under reduced pressure. The residue was purified by silica gel chromatography to afford the title compound as a as colorless oil (300 mg, Yield: 35%). $^1$H NMR (400 MHz, CDCl$_3$) δ 5.71-5.66 (m, 1H), 5.52-5.46 (m, 1H), 5.43 (s, 1H), 4.38 (d, J=6.8 Hz, 1H), 1.94-1.86 (m, 2H), 1.71 (dd, J=6.4, 0.8 Hz, 3H), 1.65-1.61 (m, 2H), 1.48 (s, 1H), 1.42-1.38 (m, 2H), 0.97 (s, 3H), 0.97 (s, 3H) ppm.

Example 71c (E)-1-(3,3-dimethylcyclohex-1-enyl)but-2-en-1-one

To a mixture of the product of Example 71b (300 mg, 1.7 mol) in dichloromethane (10 mL) at 0° C. was added manganese dioxide (1.45 g, 17 mmol) and then it was warmed to room temperature and stirred for 3 days. The mixture was filtered and the filtrate was concentrated under reduced pressure. The residue was purified by silica gel chromatography to give the title compound as a colorless oil (121 mg, Yield: 40%). $^1$H NMR (400 MHz, CDCl$_3$) δ 6.89-6.84 (m, 1H), 6.68 (dd, J=1.6 Hz 15.2 Hz, 1H), 6.53 (s, 1H), 2.25-2.21 (m, 2H), 1.91 (dd, J=1.6 Hz 6.8 Hz, 3H), 1.68-1.62 (m, 2H), 1.47-1.44 (m, 2H), 1.07 (s, 6H) ppm.

Example 71

(±)-(3R,3aR)-3,4,4-trimethyl-2,3,3a,4,5,6-hexahydro-1H-inden-1-one

A mixture of the product of Example 71c (120 mg, 0.67 mol) in phosphoric acid (2 mL) was stirred at room temperature for 3 hours. Water was then added to the mixture and the organics were extracted with ethyl acetate (20 mL×3). The combined organic phase was washed with water (20 mL), brine (20 ml), dried over anhydrous sodium sulfate and concentrated under reduced pressure. The residue was purified by silica gel chromatography to afford the title compound as a colorless oil (78 mg, Yield: 65%). $R_f$=0.6 (10:1 petroleum ether/ethyl acetate); $^1$H NMR (400 MHz, CDCl$_3$) δ 6.69 (dd, J=2.8, 6.4 Hz, 1H), 2.42 (dd, J=12.4, 23.2 Hz, 1H), 2.24-2.06 (m, 3H), 1.99-1.90 (m, 2H), 1.50-

1.34 (m, 2H), 1.25 (d, J=6.0 Hz, 3H), 1.16 (s, 3H), 0.77 (s, 3H) ppm; Mass spectrum (ESI+ve) m/z 179 (M+H$^+$).

Example 72

(±)-(1S,3aS,7aS)-2,3,4,4-tetramethyl-3a,4,5,6,7,7a-hexahydro-1H-inden-1-ol

To a solution of the product of Example 64 (100 mg, 0.52 mmol) in tetrahydrofuran (2 mL) at 0° C. was added lithium aluminum hydride (118 mg, 3.12 mmol) and the reaction was, stirred at 0° C. for 3 hours. The reaction was quenched with saturated aqueous ammonium chloride and filtered. The filtrate was extracted with ethyl acetate and the combined organic phase was washed with brine, dried over anhydrous sodium sulfate and then concentrated under reduced pressure. The residue was purified by silica gel column chromatography to afford the title compound as a light brown oil (20.7 mg, Yield: 20%). R$_f$=0.3 (10:1 petroleum ether/ethyl acetate); $^1$H NMR (400 MHz, CDCl$_3$) δ 4.29 (s, 1H), 2.15 (d, J=7.6 Hz, 1H), 1.92-1.87 (m, 2H), 1.71 (s, 3H), 1.66 (s, 3H), 1.44-1.17 (m, 6H), 1.01 (s, 3H), 0.58 (s, 3H); $^{13}$C NMR (100 MHz, CDCl$_3$) δ 136.5, 133.9, 80.4, 53.9, 47.3, 39.8, 32.3, 32.1, 23.5, 22.1, 17.1, 15.0, 9.2 ppm; Mass spectrum (ESI+ve) m/z 177 (M−H$_2$O+H$^+$).

Example 73

(±)-(3aS,7aS)-2,3,4,4-tetramethyloctahydro-1H-inden-1-one

Example 73a (±)-(1R,3aS,7aS)-2,3,4,4-tetramethyloctahydro-1H-inden-1-ol

To the product of Example 64 (100 mg, 0.52 mmol) in tetrahydrofuran (2 mL) at 0° C. was added lithium aluminum hydride (118 mg, 3.12 mmol) and the reaction was stirred at 0° C. for 3 hours. The reaction was quenched with saturated aqueous ammonium chloride and filtered. The filtrate was extracted with ethyl acetate and the combined organic phase was washed with brine, dried over anhydrous sodium sulfate and concentrated under reduced pressure. The residue was purified by silica gel column chromatography on silica to give the title compound as a colorless oil (8.9 mg, Yield: 9%).

Example 73

(±)-(3aS,7aS)-2,3,4,4-tetramethyloctahydro-1H-inden-1-one

To the product of Example 73a (37 mg, 0.19 mmol) in tetrahydrofuran (2 mL) at 0° C. was added Dess-Martin periodinane (121 mg, 0.28 mmol) and stirred at 0° C. for 30 minutes. The mixture was added to petroleum ether and and filtered. The filtrate was concentrated under reduced pressure and the residue was purified by silica gel column chromatography to afford the title compound as a colorless oil (8.5 mg, Yield: 23%). R$_f$=0.6 (10:1 petroleum ether/ethyl acetate); $^1$H NMR (400 MHz, CDCl$_3$) δ 2.49-2.36 (m, 3H), 1.96-1.93 (m, 2H), 1.59-1.24 (m, 4H), 1.12 (s, 3H), 1.07-1.04 (m, 1H), 1.02-1.00 (m, 6H), 0.97 (d, J=7.2 Hz, 3H); $^{13}$C NMR (100 MHz, CDCl$_3$) δ 223.3, 51.5, 47.5, 43.2, 37.3, 35.3, 31.6, 30.8, 27.9, 25.9, 20.5, 15.1, 9.2 ppm; Mass spectrum (ESI+ve) m/z 195 (M+H$^+$).

Example 74

(±)-(3S,3aR,7aR)-3,4,4-trimethyloctahydro-1H-inden-1-one

Example 74a (±)-(3R,3aS,7aS)-3,4,4-trimethyloctahydro-1H-inden-1-ol

The mixture of the product of Example 71 (70 mg, 0.40 mmol) in methanol (4 mL) was added Raney-Ni and the reaction was stirred at room temperature over for 2.5 days under an atmosphere of hydrogen. The mixture was filtered and the filtrate was concentrated under reduced pressure. The residue was purified by silica gel chromatography to afford the title compound as a colorless oil (25 mg, Yield: 34%). $^1$H NMR (400 MHz, CDCl$_3$+D$_2$O) δ 4.20 (dd, J=8.8 Hz, 14.4 Hz, 1H), 2.18-2.08 (m, 1H), 2.01-1.90 (m, 2H), 1.61-1.53 (m, 4H), 1.48-1.13 (m, 4H), 1.02 (d, J=6.4 Hz, 3H), 0.95 (s, 3H), 0.88 (s, 3H) ppm.

Example 74

(±)-(3R,3aS,7aR)-3,4,4-trimethyloctahydro-1H-inden-1-one

To the solution of the product of Example 74a (25 mg, 0.14 mmol) in dichloromethane (3 mL) at room temperature was added sodium bicarbonate (12 mg, 0.14 mmol) and Dess-Martin periodinane (88 mg, 1.20 mmol) and the reaction was stirred overnight. The mixture was diluted with dichloromethane and washed with saturated sodium bicarbonate and brine. The organic phase was dried over anhydrous sodium sulfate and then concentrated under reduced pressure. The residue was purified by silica gel column chromatography to afford the title compound as a colorless oil (10 mg, Yield: 39%). R$_f$=0.6 (10:1 petroleum ether/ethyl acetate); $^1$H NMR (400 MHz, CDCl$_3$) δ 2.50 (dd, J=9.2 Hz, 19.2 Hz, 1H), 2.42 (dd, J=6.4 Hz, 13.2 Hz, 1H), 2.36-2.30 (m, 1H), 1.87-1.76 (m, 2H), 1.64 (dd, J=4.8 Hz, 8.0 Hz, 1H), 1.49-1.33 (m, 4H), 1.20-1.14 (m, 4H), 0.96 (s, 3H), 0.78 (s, 3H); $^{13}$C NMR (100 MHz, CDCl$_3$) δ 219.8, 53.0, 47.1, 45.2, 38.1, 32.4, 30.3, 28.5, 25.4, 23.3, 22.1, 19.2 ppm; Mass spectrum (ESI+ve) m/z 181 (M+H$^+$).

Example 75

7a-ethyl-4,4-dimethyl-5,6,7,7a-tetrahydro-1H-inden-2(4H)-one

Example 75a ethyl 1-ethyl-2-oxocyclohexanecarboxylate

To a stirred suspension of dry potassium carbonate (2.21 g, 16.0 mmol) in anhydrous acetone (45 mL) under argon was added ethyl 2-oxocyclohexanecarboxylate (1.36 g, 8.0 mmol) followed by ethyl iodide (2.0 mL, 24.9 mmol). The reaction was heated to reflux for 7 hours after which another portion of ethyl iodide (2.0 mL, 24.9 mmol) was added and the reaction was refluxed overnight. The cooled reaction mixture was diluted with diethyl ether (200 mL) and then filtered. The filtrate was concentrated under reduced pressure and the residue was purified by column chromatography (eluent: petroleum ether/ethyl acetate=300/1→50/1) to give the title compound as a colorless liquid (870 mg, Yield: 55%). $^1$H NMR (400 MHz, CDCl$_3$) δ 4.21 (q, J=7.2 Hz, 2H), 2.54-2.40 (m, 3H), 2.04-1.89 (m, 2H), 1.80-1.57 (m, 4H), 1.45-1.38 (m, 1H), 1.26 (t, J=7.2 Hz, 3H), 0.85 (t, J=7.4 Hz, 3H) ppm.

Example 75b ethyl 1-ethyl-3,3-dimethyl-2-oxocyclohexanecarboxylate

To a solution of potassium tert-butoxide (1.46 g, 13.02 mmol) in anhydrous tetrahydrofuran (15 mL) at −20° C. under argon was added dropwise a solution of the product of Example 75a (860 mg, 4.34 mmol) in anhydrous tetrahydrofuran (6 mL) over 15 minutes. The resulting mixture was stirred at −20° C. for 15 minutes after which time methyl iodide (1.7 mL, 27.3 mmol) was added dropwise at −20° C. The mixture was then allowed to warm gradually to room temperature and stirred for 2 hours. The mixture was poured into cooled half-saturated aqueous ammonium chloride (100 mL) and then extracted with diethyl ether (80 mL×3). The combined organic phase was washed with brine (150 mL), dried over anhydrous sodium sulfate and concentrated under reduced pressure. The residue was purified by silica gel column chromatography (eluent: petroleum ether/ethyl acetate=50/1) afforded the title compound as a colorless oil (768 mg, Yield: 78%). $^1$H NMR (400 MHz, CDCl$_3$) δ 4.22-4.05 (m, 2H), 2.60-2.54 (m, 1H), 2.11-1.95 (m, 2H), 1.74-1.68 (m, 1H), 1.66-1.51 (m, 3H), 1.31 (dt, J=13.2, 4.4 Hz, 1H), 1.23 (t, J=7.2 Hz, 3H), 1.08 (s, 3H), 1.07 (s, 3H), 0.78 (t, J=7.4 Hz, 3H) ppm.

Example 75c 6-ethyl-2,2-dimethylcyclohexanone

To a solution of the product of Example 75b (165 mg, 0.73 mmol) in methanol (2.34 mL) in a microwave vessel was added aqueous potassium hydroxide (6.25 M in water, 0.58 mL, 3.625 mmol). The vessel was sealed and heated to 110° C. for 6 hours. The mixture was diluted with water (25 mL) and extracted with diethyl ether (25 mL×7) and the combined organic phase was dried over anhydrous sodium sulfate and concentrated under reduced pressure. The residue was purified by flash chromatography (eluent: light petroleum ether/ethyl acetate=100/1) to afford the title compound as a light yellow oil (100 mg, Yield: 89%). $^1$H NMR (400 MHz, CDCl$_3$) δ 2.47-2.39 (m, 1H), 2.15-2.08 (m, 1H), 1.92-1.73 (m, 3H), 1.71-1.63 (m, 1H), 1.59-1.50 (m, 1H), 1.31-1.22 (m, 2H), 1.18 (s, 3H), 1.04 (s, 3H), 0.88 (t, J=7.4 Hz, 3H) ppm.

Example 75d 2-allyl-2-ethyl-6,6-dimethylcyclohexanone

Toa solution of the product of Example 75c (95 mg, 0.62 mmol) in tert-butanol (1 ml) in a microwave vessel was added potassium tert-butoxide (139 mg, 1.24 mmol) and 3-iodoprop-1-ene (0.17 mL, 1.86 mmol). The vessel was sealed and heated to 100° C. overnight. The cooled reaction mixture was transferred to a round bottom flask and concentrated under reduced pressure. The residue was dissolved in ethyl acetate (25 mL), washed with brine (25 mL), dried over anhydrous sodium sulfate and concentrated under reduced pressure. The residue was purified by flash chromatography (eluent: petroleum ether/ethyl acetate=100/1) to afford the title compound as a light yellow oil (71 mg, Yield: 59%). $^1$H NMR (400 MHz, CDCl$_3$) δ 5.67-5.56 (m, 1H), 5.04-4.99 (m, 2H), 2.34 (dd, J=13.8, 6.6 Hz, 1H), 2.17 (dd, J=13.8, 8.2 Hz, 1H), 1.82-1.61 (m, 6H), 1.56-1.49 (m, 2H), 1.10 (s, 3H), 1.08 (s, 3H), 0.75 (t, J=7.4 Hz, 3H) ppm.

Example 75e 2-ethyl-6,6-dimethyl-2-(2-oxopropyl)cyclohexanone

To a solution of the product of Example 75d (70 mg, 0.36 mmol) in dimethylacetamide (1.4 mL) and water (0.2 mL) was added palladium dichloride (6 mg, 0.036 mmol) and cupric acetate hydrate (18 mg, 0.09 mmol). The mixture was cooled to −78° C. and then evacuated and back-filled with an atmosphere of oxygen. The mixture was warmed to room temperature and stirred vigorously for approximately 4 days. The mixture was directly subjected to flash column chromatography (eluent: petroleum ether/ethyl acetate=50/1→20/1) to afford the title compound as a colorless oil (64 mg, Yield: 84%). $^1$H NMR (400 MHz, CDCl$_3$) δ 3.25 (d, J=18.0 Hz, 1H), 2.24 (d, J=18.4 Hz, 1H), 2.08 (s, 3H), 1.97-1.75 (m, 3H), 1.69-1.61 (m, 4H), 1.57-1.45 (m, 1H), 1.17 (s, 3H), 1.10 (s, 3H), 0.79 (t, J=7.4 Hz, 3H) ppm.

Example 75

7a-ethyl-4,4-dimethyl-5,6,7,7a-tetrahydro-1H-inden-2(4H)-one

To a stirred solution of the product of Example 75e (60 mg, 0.29 mmol) in xylenes (2 mL) was added powdered potassium hydroxide (8 mg, 0.14 mmol). The reaction was heated to 110° C. for 1 hour. The mixture was purified by flash column chromatography (eluent: petroleum ether/ethyl acetate=50/1→20/1) to give a 55 mg of a colorless oil which was further purified by silica gel column chromatography (eluent: petroleum ether/dichloromethane=10/1→1/2) to give 51 mg of a colorless oil which was further purified by prep-TLC (eluent: petroleum ether/ethyl acetate=10/1) to afford the title compound as a colorless oil (23 mg, Yield: 41%). R$_f$=0.3 (10:1 petroleum ether/ethyl acetate); $^1$H NMR (400 MHz, CDCl$_3$) δ 5.93 (s, 1H), 2.34 (d, J=18.0 Hz, 1H), 2.11 (d, J=18.4 Hz, 1H), 2.01-1.78 (m, 3H), 1.68-1.53 (m, 3H), 1.45-1.35 (m, 2H), 1.23 (s, 3H), 1.20 (s, 3H), 0.74 (t, J=7.4 Hz, 3H) ppm; Mass spectrum (ESI+ve) m/z 193 (M+H$^+$).

Example 76

(±)-(1S,7aR)-1-ethyl-4,4-dimethyl-5,6,7,7a-tetrahydro-1H-inden-2(4H)-one

To a solution of the product of Example 53 (76 mg, 0.46 mmol) in tetrahydrofuran (4 mL) at −78° C. was added lithium diisopropylamide (2.0 M, 0.92 mmol, 0.46 mL) and the mixture was warmed to room temperature and stirred for 30 minutes. The reaction mixture was recooled to 78° C. and iodoethane (717 mg, 0.37 mL, 4.6 mmol) was added. The mixture was gradually warmed to room temperature and then stirred for 3.5 hours. The reaction was quenched with saturated aqueous ammonium chloride (20 mL) and the organics were extracted with ethyl acetate (10 mL×3). The combined organic phase was washed with brine (10 mL) and then concentrated under reduced pressure. The residue was purified by prep-TLC to afford the title compound as a colorless oil (36 mg, Yield: 38%). $R_f$=0.4 (10:1 petroleum ether/ethyl acetate); $^1$H NMR (400 MHz, CDCl$_3$) δ 5.80 (s, 1H), 2.50 (d, J=5.6 Hz, J=12.8 Hz, 1H), 2.19-2.13 (m, 1H), 1.87-1.76 (m, 2H), 1.74-1.62 (m, 3H), 1.47-1.31 (m, 2H), 1.21 (s, 3H), 1.17 (s, 3H), 1.15-1.03 (m, 1H), 0.95 (t, J=7.6 Hz, 1H) ppm; Mass spectrum (ESI+ve) m/z 193 (M+H$^+$).

Example 77

(±)-(3aR,7aS)-4,4,7,7-tetramethyloctahydro-1H-inden-2-ol

To a mixture of the product of Example 70 (15 mg, 0.08 mol) in methanol (3 mL) at room temperature was added sodium borohydride (6 mg, 0.16 mmol) and the reaction was stirred for 2 hours. The reaction was diluted with ethyl acetate (60 mL) and the organic phase was washed with water (20 mL) and brine (20 mL), dried over anhydrous sodium sulfate and concentrated under reduced pressure. The residue was purified by silica gel column chromatography to give the title compound as white solid (12 mg, Yield: 76%). Mp=106.2-108° C.; $R_f$=0.6 (10:1 petroleum ether/ethyl acetate); $^1$H NMR (400 MHz, CDCl3) δ 4.38-4.34 (m, 1H), 2.08-2.00 (m, 2H), 1.68-1.62 (m, 2H), 1.51-1.37 (m, 5H), 1.29-1.22 (m, 2H), 0.83 (s, 6H), 0.80 (s, 6H); $^{13}$C NMR (100 MHz, CDCl3) δ 72.99, 47.11, 37.17, 34.08, 31.60, 31.01, 27.45 ppm; Mass spectrum (EI+ve) m/z 196 (M$^+$).

Example 78

4,4,7,7-tetramethyl-5,6,7,7a-tetrahydro-1H-inden-2 (4H)-one oxime

To a mixture of the product of Example 41 (30 mg, 0.16 mmol) in pyridine (1 mL) at room temperature was added hydroxylamine hydrochloride (33 mg, 0.47 mmol) and the reaction was warmed to 160° C. and stirred for 1 hour in a microwave reactor. The reaction was diluted with ethyl acetate the organic phase was washed with water (20 mL) and brine (20 mL) dried over anhydrous sodium sulfate and concentrated under reduced pressure. The residue was purified by silica gel column chromatography to afford the title compound as a white solid (11 mg, Yield: 33%). Mp=173.2-175.8° C.; $R_f$=0.6 (10:1 petroleum ether/ethyl acetate); $^1$H NMR (400 MHz, CDCl$_3$) δ 5.88 (s, 1H), 2.65-2.60 (m, 2H), 2.50-2.45 (m, 1H), 1.61-1.29 (m, 4H), 1.18 (s, 3H), 1.10 (s, 3H), 0.99 (s, 3H), 0.62 (s, 3H) ppm; Mass spectrum (ESI+ve) m/z 208 (M+H$^+$).

Example 79

(±)-(3aR,7aS)-4,4,7,7-tetramethylhexahydro-1H-inden-2(3H)-one oxime

To a mixture of the product of Example 70 (30 mg, 0.16 mmol) in pyridine (1 mL) at room temperature was added hydroxylamine hydrochloride (32 mg, 0.46 mmol) and the reaction was warmed to 160° C. and stirred for 20 minutes in a microwave reactor. The reaction was diluted with ethyl acetate the organic phase was washed with water (20 mL) and brine (20 mL), dried over anhydrous sodium sulfate and concentrated under reduced pressure. The residue was purified by silica gel column chromatography to afford the title compound as a white solid (25 mg, Yield: 77%). Mp=117.1-119° C.; $R_f$=0.6 (10:1 petroleum ether/ethyl acetate); $^1$H NMR (400 MHz, CDCl$_3$+D$_2$O) δ 7.60 (s, 1H), 2.44-2.34 (m, 4H), 1.90 (d, J=6.0 Hz, 2H), 1.39-1.28 (m, 4H), 0.96 (s, 3H), 0.95 (s, 3H), 0.85 (s, 3H) 0.82 (s, 3H) ppm; Mass spectrum (ESI+ve) m/z 210 (M+H$^+$).

BIOLOGY EXAMPLES

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The invention is described in more detail in the following non-limiting examples. It is to be understood that these particular methods and examples in no way limit the invention to the embodiments described herein and that other embodiments and uses will no doubt suggest themselves to those skilled in the art.

Reagents

Monoclonal anti-rhodopsin 1D4 antibody can be purchased from University of British Columbia.

Cell Lines and Culture Conditions

Stable cell lines expressing opsin protein were generated using the Flp-In T-Rex system. The stable cells were grown in DMEM high glucose media supplemented with 10% (v/v) fetal bovine serum, antibiotic/antimycotic solution, 5 μ/ml blasticidin and hygromycin at 37° C. in presence of 5% CO$_2$. For all the experiments the cells were allowed to reach confluence and were induced to produce opsin with 1 μg/mL tetracycline after change of media and then compounds were added. The plates were incubated for 48 hours after which the cells were harvested.

SDS-PAGE and Western Blotting

Proteins were separated on SDS-PAGE gels and western blotted as described in (Noorwez et al., J. Biol. Chem. 279, 16278-16284 (2004)).

The in vivo efficacy of the compounds of the invention in treating macular degeneration can be demonstrated by various tests well known in the art. For example, human patients are selected based on a diagnosis of macular degeneration (such as where there is a gross diagnosis of this condition or where they have been shown to exhibit build-up of toxic visual cycle products, such as A2E, lipofuscin, or drusen in their eyes. A compound of the invention, such as that of Formula I, is administered to a test group while a placebo, such as PBS or DMSO, is administered to a control group that may be as large or may be somewhat smaller than the test group. The test compound is administered either on a one time basis or on a sequential basis (for example, weekly or daily) or according to some other predetermined schedule. Administration of the test compound is normally by oral or parenteral means and in an amount effective to retard the development and/or reoccurrence of macular degeneration. An effective dose amount is generally in the range of about 1 to 5,000 mg or in the range of 10 to 2,000 mg/kg. Administration may include multiple doses per day.

Efficacy of the test compound in retarding progression of macular degeneration is generally by measuring increase in visual acuity (for example, using Early Treatment Diabetic RP Study (ETDRS) charts (Lighthouse, Long Island, N.Y.). Other means of following and evaluating efficacy is by measuring/monitoring the autofluorescence or absorption spectra of such indicators as N-retinylidene-phosphatidylethanolamine, dihydro-N-retinylidene-N-retinyl-phosphatidylethanolamine, N-retinylidene-N-retinyl-phosphatidylethanolamine, dihydro-N-retinylidene-N-retinyl-ethanolamine, and/or N-retinylidene-phosphatidylethanolamine in the eye of the patient. Autofluorescence is monitored using different types of instrument, for example, a confocal scanning laser ophthalmoscope.

Accumulation of lipofuscin in the retinal pigment epithelium (RPE) is a common pathological feature observed in various degenerative diseases of the retina. A toxic vitamin A-based fluorophore (A2E) present within lipofuscin granules has been implicated in death of RPE and photoreceptor cells. Such experiments can employ an animal model that manifests accelerated lipofuscin accumulation to evaluate the efficacy of a therapeutic approach based upon reduction of serum vitamin A (retinol). Administration of test compound to mice harboring a null mutation in the Stargardt's disease gene (ABCA4) produces reductions in serum retinol/retinol binding protein and arrested accumulation of A2E and lipofuscin autofluorescence in the RPE.

Test animals are available for use in testing efficacy of a test compound in reducing build-up of toxic pigments, such as lipofuscin. For example, mice have been produced that exhibit increased production of such toxic product. Such mice have been described in the literature (see, for example, Widder et al., U.S. Pub. 2006/0167088) and their value and utility are well known to those in the art.

Showing the efficacy of compounds of the invention in protecting against light toxicity is conveniently performed by methods well known in the art (see, for example, Sieving et al, PNAS, Vol. 98, pp 1835-40 (2001)).

Biology Example 1

Rhodopsin Purification and Regeneration

P23H cells were grown to confluency in 10 centermeter plates in DMEM containing high glucose, blasticidin (5 µg/ml) and hygromycin (100 µg/ml). The cells were induced with tetracycline (1 µg/ml) and treated with either DMSO (vehicle) or different concentrations of the test (0.3 µM, 1 µM, 3 µM, 10 µM, 30 µM and 80 µM). After 24 hours, the medium was removed and fresh medium with the compounds was added to the plates. β-Ionone (20 µM) was used as a positive control for the experiments. The cells were harvested 48 hours after the first treatment. All procedures from hereon were carried out under a dim red light (>660 nm). The cells were washed twice with PBS, and incubated for 1 hour at room temperature in 1 mL of PBS containing 9-cis-retinal (20 µM). After regeneration, the cells were washed with PBS and incubated for 1 hour at 4° C. in PBS containing 1% n-dodecyl-β-D maltoside and protease inhibitors (Roche) for lysis. The cell lysate was centrifuged in a tabletop Beckman ultracentrifuge at 36,000×g for 10 minutes. The supernatant was removed and protein was estimated in all of the samples (DC protein assay, Biorad). Equal amounts of protein (5 µg) was loaded on previously prepared 1D4-coupled cyanogen bromide-activated Sepharose 4B beads for 1 hour at 4° C. Briefly, the Sepharose 4B beads were conjugated with 1D4 antibody that recognizes the C-terminus of opsin. The beads were extensively washed three times with PBS and twice with sodium phosphate buffer (10 mM, pH 6.0), both containing 0.1% n-dodecyl-β-D maltoside. The protein was eluted in the sodium phosphate buffer containing a synthetic 9 amino acid peptide corresponding to the C-terminus of opsin protein. The eluted rhodopsin was analyzed on a spectrophotometer scanning the UV-visible range from 250 to 650 nm at increments of 1 nm.

Table 1 contains the results of β-ionone (reference compound 1) and test compounds in which the 480-500 nm absorbance is expressed as a fold increase over the DMSO control. FIG. 1 is the spectral results using β-ionone according to Biology Example 1.

TABLE 1

| Compound | Fold Increase Over Control | Concentration (µM) |
| --- | --- | --- |
| β-ionone | 2.4 | 20 |
| 1 | 1.7 | 10 |
| 3 | 2.2 | 20 |
| 5 | 1.7 | 10 |
| 8 | 2.1 | 20 |
| 13 | 2.2 | 20 |
| 14 | 2.4 | 20 |
| 16 | 2.2 | 20 |
| 18 | 1.7 | 20 |
| 20 | 1.9 | 20 |
| 22 | 1.8 | 20 |
| 26 | 2.3 | 20 |
| 27 | 2.0 | 10 |
| 28 | 1.7 | 10 |
| 29 | 2.4 | 10 |
| 30 | 1.8 | 10 |
| 31 | 1.6 | 10 |
| 33 | 1.8 | 10 |
| 34 | 2.2 | 10 |
| 36 | 2.0 | 10 |
| 37 | 1.8 | 10 |
| 40 | 1.8 | 10 |
| 41 | 1.9 | 10 |
| 43 | 1.7 | 10 |
| 44 | 2.2 | 10 |
| 45 | 3.0 | 10 |
| 46 | 1.8 | 10 |
| 51 | 1.7 | 10 |
| 53 | 1.7 | 10 |
| 55 | 2.8 | 10 |
| 56 | 1.7 | 10 |
| 58 | 2.0 | 20 |
| 60 | 2.1 | 20 |
| 61 | 1.8 | 20 |
| 62 | 2.3 | 20 |
| 63 | 2.3 | 20 |
| 64 | 2.1 | 20 |
| 65 | 1.8 | 20 |
| 66 | 1.9 | 20 |
| 67 | 1.8 | 20 |
| 69a | 2.0 | 20 |
| 69b | 1.8 | 20 |
| 70 | 1.9 | 20 |
| 71 | 2.2 | 20 |
| 72 | 1.9 | 20 |

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A compound of Formula I,

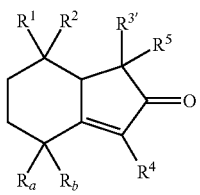

Formula I wherein $R^1$ and $R^2$ are independently:
1) hydrogen,
2) —$CH_3$, or
1) —$CH_2CH_3$, $R_a$ and $R_b$, are each independently:
1) hydrogen,
2) —$CH_3$, or
3) —$CH_2CH_3$;

$R^{3'}$ and $R^5$ are each independently:
1) hydrogen, or
2) lower alkyl; and $R^4$ is
1) hydrogen,
2) cycloalkyl, or
3) phenyl;

wherein if either $R^1$ or $R^2$ is hydrogen then each of $R_a$ and $R_b$ is selected from methyl and ethyl, including pharmaceutically acceptable salts, solvates and hydrates thereof.

2. The compound of claim 1, wherein $R^{3'}$ is hydrogen and $R^4$ is hydrogen.

3. A method of inhibiting the formation or accumulation of a visual cycle product, comprising contacting an opsin protein with a compound of Formula I

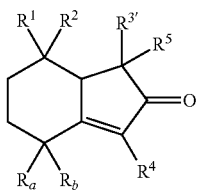

Formula I wherein $R^1$ and $R^2$ are independently:
1) hydrogen,
2) —$CH_3$, or
1) —$CH_2CH_3$, $R_a$ and $R_b$ are each independently:
1) hydrogen,
2) —$CH_3$, or
3) —$CH_2CH_3$;

$R^{3'}$ and $R^5$ are each independently:

1) hydrogen, or
2) lower alkyl; and $R^4$ is:
1) hydrogen,
2) cycloalkyl, or
3) phenyl;

wherein if either $R^1$ or $R^2$ is hydrogen then each of $R_a$ and $R_b$ is selected from methyl and ethyl, including pharmaceutically acceptable salts, solvates and hydrates thereof.

4. The method of claim 3, wherein said compound reduces mislocalization of said opsin protein.

5. The method of claim 3, wherein said opsin protein is present in a cell.

6. The method of claim 3, wherein said cell is a cone cell or rod cell.

7. The method of claim 3, wherein said cell is present in a mammalian eye.

8. The method of claim 3, wherein said visual cycle product is a toxic visual cycle product.

9. The method of claim 8, wherein said toxic visual cycle product is lipofuscin or N-retinylidene-N-retinylethanolamine (A2E).

10. A method of inhibiting the formation or accumulation of a visual cycle product, comprising contacting an opsin protein with a compound selected from the group consisting of:

(±)-(3aS,7aS)-methyl 3a,7,7-trimethyl-3a,4,5,6,7,7a-hexahydro-1H-indene-2-carboxylate (Compound 8);
2,7,7-trimethyl-2,3,4,5,6,7-hexahydro-1H-isoindol-1-one (Compound 13);
(±)-(3aR,7aS)-3,3a,7,7-tetramethyl-3a,4,5,6,7,7a-hexahydro-1H-inden-1-one oxime (Compound 14);
(±)-(3R,3aS,7aS)-3,3a,7,7-tetramethyloctahydro-1H-inden-1-one oxime (Compound 16);
(±)-(1R,7aS)-1,4,4,7a-tetramethyl-5,6,7,7a-tetrahydro-1H-inden-2(4H)-one (Compound 20);
(±)-((3aS,7aS)-3a,7,7-trimethyl-3a,4,5,6,7,7a-hexahydro-1H-inden-2-yl)methanol (Compound 22);
(±)-((3aS,7aS)-3a,7,7-trimethyloctahydro-1H-inden-2-yl)methanol (Compound 26);
7,7-dimethyl-5,6,7,7a-tetrahydro-1H-inden-2(4H)-one (Compound 27);
(±)-(3aR,7aS)-3-isopropyl-3a,7,7-trimethyl-3a,4,5,6,7,7a-hexahydro-1H-inden-1-one (Compound 29);
4,4,7a-trimethyl-5,6,7,7a-tetrahydro-1H-inden-2(4H)-one oxime (Compound 30);
(±)-(3aS,7aR)-4,4,7a-trimethyloctahydro-1H-inden-1-one oxime (Compound 33);
(±)-(3aR,7aS)-3-ethyl-3a,7,7-trimethyl-3a,4,5,6,7,7a-hexahydro-1H-inden-1-one (Compound 34);
(±)-(1S,3aS,7aS)-3a,7,7-trimethyl-3a,4,5,6,7,7a-hexahydro-1H-inden-1-ol (Compound 36);
(±)-(1R,3aS,7aS)-3a,7,7-trimethyl-3a,4,5,6,7,7a-hexahydro-1H-inden-1-ol (Compound 37);
4,4,7,7-tetramethyl-5,6,7,7a-tetrahydro-1H-inden-2(4H)-one (Compound 41);
(±)-(3aR,7aS)-3-cyclopropyl-3a,7,7-trimethyl-3a,4,5,6,7,7a-hexahydro-1H-inden-1-one (Compound 44);
(±)-(3aR,7aS)-3-isopropyl-3a,7,7-trimethyl-3a,4,5,6,7,7a-hexahydro-1H-inden-1-one oxime (Compound 45);
(±)-(3S,3aS,7aS)-3-isopropyl-3a,7,7-trimethyloctahydro-1H-inden-1-one (Compound 46);
4,4-dimethyl-5,6,7,7a-tetrahydro-1H-inden-2(4H)-one (Compound 53);
4,4-dimethylhexahydro-1H-inden-2(3H)-one oxime (Compound 55);

(±)-(1S,3S,3aS,7aS)-3-isopropyl-3a,7,7-trimethyloctahydro-1H-inden-1-ol (Compound 58);
(±)-(1S,3aS,7aS)-3a,7,7-trimethyloctahydro-1H-inden-1-ol (Compound 60);
(±)-(3aS,7aS)-3a,7,7-trimethylhexahydro-1H-inden-2(3H)-one oxime (Compound 62);
(±)-(3aS,7aS)-3a,7,7-trimethyloctahydro-1H-inden-2-ol (Compound 63);
(±)-(3aS,7aS)-2,3,4,4-tetramethyl-3a,4,5,6,7,7a-hexahydro-1H-inden-1-one (Compound 64);
(±)-(1R,3aR,7aS)-2,3,3a,7,7-pentamethyl-3a,4,5,6,7,7a-hexahydro 1H inden-1-ol (Compound 66);
(±)-(1R,7aS)-1,4,4-trimethyl-5,6,7,7a-tetrahydro-1H-inden-2(4H)-one (Compound 67);
(+)-4,4,7,7-tetramethyl-5,6,7,7a-tetrahydro-1H-inden-2(4H)-one (Compound 69a);
(3aR,7aS) and (3aS,7aR)-4,4,7,7-tetramethylhexahydro-1H-inden-2(3H)-one (Compound 70);
(±)-(1S,3aS,7aS)-2,3,4,4-tetramethyl-3a,4,5,6,7,7a-hexahydro-1H-inden-1-ol (Compound 72);
(±)-(3aS,7aS)-2,3,4,4-tetramethyloctahydro-1H-inden-1-one (Compound 73);
(±)-(3R,3aS,7aR)-3,7,7-trimethyloctahydro-1H-inden-1-one (Compound 74);
7a-ethyl-4,4-dimethyl-5,6,7,7a-tetrahydro-1H-inden-2(4H)-one (Compound 75);
(±)-(1R,7aS)-1-ethyl-4,4,7a-trimethyl-5,6,7,7a-tetrahydro-1H-inden-2(4H)-one (Compound 76);
(±)-(3aR,7aS)-4,4,7,7-tetramethyloctahydro-1H-inden-2-ol (Compound 77);
4,4,7,7-tetramethyl-5,6,7,7a-tetrahydro-1H-inden-2(4H)-one oxime (Compound 78); and
(±)-(3aR,7aS)-4,4,7,7-tetramethylhexahydro-1H-inden-2(3H)-one oxime (Compound 79),
or a pharmaceutically acceptable salt thereof.

11. A composition, comprising a therapeutically effective amount of a compound of claim 1 in a pharmaceutically acceptable carrier.

12. A compound selected from the group consisting of:
(±)-(3aS,7aS)-methyl 3a,7,7-trimethyl-3a,4,5,6,7,7a-hexahydro-1H-indene-2-carboxylate (Compound 8);
2,7,7-trimethyl-2,3,4,5,6,7-hexahydro-1H-isoindol-1-one (Compound 13);
(±)-(3aR,7aS)-3,3a,7,7-tetramethyl-3a,4,5,6,7,7a-hexahydro-1H-inden-1-one oxime (Compound 14);
(±)-(3R,3aS,7aS)-3,3a,7,7-tetramethyloctahydro-1H-inden-1-one oxime (Compound 16);
(±)-(1R,7aS)-1,4,4,7a-tetramethyl-5,6,7,7a-tetrahydro-1H-inden-2(4H)-one (Compound 20);
(±)-((3aS,7aS)-3a,7,7-trimethyl-3a,4,5,6,7,7a-hexahydro-1H-inden-2-yl)methanol (Compound 22);
(±)-((3aS,7aS)-3a,7,7-trimethyloctahydro-1H-inden-2-yl)methanol (Compound 26);
7,7-dimethyl-5,6,7,7a-tetrahydro-1H-inden-2(4H)-one (Compound 27);
(±)-(3aR,7aS)-3-isopropyl-3a,7,7-trimethyl-3a,4,5,6,7,7a-hexahydro-1H-inden-1-one (Compound 29);
4,4,7a-trimethyl-5,6,7,7a-tetrahydro-1H-inden-2(4H)-one oxime (Compound 30);
(±)-(3aS,7aR)-4,4,7a-trimethyloctahydro-1H-inden-1-one oxime (Compound 33);
(±)-(3aR,7aS)-3-ethyl-3a,7,7-trimethyl-3a,4,5,6,7,7a-hexahydro-1H-inden-1-one (Compound 34);
(±)-(1S,3aS,7aS)-3a,7,7-trimethyl-3a,4,5,6,7,7a-hexahydro-1H-inden-1-ol (Compound 36);
(±)-(1R,3aS,7aS)-3a,7,7-trimethyl-3a,4,5,6,7,7a-hexahydro-1H-inden-1-ol (Compound 37);
4,4,7,7-tetramethyl-5,6,7,7a-tetrahydro-1H-inden-2(4H)-one (Compound 41);
(±)-(3aR,7aS)-3-cyclopropyl-3a,7,7-trimethyl-3a,4,5,6,7,7a-hexahydro-1H-inden-1-one (Compound 44);
(±)-(3aR,7aS)-3-isopropyl-3a,7,7-trimethyl-3a,4,5,6,7,7a-hexahydro-1H-inden-1-one oxime (Compound 45);
(±)-(3S,3aS,7aS)-3-isopropyl-3a,7,7-trimethyloctahydro-1H-inden-1-one (Compound 46);
4,4-dimethyl-5,6,7,7a-tetrahydro-1H-inden-2(4H)-one (Compound 53);
4,4-dimethylhexahydro-1H-inden-2(3H)-one oxime (Compound 55);
(±)-(1S,3S,3aS,7aS)-3-isopropyl-3a,7,7-trimethyloctahydro-1H-inden-1-ol (Compound 58);
(±)-(1S,3aS,7aS)-3a,7,7-trimethyloctahydro-1H-inden-1-ol (Compound 60);
(±)-(3aS,7aS)-3a,7,7-trimethylhexahydro-1H-inden-2(3H)-one oxime (Compound 62);
(±)-(3aS,7aS)-3a,7,7-trimethyloctahydro-1H-inden-2-ol (Compound 63);
(±)-(3aS,7aS)-2,3,4,4-tetramethyl-3a,4,5,6,7,7a-hexahydro-1H-inden-1-one (Compound 64);
(±)-(1R,3aR,7aS)-2,3,3a,7,7-pentamethyl-3a,4,5,6,7,7a-hexahydro 1H inden-1-ol (Compound 66);
(±)-(1R,7aS)-1,4,4-trimethyl-5,6,7,7a-tetrahydro-1H-inden-2(4H)-one (Compound 67);
(+)-4,4,7,7-tetramethyl-5,6,7,7a-tetrahydro-1H-inden-2(4H)-one (Compound 69a);
(3aR,7aS) and (3aS,7aR)-4,4,7,7-tetramethylhexahydro-1H-inden-2(3H)-one (Compound 70);
(±)-(1S,3aS,7aS)-2,3,4,4-tetramethyl-3a,4,5,6,7,7a-hexahydro-1H-inden-1-ol (Compound 72);
(±)-(3aS,7aS)-2,3,4,4-tetramethyloctahydro-1H-inden-1-one (Compound 73);
(±)-(3R,3aS,7aR)-3,7,7-trimethyloctahydro-1H-inden-1-one (Compound 74);
7a-ethyl-4,4-dimethyl-5,6,7,7a-tetrahydro-1H-inden-2(4H)-one (Compound 75);
(±)-(1R,7aS)-1-ethyl-4,4,7a-trimethyl-5,6,7,7a-tetrahydro-1H-inden-2(4H)-one (Compound 76);
(±)-(3aR,7aS)-4,4,7,7-tetramethyloctahydro-1H-inden-2-ol (Compound 77);
4,4,7,7-tetramethyl-5,6,7,7a-tetrahydro-1H-inden-2(4H)-one oxime (Compound 78); and
(±)-(3aR,7aS)-4,4,7,7-tetramethylhexahydro-1H-inden-2(3H)-one oxime (Compound 79),
or a pharmaceutically acceptable salt thereof.

13. A composition comprising a compound of claim 12, or a pharmaceutically acceptable salt thereof.

14. A compound selected from the group consisting of:

| Name | Structure |
| --- | --- |
| 7,7-dimethyl-5,6,7,7a-tetrahydro-1H-inden-2(4H)-one | 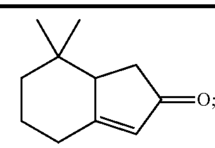 |
| (−)-4,4,7,7-tetramethyl-5,6,7,7a-tetrahydro-1H-inden-2(4H)-one | 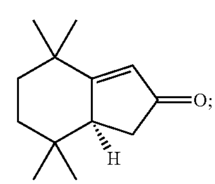 |

| Name | Structure |
|---|---|
| (+)-4,4,7,7-tetramethyl-5,6,7,7a-tetrahydro-1H-inden-2(4H)-one | 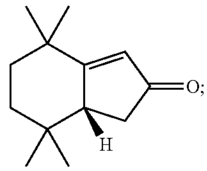 |
| 4,4-dimethyl-5,6,7,7a-tetrahydro-1H-inden-2(4H)-one | 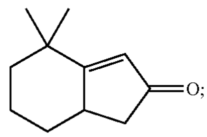 |
| 4,4,7,7-tetramethyl-5,6,7,7a-tetrahydro-1H-inden-2(4H)-one | 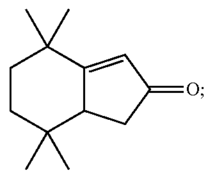 |
| (±)-(3aS,7aS)-3a,7,7-trimethylhexahydro-1H-inden-2(3H)-one | 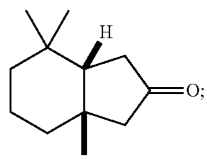 |
| (±)-(3aR,7aS)-3,3a,7,7-tetramethyl-3a,4,5,6,7,7a-hexahydro-1H-inden-1-one oxime | 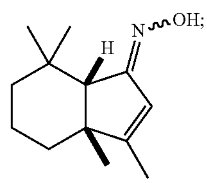 |
| 2,7,7-trimethyl-2,3,4,5,6,7-hexahydro-1H-isoindol-1-one | 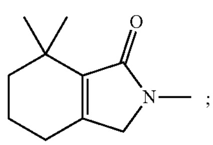 |
| (±)-(3aR,7aS)-3,3a,7,7-tetramethyl-3a,4,5,6,7,7a-hexahydro-1H-inden-1-one | 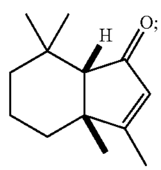 |
| (±)-(3R,3aR)-3,4,4-trimethyl-2,3,3a,4,5,6-hexahydro-1H-inden-1-one | 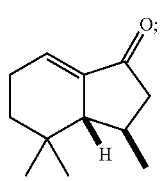 |

| Name | Structure |
|---|---|
| (3aR,7aS)-4,4,7,7-tetramethylhexahydro-1H-inden-2(3H)-one | 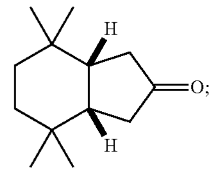 |
| (±)-(1R,7aS)-1,4,4-trimethyl-5,6,7,7a-tetrahydro-1H-inden-2(4H)-one | 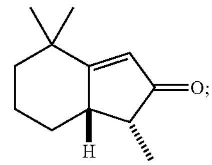 |
| (±)-(1R,3aR,7aS)-2,3,3a,7,7-pentamethyl-3a,4,5,6,7,7a-hexahydro 1H inden-1-ol | 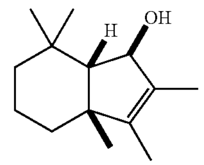 |
| (±)-(3aS,7aS)-2,3,4,4-tetramethyl-3a,4,5,6,7,7a-hexahydro-1H-inden-1-one | |
| (±)-(3aS,7aS)-3a,7,7-trimethyloctahydro-1H-inden-2-ol | 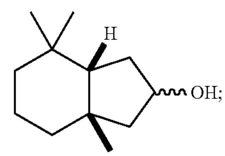 |
| (±)-(3aS,7aS)-3a,7,7-trimethylhexahydro-1H-inden-2(3H)-one oxime | | and or a pharmaceutically acceptable salt thereof.

15. A composition comprising a compound of claim 14, or a pharmaceutically acceptable salt thereof, and a pharmaceutically acceptable carrier.

16. A method of inhibiting the formation or accumulation of a visual cycle product, comprising contacting an opsin protein with a compound of claim 14, or a pharmaceutically acceptable salt thereof.

* * * * *